United States Patent
Ho et al.

(10) Patent No.: US 10,414,820 B2
(45) Date of Patent: *Sep. 17, 2019

(54) ANTIGEN BINDING CONSTRUCTS TO CD8

(71) Applicant: IMAGINAB, INC., Inglewood, CA (US)

(72) Inventors: David T. Ho, Long Beach, CA (US); Tove Olafsen, Reseda, CA (US); Giti Agahi, Los Angeles, CA (US); Christian P. Behrenbruch, Inglewood, CA (US)

(73) Assignee: IMAGINAB, INC., Inglewood, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/773,710

(22) PCT Filed: Mar. 10, 2014

(86) PCT No.: PCT/US2014/022782
§ 371 (c)(1),
(2) Date: Sep. 8, 2015

(87) PCT Pub. No.: WO2014/164553
PCT Pub. Date: Oct. 9, 2014

(65) Prior Publication Data
US 2016/0024209 A1     Jan. 28, 2016

Related U.S. Application Data

(60) Provisional application No. 61/780,286, filed on Mar. 13, 2013.

(51) Int. Cl.
| | |
|---|---|
| *A61K 39/395* | (2006.01) |
| *C07K 16/28* | (2006.01) |
| *A61K 47/68* | (2017.01) |
| *A61K 51/10* | (2006.01) |
| *G01N 33/566* | (2006.01) |
| *G01N 33/68* | (2006.01) |
| *A61K 39/00* | (2006.01) |

(52) U.S. Cl.
CPC ...... *C07K 16/2815* (2013.01); *A61K 47/6849* (2017.08); *A61K 51/1027* (2013.01); *G01N 33/566* (2013.01); *G01N 33/6872* (2013.01); *A61K 2039/505* (2013.01); *C07K 2317/24* (2013.01); *C07K 2317/31* (2013.01); *C07K 2317/35* (2013.01); *C07K 2317/56* (2013.01); *C07K 2317/565* (2013.01); *C07K 2317/622* (2013.01); *C07K 2317/624* (2013.01); *C07K 2317/626* (2013.01); *C07K 2317/92* (2013.01); *G01N 2333/70517* (2013.01)

(58) Field of Classification Search
None
See application file for complete search history.

(56) References Cited

U.S. PATENT DOCUMENTS

| | | |
|---|---|---|
| 4,281,061 A | 7/1981 | Zuk et al. |
| 4,709,015 A | 11/1987 | Kung et al. |
| 4,816,567 A | 3/1989 | Cabilly et al. |
| 4,946,778 A | 8/1990 | Ladner et al. |
| 5,601,819 A | 2/1997 | Wong et al. |
| 5,837,821 A | 11/1998 | Wu |
| 5,977,322 A | 11/1999 | Marks et al. |
| 8,383,778 B2 | 2/2013 | Hsieh et al. |
| 2005/0244333 A1 | 11/2005 | Yazaki et al. |
| 2006/0099582 A1 | 5/2006 | Papdopoulos et al. |
| 2008/0095770 A1 | 4/2008 | Umana et al. |
| 2010/0033105 A1 | 2/2010 | Yamauchi et al. |
| 2010/0111959 A1 | 5/2010 | Swanson et al. |
| 2011/0110854 A1 | 5/2011 | McBride et al. |
| 2011/0268656 A1 | 11/2011 | Ho et al. |
| 2015/0191543 A1 | 7/2015 | Wu et al. |
| 2016/0024209 A1 | 1/2016 | Ho et al. |

FOREIGN PATENT DOCUMENTS

| | | |
|---|---|---|
| EP | 2 476 754 A1 | 7/2012 |
| JP | H08-500979 A | 2/1996 |
| JP | 2001-502922 A | 3/2001 |
| WO | WO 98/52975 | 11/1998 |
| WO | WO 2007/109321 | 9/2007 |
| WO | WO 2011/069019 A2 | 6/2011 |
| WO | WO 2012/143524 | 10/2012 |
| WO | WO 2013/020074 A2 | 2/2013 |
| WO | WO 20140/25828 | 2/2014 |
| WO | WO 2017/176769 A1 | 10/2017 |

OTHER PUBLICATIONS

Peng et al. (Cancer Res; 72(20); 5209-18, 2012).*
Overwijk et al. (The Journal of Experimental Medicine, vol. 198, No. 4, Aug. 18, 2003 569-580).*
Klein et al. (Clin Cancer Res 2009;2507 15(7), 2009).*
Cipponi et al. (Cancer Immunol Immunother (2011) 60:1153-1160).*
Deri et al. (Nucl Med Biol. Jan. 2013 ; 40(1): 3-14).*
Nangengast et al. (Cancer Res; 71(1); 143-53. 2010).*
Vosjan et al. (Mol Cancer Ther; 11(4); 1017-25. 2012).*
InvivoGen, 2011, "Engineering Fc regions for altered properties," pp. 1-4, retrieved using the WayBackMachine Internet Archive captured on Dec. 13, 2011 (with banner on top removed).*
InvivoGen, 2011, "Engineering Fc regions for altered properties," pp. 1-4, retrieved using the WayBackMachine Internet Archive captured on Dec. 13, 2011 (including banner on top).*

(Continued)

*Primary Examiner* — Zachary S Skelding
(74) *Attorney, Agent, or Firm* — Knobbe, Martens, Olson & Bear, LLP

(57) ABSTRACT

Antigen binding constructs that bind to CD8, for example antibodies, including antibody fragments (such as scFv, minibodies, and cys-diabodies) that bind to CD8, are described herein. Methods of use are described herein.

21 Claims, 49 Drawing Sheets

Specification includes a Sequence Listing.

(56) References Cited

OTHER PUBLICATIONS

Benny K.C. Lo, Methods in Molecular Biology, vol. 248: Antibody Engineering: Methods and Protocols, 2004, Humana Press Inc., pp. 135-159.*
O'Brien et al. (Humanization of Monoclonal Antibodies by CDR Grafting. In: Welschof M., Krauss J. (eds) Recombinant Antibodies for Cancer Therapy. Methods in Molecular Biology™, vol. 207. Humana Press (2003)) (Year: 2003).*
Gillies et al. (Hum Antibodies Hybridomas. 1990;1(1):47-54.) (Year: 1990).*
Al-Lazikani et al., "Standard conformations for the canonical structures of immunoglobulins", Journal of Molecular Biology, vol. 273, Issue 4, pp. 927-948, 1997.
Altschul et al., "Basic local alignment search tool", Journal of Molecular Biology, vol. 215, Issue 3, Oct. 5, 1990, pp. 403-410.
Altschul et al., "Gapped BLAST and PSI-BLAST: a new generation of protein database search programs", Nucleic Acids Research, 1997, vol. 25, No. 17 3389-3402.
Ausubel et al., "Current protocols in molecular biology, vol. 1, cap. 2—Preparation and analysis of DNA. Phenol extraction and ethanol precipitation of DNA." by John Wiley & Sons, Inc. 2.1.1-2.1.3 (1995).
Batzer et al., "Enhanced evolutionary PCR using oligonucleotides with inosine at the 3'-terminus", Nucleic Acids Res. Sep. 26, 1991; 19(18): 5081.
Baeuerle et al., "Bispecific T-Cell Engaging Antibodies for Cancer Therapy", Cancer Res (2009), vol. 69, pp. 4941-4944.
Brochet et al., "IMGT/V-QUEST: the highly customized and integrated system for IG and TR standardized V-J and V-D-J sequence analysis," Nucl. Acids Res, 36, W503-508, 2008.
Chothia et al., "Canonical structures for the hypervariable regions of immunoglobulins", Journal of Molecular Biology, vol. 196, Issue 4, Aug. 20, 1987, pp. 901-917.
Chothia et al., "Structural repertoire of the human VH segments", Journal of Molecular Biology, vol. 227, Issue 3, Oct. 5, 1992, pp. 799-817.
Chothia et al., "Conformations of immunoglobulin hypervariable regions", Nature, vol. 342, pp. 877-883, Dec. 1989.
Cole et al., "Monoclonal Antibodies and Cancer Therapy", pp. 77-96. Alan R. Liss, Inc., 1985.
Galati et al., "Increased Resistance of Peptides to Serum Proteases by Modification of their Amino Groups", Z. Naturforsch, 58 c, pp. 558-561, 2003.
Giudicelli et al., "IMGT/LIGM-DB, the IMGT® comprehensive database of immunoglobulin and T cell receptor nucleotide sequences", Nucleic Acids Research, 2006, vol. 34, pp. D781-D784.
Harlow and Lane, "Using Antibodies", A Laboratory Manual, 1998, Cold Spring Harbo Laboratory, USA.
Haurum JS, "Recombinant polyclonal antibodies: the next generation of antibody therapeutics?", Drug Discovery Today, vol. 11, Nos. 13/14, Jul. 2006.
Henikoff et al., "Amino acid substitution matrices from protein blocks", Proc. Natl, Acad. Sci. USA, vol. 89, pp. 10915-10919, Nov. 1992.
International Search Report and Written Opinion dated Aug. 1, 2014 in Application No. PCT/US14/22782.
Issekutz et al. "Coexpression of Chemokine Receptors CCR5, CXCR3, and CCR4 and Ligands for P- and E-Selectin on T Lymphocytes of Patients With Juvenile Idiopathic Arthritis", Arthritis & Rheumatism, Nov. 2011, vol. 63, No. 11, pp. 3467-3476.
Janeway et al., Immunobiology, 5$^{th}$ Ed., Garland Science, pp, 94-105 (2001).
Jones et al., "Replacing the complementarity-determining regions in a human antibody with those from a mouse", Nature, vol. 321, pp. 522-525, May 29, 1986.
Kabat et al., "Sequences of Proteins of Immunological Interest", 5th ed., NIH Publication No. 91-3242, 1991.
Karlin et al., "Applications and statistics for multiple high-scoring segments in molecular sequences", Proc. Natl. Acad. Sci. USA, vol. 90, pp. 5873-5877, Jun. 1993.

Köhler et al., "Continuous cultures of fused cells secreting antibody of predefined specificity", Nature, vol. 256, Issue 5517, pp. 495-497 (1975).
Kozbor et al., "The production of monoclonal antibodies from human lymphocytes", Immunology Today, vol. 4, Issue 3, Mar. 1983, pp. 72-79.
Kuby, "Immunology", 4th ed., Chapter 4. W.H. Freeman & Co., New York, 2000.
Lefranc et al., "IMGT unique numbering for immunoglobulin and T cell receptor variable domains and Ig superfamily V-like domains", Developmental & Comparative Immunology, vol. 27, Issue 1, Jan. 2003, pp. 55-77.
MacCallum et al., "Antibody-antigen Interactions: Contact Analysis and Binding Site Topography", Journal of Molecular Biology, vol. 262, Issue 5, Oct. 11, 1996, pp. 732-745.
Marks et al., "By-Passing Immunization: Building High Affinity Human Antibodies by Chain Shuffling", Nature Biotechnology 10, 779-783 (1992).
Martin et al., "Modeling antibody hypervariable loops: A combined algorithm", Proc. Natl. Acad. Sci. USA, vol. 86, pp. 9268-9272, Dec. 1989.
Martin, A., "Chapter 3—Protein Sequence and Structure Analysis of Antibody Variable Domains", Antibody Engineering vol. 2 (2010), pp. 33-51.
McCafferty et al., "Phage antibodies: filamentous phage displaying antibody variable domains", Nature 348, pp. 562-554, Dec. 6, 1990.
Needleman et al., "A general method applicable to the search for similarities in the amino acid sequence of two proteins", Journal of Molecular Biology, vol. 48, Issue 3, Mar. 28, 1970, pp. 443-453.
Office Action dated Jul. 24, 2015 in U.S. Appl. No. 14/202,999.
Office Action dated Mar. 7, 2016 in U.S. Appl. No. 14/202,999.
Ohtsuka et al., "An Alternative Approach to Deoxyoligonucleotides as Hybridization Probes by Insertion of Deoxyinosine at Ambiguous Codon Positions", J. Biol. Chem., vol. 260, No. 5, Issue of Mar. 10, pp. 2605-2608 1985.
Olafsen et al., "Chapter 6—Generation of Single-Chain Fv Fragments and Multivalent Derivatives scFv-Fc and scFv-CH3 (Minibodies)", Antibody Engineering vol. 2 (2010), pp. 69-84.
Paul, Fundamental Immunology, 3d ed. (1993), Raven Press, Ltd. New York.
Pearson et al., "Improved tools for biological sequence comparison", Proc. Nat'l. Acad. Sci. USA, vol. 85, pp. 2444-2448, Apr. 1988.
Presta, "Antibody engineering", Current Opinion in Biotechnology, vol. 3, Issue 4, Aug. 1992, pp. 394-398.
Remington, "The Science and Practice of Pharmacy 21st Edition", Pharmaceutical Press, London, Reprinted 2011, Copyrights 1889-2006.
Riechmann et al., "Reshaping human antibodies for therapy", Nature, vol. 332, pp. 323-327, Mar. 1988.
Rossolini et al., "Use of deoxyinosine-containing primers vs degenerate primers for polymerase chain reaction based on ambiguous sequence information", Molecular and Cellular Probes, vol. 8, Issue 2, Apr. 1994, pp. 91-98.
Sharon et al., "Recombinant polyclonal antibodies for cancer therapy",J Cell Biochem., Oct. 1, 2005, Vol, 96, No. 2, pp. 305-313.
Smith and Waterman, "Comparison of Biosequences", Adv. Appl. Math., 2, pp. 482-489, 1981.
Tavare, "Engineered Anti-Murine CD8 Minibody Fragment for Cu-64 ImmunoPET Imaging of CD8 Expression in Vivo", IBC's 23$^{rd}$ Annual International Conference, Diagnostic Antibody Engineering, Abstract No. F3. 02-06, Dec. 2012, San Diego, CA.
Vajdos et al., "Comprehensive Functional Maps of the Antigen-binding Site of an Anti-ErbB2 Antibody Obtained with Shotgun Scanning Mutagenesis", J. Mol. Biol. (2002), vol. 320, pp. 415-428.
Verhoeyen et al., Reshaping Human Antibodies: Grafting an Antilysozyme Activity, Science, 239:1534-1536, 1988.
Wahlin et al., "CD8+T-Cell Content in Diagnostic Lymph Nodes Measured by Flow Cytometry Is a Predictor of Survival in Follicular Lymphoma", Clin Cancer Res (2007), vol. 13, No. 2.
Wang, S., "Advances in the production of human monoclonal antibodies", Antibody Technology Journal, vol. 1, pp. 1-4, 2011.

(56) References Cited

OTHER PUBLICATIONS

Wu et al., "An analysis of the sequences of the variable regions of Bence Jones proteins and myeloma light chains and their implications for antibody complementarity", J. Exp. Med. vol. 132, pp. 211-250, 1970.
Zhou et al., "T-cell receptor gene transfer exclusively to human CD8+cells enhances tumor cell killing", Blood, Nov. 22, 2012, vol. 120, No. 22.
Extended European Search Report issued in EP Application No. 14779573.6, in 12 pages, dated Aug. 1, 2016.
Office Action issued in U.S. Appl. No. 15/230,085, in 21 pages, dated Mar. 29, 2017.
Olafsen, T. et al., "Development and clinical translation of 89Zr-Df-IAB22M2C for detecting CD8+T Cells for immunotherapy applications," Abstract # 442 presented at the 31$^{st}$ Annual Meeting and Associated Programs of the Society of Immunotherapy of Cancer (SITC 2016), the abstract and corresponding poster are provided in 13 pages. Nov. 11-13, 2016.
Olafsen, T. et al., "Pet imaging of cytotoxic human T cells using an 89Zr-labeled anti-CD8 minibody," Abstract # P338 presented at the 30$^{th}$ Annual Meeting and Associated Programs of the Society for Immunotherapy of Cancer (SITC 2015), the abstract and corresponding poster are provided in 12 pages. Nov. 4-8, 2015.
Office Action dated Mar. 15, 2017 in Chinese Patent App. No. 201480024657X, with English translation.
Office Action dated Mar. 29, 2017 in U.S. Appl. No. 15/230,085.
Almagro, Juan Carlos et al., "Humanization of antibodies", Frontiers in Bioscience 13, Jan. 1, 2008, pp. 1619-1633.
Office Action dated Jan. 4, 2018 in Australian App. No. 2014249243.
Olafsen et al., "Antibody Vectors for Imaging." Seminars in Nuclear Medicine, Mar. 27, 2010, pp. 167-181 vol. 40., No. 3, Grune and Stratton, Orlando, FL, USA.
Office Action dated Dec. 13, 2017 in European App. No. 14 779 573.6.
Office Action dated Feb. 23, 2018 in Chinese Patent App. No. 201480024657X, with English translation.
Office Action dated Feb. 6, 2018 in Japanese Patent App. No. 2016-501063, with English translation.
Office Action dated Nov. 1, 2017 in U.S. Appl. No. 15/230,085.
Office Action dated Nov. 1, 2017 in U.S. Appl. No. 14/407,440.
Office Action dated Mar. 9, 2017 in U.S. Appl. No. 14/407,440.
Office Action dated Sep. 14, 2016 in U.S. Appl. No. 14/407,440.
Office Action dated Feb. 22, 2016 in U.S. Appl. No. 14/407,440.
Office Action dated Jul. 28, 2015 in U.S. Appl. No. 14/407,440.
Office Action dated Mar. 13, 2018 in U.S. Appl. No. 14/407,440.
Final Office Action dated Aug. 1, 2018 in U.S. Appl. No. 14/407,440.
Notice of Allowance dated Jun. 25, 2018 in U.S. Appl. No. 15/230,085.
File History of U.S. Appl. No. 12/483,300.
File History of U.S. Appl. No. 14/419,225.
Hu et al., "Minibody: A novel engineered anti-carcinoembryonic antigen antibody fragment (Single-Chain Fv-CH3) which exhibits rapid, high-level targeting of xenografts1", Cancer Research, vol. 56, pp. 3055-3061 (Jul. 1, 1996).
Leyton et al., "Humanized radioiodinated minibody for imaging of prostate stem cell antigen-expressing tumors", Clinical Cancer Research, vol. 14 No. 22, pp. 7488-7496 (Nov. 15, 2008).
Massoud T. et al. Molecular Imaging In Living Subjects: Seeing Findamental Biological Processes in a New Light, Genes Dev, vol. 17, No. 5, pp. 545-580, (2003).
Olafsen et al., "Characterization of engineered anti-p185 HER-2 (scFv-CH3)2 antibody fragments (minibodies) for tumor targeting", Protein Engineering, Design & Selection, vol. 17 No. 4, pp. 315-323, Oxford University Press (2004).
Radu, C. et al, Positron emission tomography with computed tomography imaing of neuroinflammation in experimental autoimmune encephalomyelitis., Proc Natl Acad Sci USA, vol. 103, No. 6, pp. 1937-1942, (2007).

Radu, C. et al, Molecular imaging of lymphoid organs and immune activation by positron emission tomography with a new [18F]-labeled 2'-deoxycytidine analog, Nat Med, vol. 14, No. 7, pp. 783-780, (2003).
Tumeh, P. et al., PET imaging of Cancer Immunotherapy, I. Uncl Med, vol. 49, No. 6, pp. 865-868, (2008).
Wong et al., "pilot trial evaluation an 123I-Labeled 80-Kilodalton engineered anticarcinoembryonic antigen antibody fragment (cT84.66 minibody) in patients with colorectal cancer", Clinical Cancer Research, vol. 10, pp. 5014-5021 (Aug. 1, 2004).
Wu et al, "Antibodies for molecular imaging of cancer", The Cancer Journal, vol. 14 No. 3, pp. 191-197 (May/Jun. 2008).
Knappik, et al. "Fully synthetic human combinatorial antibody libraries (HuCAL) based on modular consensus frameworks and CDRs randomized with trinucleotides", J.Mol. Biol., vol. 296, Issue 1, pp. 57-86 (2000).
Office Action dated Sep. 4, 2018 in Japanese Patent Application No. 2016-20163; 7 pages.
Office Action dated Sep. 18, 2018 in European Patent Application No. 14 779 573.6; 5 pages.
Office Action dated Oct. 9, 2018 in Chinese Patent Application No. 201480024657X; 14 pages.
Recombinant Anti—CD8 Antibody scFV Fragment <https://www.creativebiolabs.net/anti-cd8-antibody-scfv-fragment-81105.htm>Reference does not have a publication date, however, as this item refers to a webpage, it may haev been available in some form at an earlier date; first accessed on Jan. 14, 2019, archived version on wayback machine not available yet, with data sheet.
Notice of Allowance dated Jan 3, 2019 in U.S. Appl. No. 14/407,440.
Aarntzen E.H. et al., Early identification of antigen-specific immune responses in vivo by [18F]-labeled 3'-fluoro-3'-deoxy-thymidine ([18F]FLT) PET imaging. Proc Natl Acad Sci US A. Nov. 8, 2011;108 (45):18396-1839.
Ali, N., Flutter, B., Sanchez Rodriguez, R., Sharif-Paghaleh, E., Barber, L. D., Lombardi, G., & Nestle, F. O. (2012). Xenogeneic graft-versus-host-disease in NOD-scid |L2Rgammanull mice display a T-effector memory phenotype. PLoS One, 7(8), e44219. doi:10.1371/journal.pone.0044219.
Basu S. et al., Positron emission tomography as a diagnostic tool in infection: present and futrue possibilities. Semin Nucl Med. Jan 2009;39(1):36-51.
Moerman and Oyen, Immuno-PET of Cancre: A Revival of Antibody Imaging, J. Nucl Med. 52(8) 1171-2.) , 2011.
Brahmer, J. et al., (2012). Safety and activity of anti-PD-L1 antibody in patients with advanced cancer. N Engl J Med, 366(26), 2455-2465. doi:10.1056/NEJMoa1200694.
Brezski et al., The in vitro resistance of IgG2 to proteolytic attack concurs with a comparative paucity of autoantibodies against peptide analogs of the IgG2 hinge. MAbs. 3: 558-567, 2011.
Hoffman et al., Simple and rapid measurement of human T lymphocytes and their subclasses in peripheral blood. Proc Natl Acad Sci U S A, 77: 4914-7, 1980.
Clemente CG, Mihm MC Jr, Bufalino R, Zurrida A, Collini P, Cascinelli N. Prognostic value of tumor infiltrating lymphocytes in the vertical growth phase of primay cutaneous melanoma. Cancer 1996;77:1303-1310.
Devine, I., & kavathas, P. B. (1999). Molecular analysis of protein interactions mediating the function of the cell surface protein CD8. Immunol Res, 19(2-3), 201-210. doi:10.1007/bf02786488.
Eisenhauer, E. A., et al. (2009). New response evaluation criteria in solid tumours: revised RECIST guideline (version 1.1). Eur J Cancer, 45(2), 228-247. doi:1.1016/j.ejca. 2008.10.026.
Elzinga E.H. et al., 2-Deoxy-2-[F—18]fluoro-D-glucose joint uptake on positron emission tomography images: rheumatoid arthritis versus osteoarthritis. Mal Imaging Biol. Nov.-Dec. 2007;9(6):357-360.
Feng Z., et al.. Multispectral imaging of formalin fixed tissue predicts ability to generate tumor-infiltration lymphocytes from melanoma. Journal for Immunotherapy of Cancer (2015) 3: 47, doi: 10.1186/s40425-015-0091-z.
Fukunaga A, Miyamoto M, Cho Y, Murakami S, Kawarada Y, Oshikiri T, et al. (2004) CD8+ tumore-infiltrating lumphocytes

(56) References Cited

OTHER PUBLICATIONS together with CD4+ tumor-infiltrating lymphocytes and dendritic cells improve the prognosis of patients with pancreatic adenocarcinoma. Pancreas 28:e26-e31.

Galon J, Costes A, Sanchez-Cabo F, Kirilovsky A, Mlecnik B, Lagorce-Pagès C, et al. Type, density and location of immune cells within human colorectal tumors predict clinical outcome. Science 2006;313:1960-1964.

Garon E.B., Rizvi N.A., Hui R., Leighl N., Balmanoukian A.S., Eder J.P. Gandhi, L. et al. Pembroilizumab for the Treatment of Non-Small-Cell Lunch Cancer. N Engl J Med, 372(21), 2018-28.

Hamanishi J, Mandai M, Iwasaki M, Okazaki T, Tanaka Y, Yamaguchi K, et al. Programmed cell death 1 ligand 1 and tumor-infiltrating CD8+ T lymphocytes are prognostic factors of human ovarian cancer. Proc. Natl Acad. Sci. USA 2007;104:3360-3365.

Sharif-Paghaleh E. et al., in vivo SPECT reporter gene imaging of regulatory T cells PLoS One 2011;6(10):e25857.

Hiraoka N, Onozato K, Kosuge T, Hirohashi S. Prevalence of FOX3+ regulatory T cells increases during the progression of pancreatic ductal adenocarcinoma and its premalignant lesions. Clin Cancer Res. 2006:12:5423-5434.

Hodi, F. S., O'Day, S. J., McDermott, D. F., Weber, R. W., Sosman, J. A., Haanen, J. B., . . . Urba, W. J. (2010). Improved survival with ipilimumab in patients with metastic melanoma. N Engl J Med, 363(8), 711-723.doi:10.1056/NEJMoa1003466.

International Search Report dated Oct. 14, 2013 in International Application No. PCT/US2013/053862.

Jochems, C. & Schlom, J. (2011). Tumor-infiltrating immune cells and prognosis: the potential link between conventional cancer therapy and immunity. Exp Biol Med (Maywood), 236(5), 567-579.

Juweid M.E.et al., Positron-emission tomography and assessment of cancer therapy. N Engl J Med. Feb. 2, 2006;354(5):496-507.

Karja V, Aaltomaa S, Lipponen P, Isotalo P, Talja M, Mokka R, et al. Tumour-infiltrating lymphocytes: a prognostic factor of PSA-free survival in patients with local prostate carcinoma treated by radical prostatectomy. Anticancer Res. 2005;25:4435-4438.

Knowles S.M. et al., Advances in immuno-positron emission tomography: antibodies for molecular imaging in oncology. J. Clin Oneal. Nov. 1, 2012;30(31):3884-3892.

Koya R.C. et al., Kinetic phases of distribution and tumor targeting by T cell receptor engineered lymphocytes inducing robust antitumor responses. Proc Natl Acad Sci USA. Aug. 10, 2010;107(32):14286-14291.

Laing R.E. et al., Visualizing cancer and immune cell function with metabolic positron emission tomography. Curr Opin Genet Dev. Feb. 2010;20(1):100-105.

Liu S, Lachapelle J, Leung S, Gao D, Foulkes WD, Nieslon TO. CD8+ lymphocyte infiltration is an independent favorable prognostic indicator in basal-like breast cancer. Breast Cancer Res. 2012. Mar. 15;14(2):.

Mackensen A. Ferradini L. Carcelain G, Triebel F, Faure F. Evidence for in situ amplification of cytotoxic T-lymphocytes with antitumor activity in a human regressive melanoma. Cancer Res. 1993;53:3569-3573.

Mahmoud, S. M., Palsh, E. C., Powe, D. G., Macmillan, R. D., Grainge, M. J., Lee, A. H., Ellis, I. O. & Green, A. R. (2011). Tumor-infiltrating CD8+ lymphocytes predict clinical outcome in breast cancer. J Clin Oncol., 29(15), 1949-1955.

Mahmoud S, Lee A, Ellis IGreen A. CD8+ T lymphocytes infiltrating breast cancer: A promising new prognostic marker? Oncoimmunology. 2012. May 1; 1(3):364-365.

Malviya, et al Targeting T and B lymphocytes with radiolabelled antibodies for diagnostic and herapeutic applications, Journal of Nuclear Medicine and Molecular Imagining, (2014).

Mamede M. et al., Differential uptake of (18)F-fluorodeoxyglucose by experimental tumors xenografted into immunocompetent and immunodeficient mice and the effect of immunomodification. Neoplasia. Mar.-Apr. 2003;5(2): 179-183.

Matsui K. et al., Quantitation anf visualization of tumor-specific cells in the secondary lymphoid organs during and after tumor elimination by PET. Nucl Med Biol. Nov. 2004;31(8): 1021-1031.

McCracken et al. Advances in PET Detection of the Antitumor T Cell Response, Adv Immunol vol. 131, (2016).

Mellman, I., Coukos, G., & Dranoff, G. (2011). Cancer immunotherapy comes of age. Nature, 480(7378), 480-489. doi:10.1038/nature10673.

Mlecnik B, Tosolini M, Kirilovsky A, Berger A, Bindea G, Meatchi T, et al. Histopathologic-based prognostic factors of colorectal cancers are associated with the state of the local immune reaction. J Clin Oncol. Feb. 20, 2011;29(6).

Moebius, U., Kober, G., Griscelli, A. L., Hercend, T. & Meuer, S. C. (1991). Expression of different CD8 isoforms on distinct human lymphocytes subpopulations. Eur J Immunol, 21(8), 1793-1800. doi:10.1002/eji.1830210803.

Nair-gill E.D.at al., Non-invasive imaging of adaptive immunity using positron emission tomography. Immunol Rev. Feb. 2008;221:214-228;.

Nair-Gill E. et al., PET probes for distinct metabolic pathways have different cell specificities during immune responses in mice. J Clin Invest. Jun. 2010;120(6):2005-2015.

Nakano O, Sato M, Naito Y, Suzuki K, Orikasa S, Aizawa M, et al. Proliferative activity of intratumoral CD8(+) T-lymphocytes as a prognostic factor in human renal cell carcinoma: Clinicopathologic demonstration of antitumor immunity. Cancer Res. 2001;61:5132-5136.

Nakakubo Y, Miyamoto M, Cho Y, Hida Y, Oshikiri T, Suzuoki M, et al. Clinical significance of immune cell infiltration within gallbladder cancer. Br. J. Cancer 2003;89:1736-1742.

Olafsen Tove et al. Recombinant anti-CD20 antibody fragments for microPET imaging ofB-cell lymphoma. J Nucl Med., 2009, 50(9), p. 1500-1508.

Olafsen T. et al., Antibody vectors for imaging. Semin Nucl Med. May 2010;40(3): 167-181.

Pagès F, Kirilovsky A, Mlecnik B, Asslaber M, Tosolini, Bindea G, et al. In situ cytotoxic and memory T cells predict outcome in patients with early-stage colorectal cancer. J Clin Oncol 2009;27:5944-5951.

Pardoll, D., & Drake, C. (2012). Immunotherapy earns its spot in the ranks of cancer therapy. J Exp Med, 209(2), 201-209. doi:10.1084/jem.20112275.

Park, IJ, et al. Prediction of radio-responsiveness with immune-profiling in patients with rectal cancer, Oncotarget. 8:79793-79802, (2017).

Perk, L. R., Visser, O. J., Stigler-van Walsum, M., Vosjan, M. J., Visser, G. W., Zijlstra, J.M., et al. (2006). Preparation and evaluation of (89)Zr-Zevalin for monitoring of (90)Y-Zevalin biodistribution with positron emission tomograpgy. European Journal of Nuclear Medicine and Molecular Imaging, 33, 1337.

Pillay V. et al., Antibodies in oncology. N Bioteehnol. Sep. 2011;28(5):518-529.

Pittet M.J. et al., In vivo imaging ofT cell delivery to tumors after adoptive transfer therapy. Proc Natl Acad Sci USA. Jul. 24, 2007;104(30):12457-12461.

Radiosynthesis Database of PET Probes, dated Mar. 31, 2017 accessed on the World Wide Web at < http://www.nirs.qst.go.jp/research/division/mic/db2/>, As this item refers to a webpage, it may have been available in some form at an earlier date.

Randall, K. J., & Pearse, G. (2008). A dual-label technique for the immunohistochemical demonstration of T-lymphocyte subsets in formalin-fixed, paraffin-embedded rat lymphoid tissue. Toxicol Pathol, 36(6), 795-804. doi:1.1177/0192623308322311.

Ricahardsen E, Uglehus R.D, Due J, Busch C, Busund L T. The prognostic impact of M-CSF, CSF-1 receptor, CD68 and CD3 in prostate carcinoma. Histopathology 2008;53:30-38.

Rizvi, S. N., Visser, O. J., Vosjan, M. J., van Lingen, A., Hoekstra, O. S., Zijlstra, J. M., et al. (2012). Biodistribution, radiation dosimetry and scouting of 90Y-ibritumomab tiuxetan therapy in pateients with relapsed B-cell non-Hodgkin's lymphoma using 89Zribritumomab tiuxetan and PET. European Journal of NUclear Medicine and Molecular Imaging, 39, 512.

(56) References Cited

OTHER PUBLICATIONS

Robert, C. et al. Wolchok, J. D. (2011). Ipilimumab plus dacarbazine for previously untreated metastic melanoma. N Engl J Med, 364(26), 2517-2526. doi:10.1056/NEJMoa1104621.
Romer, P. et al. (2011). PReculture of PBMCs at high cell density increases sensitivity of T-cell responses, revealing cytokine release by CD28 superagonist TGN1412. Blood, 118(26), 6772-6782. doi:10.1182/blood-2010-12-319780.
Rothe A. et al., Recombinant proteins in rheumatology—recent advances. N Bioteehnol. Sep. 2011;28(5):502-51.
Rudd J.H. et al., Inflammation imaigng in atherosclerosis. Arterioscler Thromb Vase Biol. Jul. 2009;29(7): 1009-1016.
Salgado et al. The evaluation of tumor-infiltrating lymphocytes (TILs) in breast cancer: recommendations by an International TILs Working Group 2014 Annals of Oncology, vol. 26, Issue 2, Feb. 1, 2015. pp. 259-271.
Sato E, Olson SH, Ahn J, Bundy B, NIshikawa H, Qian F, et al. (2005) Intraepithelial CD8+ tumor-infiltrating lymphocytes and a high CD8+/redulatory T cell ratio are associated with favorable prognosis in ovarian cancer. Proc Natl Acad Sci U S A 102:18538-18543.
Sathaliyawala, T., Kubota, M., Yudanin, N., Turner, D., Camp, P., Thome, J.J., . . . Farber, D. L. (2013). Distribution and compartmentalization of human circulating and tissue-resident memory T cell subsets. Immunity, 38(1), 187-197. doi:10.1016/j.immuni.2012.09.020.
Shore, D.A. et al. The cyrstal structure ofCD8a~ in complex with YTS156.7.7 Fab and interaction with other CDS antibodies define the binding mode of CD8a to MHC class I. J Mol Biol, 2008, 384 (5), p. I 190-1202.
Shultz, L. D., Lyons B. L., Burzenski, L. M., Gott, B., Chen, X., Chaleff, S., Kotb, M., Gillies, S. D., King, M., Mangada, J., Greiner, D.L. & Handgretinger, R. (2005). Human lymphooid and myeloid cell development in NOD/LtSz-scid IL2R gamma null mice engrafted with mobilized human hemopoietic stem cells. J Immunol., 174(10), 6477-89.
Sharma, P., Shen, y., Wen, S., Yamada, S., Jungbluth, A. A., Gnjatic, S., Bajorin, D. F., Reuter, V. E., Herr, H., Old, L. J. & Sato, E. (2007). CD8 tumor-infiltrating lymphocytes are predictive of survival in muscle-invasive urothelial carcinoma. Proc Natl Acad Sci U S A, 104(10), 3967-3972.
Sharma, P Wagner K, Wolchok JD, Allison JP, Novel cancer immunotherapy agents with survival benefit: recent successes and next steps. Nat Rev Cancer. Oct. 24, 2011;11 (11):805-12. doi:10.1038/nrc3153.
Stebbings, R., Findlay, L. Edwards, C., Eastwood, D., Bird, C., North, D., Mistry, Y., Dilger, P., Liefooghe, E., Cludts, I., Fox, B., Tarrant, G., Robinson, J., Meager, T., Dolman, C., Thorpe, S. J., Bristow, A., Wadhwa, M., Thorpe, R. & Poole, S. (2007). "Cytokine storm" in the phase I trial of monoclonal antibody TGN1412: better understanding the causes to improve preclinical testing of immunotherapeutics. J Immunol. 179(5), 3325-31.
Stelljes M. et al., Clinical molecular imaging in intestinal graft-versus-host disease: mapping of disease activity, prediction, and monitoring of treatment efiiciency by positron emission tomography. Blood. Mar. 1, 2008;111(5):2909-2918.

Sundaresan Gobalakrishan et al, J-Labeled Engineered Anti-CEA Minibodies and Diabodies Allow High-Contrast, Antigen-Specific Small-Animal PET Imaging ofXenografts in Athymic Mice. The Journal of Nuclear Medicine, 2003, vol. 44, No. 12, pp. 1962-1969.
Tefany FJ, Barnetson RS, Halliday G. M., McCarthy SW, McCarthy WH. Immunocytochemical analysis of the cellular infiltrate in primary regressing and non-regressing malignant melanoma. J. Invest. Dermatol. 1991;97:197-202.
Topalian, S. L., Sznol, M., McDermott, D. F., Kluger, H. M., Carvajal, R. D., Sharfman, W. H., . . . Hodi, F. S. (2014). Survival, durable tumor remission, and long-term safety in patients with advanced melanoma receiving nivolumab. J Clin Oncol, 32(10), 1020-1030. doi:10.1200/jco.2013.53.0105.
Tumeh, p, et al., PD-1 blockade induces responses by inhibiting adaptive immune resistance. Nature, 515(7528), 568-571.
van Oijen M, Bins A, Elias S, Sein J, Weder P, de Gast G, et al. On the rolse of the melanoma-specific CD8+ T-cell immunity in disease progression of advanced-stage melanoma patients. Clin Cancer Res 2004;10:4754-4760.
Westermann, J., & Pabst, R. (1992). Distribution of lymphocyte subsets and natural killer cells in the human body. Clin Investig, 70(7), 539-544.
Williamson, S. et al. . Horne, C. H. (1998). New monoclonal antibodies to the T cell antigens CD4 and CD8. Production and characterization in formalin-fixed paraffin-embedded tissue. Am J Pathol, 152(6), 1421-1426.
Wolchok, J et al. (2009). Guidelines for the evaluation of immune therapy activity in solid tumors: immune-related response criteria. Clin Cancer Res, 15(23), 7412-7420. doi:10.1158/1078-0432.ccr-09-1624.
Wu Anna M. et al. High-resolution microPET imaging of carcinoembryonic antigen-positive xenografts by using a copper-64-labeled engineered antibody fragment. PNAS, 2000, vol. 97, No. 15, oo. 8495-8500.
Wu A.M. et al., Arming antibodies: prospects and challenges for immunoconjugates. Nat Bioteehnol. Sep. 2005;23(9): 1137-1146.
Yaghoubi S.S. et al.,. Positronemission tomograghy reporter genes and reporter probes: gene and cell therapy applications. Theranostics. 2012;2(4):374-3.
Ziai CD8+ cell infiltration in breast and colon cancer: A histologic and statistical analysis, PLoS One, (2018).
Tavaré, R., Witte, o., Ribas, A., Wu, A.M., et al., An Effective immuno-PET Imaging Method to Monitor CD8-Dependent Responses to Immunotherapy Cancer Research 76(1), 73-82, 2016.
Chen et al Analysis of Immune Signatures in Longitudinal Tumor Samples Yields Insight into Biomarkers of Response and Mechanisms of Resistance to Immune Checkpoint Blockade Cancer Discovery Cancer Discov 2016;6:827-837. Published OnlineFirst Jun. 14, 2016.
Olafsen et al. (2010) ImmunoPET imaging of B-cell lymphoma using 124I-anti-CD20 scFv dimers (diabodies), Protein Engineering, Design & Selection, vol. 23, No. 4, pp. 243-249, (2010).
Notice of Allowance dated Mar. 27, 2019 in U.S. Appl. No. 15/230,085.
Office Action dated Apr. 16, 2019 in European App. No. 14 779 573.6.
Office Action dated May 7, 2019 in Japanese Patent Application No. 2016-501063 with English Translation.

* cited by examiner

FIGURE 1C

```
          10         20         30         40         50         60
  MALPVTALLL PLALLLHAAR PSQFRVSPLD RTWNLGETVE LKCQVLLSNP TSGCSWLFQP 70         80         90        100        110        120
  RGAAASPTFL LYLSQNKPKA AEGLDTQRFS GKRLGDTFVL TLSDFRRENE GYYFCSALSN 130        140        150        160        170        180
  SIMYFSHFVP VFLPAKPTTT PAPRPPTPAP TIASQPLSLR PEACRPAAGG AVHTRGLDFA 190        200        210        220        230
  CDIYIWAPLA GTCGVLLLSL VITLYCNHRN RRRVCKCPRP VVKSGDKPSL SARYV    SEQ ID NO: 24
```

```
Humanized VL:            LCDR1                                            LCDR2
muOKT8   DVQINQSPSFLAASPGETITINC RTSRSISQYLA WYQEKPGTNKLLIY SGSTLQS GIPS
            *  **     *  * ***    *                *                 *
Human    DIQMTQSPSSLSASVGDRVTITC RASQGISNYLA WYQQKPGKVPKLLIY AASTLQS GVPS
huOKT8   DVQITQSPSSLSASVGDRVTITC RTSRSISQYLA WYQQKPGKVPKLLIY SGSTLQS GVPS
             _

LCDR3
muOKT8   RFSGSGSGTDFTLTISGLEPEDFAMYYC QQHNENPLT FGAGTKLELK   SEQ ID NO: 7
              *             *  *       *   **
Human    RFSGSGSGTDFTLTISSLQPEDVATYYC QKYNSAPLT FGGGTKVEIK   SEQ ID NO: 8
huOKT8   RFSGSGSGTDFTLTISSLQPEDVATYYC QQHNENPLT FGGGTKVEIK   SEQ ID NO: 9
```

| SS | V$_H$ | L | V$_L$ | GGC |

FIGURE 4

```
tctagagccgccacc  SEQ ID NO: 61
XbaI Kozak
    1   M  E  T  D  T  L  L  L  W  V  L  L  L  W  V  P  G  S  T  G
    1   ATGGAGACAGACACCCTGCTCCTGTGGGTGCTGCTCCTCTGGGTCCCTGGATCCACCGGC
        Signal Peptide
   21   D  V  Q  I  N  Q  S  P  S  F  L  A  A  S  P  G  E  T  I  T
   61   GATGTCCAGATCAACCAAAGCCCCAGCTTTCTGGCTGCCTCCCCTGGAGAGACAATCACC
                    VL
   41   I  N  C  R  T  S  R  S  I  S  Q  Y  L  A  W  Y  Q  E  K  P
  121   ATCAATTGCCGGACCAGCCGGAGCATTTCCCAGTACCTCGCCTGGTACCAGGAAAAGCCT 61   G  K  T  N  K  L  L  I  Y  S  G  S  T  L  Q  S  G  I  P  S
  181   GGCAAGACCAACAAGCTGTTGATCTACTCCGGCTCCACACTCCAGAGCGGCATTCCTTCC 81   R  F  S  G  S  G  S  G  T  D  F  T  L  T  I  S  G  L  E  P
  241   AGGTTTAGCGGATCCGGATCCGGAACCGACTTCACACTCACCATCTCCGGCCTGGAGCCC 101   E  D  F  A  M  Y  Y  C  Q  Q  H  N  E  N  P  L  T  F  G  A
  301   GAGGACTTCGCCATGTATTATTGCCAGCAGCACAATGAGAACCCTCTGACCTTCGGCGCT 121   G  T  K  L  E  L  K  G  S  T  S  G  G  G  S  G  G  S  G
  361   GGCACCAAGCTGGAGCTGAAAGGCTCCACCAGCGGAGGCGGATCCGGAGGAGGCGGC
                                    Linker
  141   G  G  G  S  S  E  V  Q  L  Q  Q  S  G  A  E  L  V  K  P  G
  421   GGCGGAGGCTCCTCCGAAGTGCAGCTGCAACAGAGCGGCGCCGAACTGGTGAAGCCTGGA
                            VH
  161   A  S  V  K  L  S  C  T  A  S  G  F  N  I  K  D  T  Y  I  H
  481   GCTTCCGTGAAACTGAGCTGTACCGCCAGCGGCTTCAACATCAAGGATACCTACATCCAC 181   F  V  R  Q  R  P  E  Q  G  L  E  W  I  G  R  I  D  P  A  N
  541   TTCGTGCGGCAAAGGCCTGAGCAGGGCCTGGAATGGATCGGCAGGATCGACCCCGCCAAC 201   D  N  T  L  Y  A  S  K  F  Q  G  K  A  T  I  T  A  D  T  S
  601   GACAACACCCTCTACGCCTCCAAGTTCCAAGGCAAGGCCACAATCACCGCTGATACAAGC 221   S  N  T  A  Y  M  R  L  S  S  L  T  S  G  D  T  A  V  Y  Y
  661   TCCAACACCGCCTACATGCACCTCAGCTCCCTGACCAGCGGAGACACCGCCGTGTACTAC 241   C  G  R  G  Y  G  Y  Y  V  F  D  H  W  G  Q  G  T  T  L  T
  721   TGCGGACGGGGATACGGCTACTATGTGTTCGACCACTGGGGCCAAGGCACCACACTCACC 261   V  S  S  E  P  K  S  C  D  K  T  H  T  C  P  P  C  G  G
  781   GTGTCCTCCGAGCCCAAGTCCTGCGACAAGACACACACCTGTCCCCCTTGTGGAGGAGGA
               Hinge/Extension
  281   S  S  G  G  S  G  Q  P  R  E  P  Q  V  Y  T  L  P  P
  841   TCCTCCGGAGGCGGTCCGGCCAGCCTAGGGAGCCCCAGGTGTACACACTGCCCCCT
                              CH3
  301   S  R  D  E  L  T  K  N  Q  V  S  L  T  C  L  V  K  G  F  Y
  901   TCCAGGGACGAACTCACCAAGAACCAGGTGTCCCTGACCTCCTGGTGAAGGGATTCTAC 321   P  S  D  I  A  V  E  W  E  S  N  G  Q  P  E  N  N  Y  K  T
  961   CCCAGCGATATCGCCGTGGAGTGGGAGTCCAACGGCCAACCGGAGAACAATACAAGACC 341   T  P  P  V  L  D  S  D  G  S  F  F  L  Y  S  K  L  T  V  D
 1021   ACCCCCCCTGTGCTCGATTCCGACGGCTCCTTCTTCCTGTACTCCAAGCTCACCGTGGAC 361   K  S  R  W  Q  Q  G  N  V  F  S  C  S  V  M  H  E  A  L  H
 1081   AAGTCCCGGTGGCAACAGGGCAATGTGTTCTCCTGCAGCGTCATGCACGAGGCCCTGCAT

381   N  H  Y  T  Q  K  S  L  S  L  S  P  G  K  -   SEQ ID NO: 16

1141   AACCACTACACCCAGAAATCCCTCAGCCTGTCCCCTGGAAAATGA   SEQ ID NO: 17
        aagctt  SEQ ID NO: 64   HinDIII
```

FIGURE 5

```
TCTAGAGCCGCCACC  SEQ ID NO:62
XbaI   Kozak

1   M  E  T  D  T  L  L  L  W  V  L  L  L  W  V  P  G  S  T  G
  1   ATGGAGACCGACACACTCCTGCTCTGGGTGCTCCTGCTGTGGGTGCCTGGCAGCACAGGA
      Signal Peptide
 21   E  V  Q  L  Q  Q  S  G  A  E  L  V  K  P  G  A  S  V  K  L
 61   GAAGTGCAGCTGCAGCAGTCCGGCGTCGAACTCGTCAAACCCGGAGCCTCCGTCAAACTG
      VH
 41   S  C  T  A  S  G  F  N  I  K  D  T  Y  I  H  F  V  R  Q  R
121   TCCTGCACAGCCAGCGGCTTCAACATCAAGGACACCTACATCCATTTCGTGCGGCAAAGG
 61   P  E  Q  G  L  E  W  I  G  R  I  D  P  A  N  D  N  T  L  Y
181   CCTGAACAGGGACTCGAGTGGATCGGCAGGATCGACCCCGCCAACGACAATACCCTCTAC
 81   A  S  K  F  Q  G  K  A  T  I  T  A  D  T  S  S  N  T  A  Y
241   GCCTCCAAGTTCCAGGGAAAGGCCACCATTACCGCCGACACATCCAGCAACACCGCCTAC
101   M  H  L  S  S  L  T  S  G  D  T  A  V  Y  Y  C  G  R  G  Y
301   ATGCACCTCAGCTCCCTGACATCCGGCGACACCGCCGTGTACTACTGCGGCAGGGGCTAC
121   G  Y  Y  V  F  D  R  W  G  Q  G  T  T  L  T  V  S  S  G  S
361   GGCTACTACGTGTTTGACCGCTGGGGCCAGGGAACAACCCTGACCGTGTCCAGCGGCTCC
                                                           Linker
141   T  S  G  G  S  G  G  G  S  G  G  G  S  S  D  V  Q  I
421   ACCTCCGGAGGCGGAAGCGGCGGAGGATCCGGAGGAGGAGGCTCCTCCGACGTGCAAATC
                                                             VL
161   N  Q  S  P  S  F  L  A  A  S  P  G  E  T  I  T  I  N  C  R
481   AACCAGTCCCCTAGCTTCCTGGCCGCTAGCCCTGGCGAGACAATCACAATCAATTGTCGG
181   T  S  R  S  I  S  Q  Y  L  A  W  Y  Q  E  K  P  G  K  T  N
541   ACCAGCCGGTCCATCTCCCAGTATCTGGCCTGGTACCAGGAGAAGCCCGGCAAGACAAAC
201   K  L  L  I  Y  S  G  S  T  L  Q  S  G  I  P  S  R  F  S  G
601   AAGCTGCTCATCTACAGCGGCAGCACCCTCCAATCGGGCATCCCTTCCCGGTTCAGCGGC
221   S  G  S  G  T  D  F  T  L  T  I  S  G  L  E  P  E  D  F  A
661   TCCGGATCCGGAACCGACTTTACCCTGACCATCAGCGGCCTGGAACCCGAGGATTTCGCC
241   M  Y  Y  C  Q  Q  H  N  E  N  P  L  T  F  G  A  G  T  K  L
721   ATGTACTACTGCCAGCAGCACAACGAGAATCCCCTGACCTTTGGAGCCGGCACAAAGCTC
261   E  L  K  E  P  K  S  C  D  K  T  H  T  C  P  P  C  G  G  G
781   GAGCTGAAGGAGCCCAAGAGCTGCGACAAAACCCACACCTGTCCCCCTTGCGGAGGAGGA
               Hinge/Extension
281   S  S  G  G  S  G  G  Q  P  R  E  P  Q  V  Y  T  L  P  P
841   TCCTCCGGCGGCGGAAGCGGAGGACAACCCAGGGAGCCCCAGGTCTACACCCTGCCTCCT
                                                     CH3
301   S  R  D  E  L  T  K  N  Q  V  S  L  T  C  L  V  K  G  F  Y
901   AGCCGGGACGAACTGACAAAGAACCAGGTGTCCCTGACCTGTCTCGTCAAGGGCTTCTAC
321   P  S  D  I  A  V  E  W  E  S  N  G  Q  P  E  N  N  Y  K  T
961   CCTTCCGACATCGCCGTCGAGTGGGAAAGCAACGGCCAGCCCGAGAACAATTACAAGACC
341   T  P  P  V  L  D  S  D  G  S  F  F  L  Y  S  K  L  T  V  D
1021  ACACCCCCGTCCTGGACAGCGATGGCAGCTTCTTCCTCTACTCCAAGCTGACCGTGGAC
361   K  S  R  W  Q  Q  G  N  V  F  S  C  S  V  M  H  E  A  L  H
1081  AAGAGCCGGTGGCAACAAGGCAACGTGTTCTCCTGCAGCGTCATGCATGAGGCCCTGCAC
381   N  H  Y  T  Q  K  S  L  S  L  S  P  G  K  -   SEQ ID NO: 18
1141  AATCACTACACCCAGAAGAGCCTGAGCCTCTCCCCGGCAAGTGA  SEQ ID NO: 19
                                               Stop
AAGCTT SEQ ID NO: 63   HinDIII
```

FIGURE 6

Tctagagcogccacc  SEQ ID NO: 65

XbaI Kozak

```
  1    M  E  T  D  T  L  L  L  W  V  L  L  L  W  V  P  G  S  T  G
  1    ATGGAGACAGACACCCTCCTGCTGTGGGTCCTGCTGCTGTGGGTGCCTGGCAGCACAGGA
       Signal Peptide
 21    D  I  Q  M  T  Q  S  P  S  S  L  S  A  S  V  G  D  R  V  T
 61    GACATCCAAATGACCCAGTCCCCTAGCAGCCTCAGCGCTTCCGTCGGAGACAGGGTCACC
       VL
 41    I  T  C  R  T  S  R  S  I  S  Q  Y  L  A  W  Y  Q  Q  K  P
121    ATCACATGCAGGACCTCCAGGTCCATCAGCCAGTATCTGGCCTGGTATCAGCAGAAACCC
 61    G  K  V  P  K  L  L  I  Y  S  G  S  T  L  Q  S  G  V  P  S
181    GGCAAGGTGCCTAAGCTGCTGATCTACAGCGGCAGCACACTCCAGAGCGGAGTGCCCAGC
 81    R  F  S  G  S  G  S  G  T  D  F  T  L  T  I  S  S  L  Q  P
241    CGGTTTTCCGGAAGCGGATCCGGAACCGACTTCACCCTGACCATTTCCAGCCTGCAACCT
101    E  D  V  A  T  Y  Y  C  Q  Q  H  N  E  N  P  L  T  F  G  G
301    GAAGACGTGGCCACCTACTACTGTCAGCAGCACAACGAGAACCCCCTCACCTTCGGCGGA
121    G  T  K  V  E  I  K  G  S  T  S  G  G  G  S  G  G  G  S  G
361    GGCACCAAAGTCGAGATCAAGGGCAGCACCAGCGGAGGAGGAAGCGGCGGAGGCTCCGGA
                                              Linker
141    G  G  G  S  S  Q  V  Q  L  V  Q  S  G  A  E  V  K  K  P  G
421    GGAGGAGGCTCCTCCCAAGTGCAGCTCGTCCAAAGCGGCGCTGAGGTGAAAAAGCCCGGC
                                 VH
161    A  T  V  K  I  S  C  K  V  S  G  F  N  I  K  D  T  Y  I  H
481    GCCACAGTCAAAATCTCCTGCAAGGTCAGCGGCTTCAACATCAAGGATACCTACATCCAC
181    W  V  Q  Q  A  P  G  K  G  L  E  W  M  G  R  I  D  P  A  N
541    TGGGTGCAACAGGCCCCCGGCAAAGGACTCGAATGGATGGGCCGGATCGACCCTGCTAAC
201    D  N  T  L  Y  A  S  K  F  Q  G  R  V  T  I  T  A  D  T  S
601    GACAACACACTCTACGCCTCCAAGTTCCAGGGCAGGGTGACCATCACCGCCGATACCTCC
221    T  D  T  A  Y  M  E  L  S  S  L  R  S  E  D  T  A  V  Y  Y
661    ACCGACACAGCCTACATGGAGCTGAGCAGCCTGAGGTCCGAGGACACCGCCGTCTATTAC
241    C  A  R  G  Y  G  Y  Y  V  F  D  H  W  G  Q  G  T  L  V  T
721    TGCGCCCGGGGATACGGCTACTACGTGTTTGACCATTGGGGACAGGGAACACTCGTGACC
261    V  S  S  E  P  K  S  C  D  K  T  H  T  C  P  P  C  G  G  G
781    GTGAGCTCCGAGCCCAAGAGCTGCGACAAGACCCACACATGTCCTCCTTGCGGAGGAGGC
                                           Hinge/Extension
281    S  S  G  G  G  S  G  G  Q  P  R  E  P  Q  V  Y  T  L  P  P
841    AGCTCCGGAGGCGGATCCGGCGGACAACCTAGGGAGCCCCAGGTCTATACCCTGCCCCCC
                                          CH3
301    S  R  D  E  L  T  K  N  Q  V  S  L  T  C  L  V  K  G  F  Y
901    AGCAGGGACGAGCTGACAAAGAACCAGGTCTCCCTGACCTGCCTGGTGAAAGGATTCTAC
321    P  S  D  I  A  V  E  W  E  S  N  G  Q  P  E  N  N  Y  K  T
961    CCCAGCGACATCGCTGTCGAATGGGAGTCCAACGGCCAGCCCGAGAACAACTACAAGACA
341    T  P  P  V  L  D  S  D  G  S  F  F  L  Y  S  K  L  T  V  D
1021   ACCCCCCCCGTGCTGGATTCCGACGGCAGCTTCTTCCTCTACTCCAAGCTGACCGTCGAC
361    K  S  R  W  Q  Q  G  N  V  F  S  C  S  V  M  H  E  A  L  H
1081   AAGTCCAGGTGGCAGCAGGGCAACGTGTTTTCCTGCTCCGTGATGCATGAGGCCCTGCAC
381    N  H  Y  T  Q  K  S  L  S  L  S  P  G  K  -         SEQ ID NO: 20
1141   AACCACTACACCCAGAAGTCCCTGAGCCTCAGCCCTGGCAAGTGA        SEQ ID NO: 21
                                                  Stop
``` aagctt  SEQ ID NO: 66  HinDIII

FIGURE 7

```
tctagagcgcacc    SEQ ID NO: 67

Xbal Kozak

1   M   E   T   D   T   L   L   W   V   L   L   L   W   V   P   G   S   T   G
  1   ATGGAGACCGATACACTGCTGCTCTGGGTGCTGCTGCTGTGGGTGCCTGGAAGCACCGGA
      Signal Peptide
 21   Q   V   Q   L   V   Q   S   G   A   E   V   K   K   F   G   A   T   V   K   I
 61   CAGGTGCAACTGGTCCAGTCCGGCGCCGAGGTGAAAAAGCCTGGCGCCACCGTCAAGATC
        VH
 41   S   C   K   V   S   G   F   N   I   K   D   T   Y   I   H   W   V   Q   Q   A
121   TCCTGTAAGGTGAGCGGCTTCAACATCAAGGACACCTACATCCACTGGGTGCAGCAGGCT 61   P   G   K   G   L   E   W   M   G   R   I   D   P   A   N   D   N   T   L   Y
181   CCCGGAAAGGGACTGGAGTGGATGGGCAGGATCGACCCTGCCAATGACAACACCCTCTAC 81   A   S   K   F   Q   G   R   V   T   I   T   A   D   T   S   T   D   T   A   Y
241   GCCAGCAAGTTCCAAGGACGGGTGACCATCACAGCCGACACATCCACCGACACAGCCTAT 101   M   E   L   S   S   L   R   S   E   D   T   A   V   Y   Y   C   A   R   G   Y
301   ATGGAGCTCTCCAGCCTGAGGTCCGAGGACACCGCCGTGTACTACTGTGCCAGGGGATAC 121   G   Y   Y   V   F   D   H   W   G   Q   G   T   L   V   T   V   S   S   G   S
361   GGCTATTACGTGTTCGACCACTGGGGACAGGGCACCCTGGTGACCGTGAGCAGCGGAAGC
                                                                       Linker
141   T   S   G   G   S   G   G   G   S   G   G   G   G   S   D   I   Q   M
421   ACCAGCGGCGGAGGCAGCGGAGGCGGAAGCGGCGGCGGCGGATCCGACATTCAGATG
                                                                       VL
161   T   Q   S   P   S   S   L   S   A   S   V   G   D   R   V   T   I   T   C   R
481   ACCCAATCCCCCTCCAGCCTGTCCGCTAGCGTGGGAGACAGGGTGACAATCACATGTCGG 181   T   S   R   S   I   S   Q   Y   L   A   W   Y   Q   Q   K   F   S   K   V   P
541   ACCTCCAGGTCCATCAGCCAATATCTGGCCTGGTATCAGCAGAAGTTCAGCAAGGTGCCC 201   K   L   L   I   Y   S   G   S   T   L   Q   S   G   V   P   S   R   F   S   G
601   AAGCTCCTGATCTACAGCGGCTCCACCCTCCAAAGCGGAGTGCCTTCCCGGTTTAGCGGA 221   S   G   S   G   T   D   F   T   L   T   I   S   S   L   Q   P   E   D   V   A
661   AGCGGCAGCGGCACAGACTTTACCCTGACAATCAGCTCCCTGCAACCTGAGGACGTCGCC 241   T   Y   Y   C   Q   Q   H   N   E   N   P   L   T   F   G   G   G   T   K   V
721   ACATACTACTGCCAGCAGCACAACGAGAACCCTCTCACCTTTGGCGGCGGCACCAAAGTG 261   E   I   K   E   P   K   S   C   D   K   T   H   T   C   P   P   C   G   G   G
781   GAGATCAAGGAGCCCAAATCCTGCGACAAGACACACACCTGCCCCCCTTGTGGAGGAGGC
      Hinge/Extension
281   S   S   G   G   S   G   G   Q   P   R   E   P   Q   V   Y   T   L   P   P
841   AGCTCCGGCGGCGGCAGTGGCGGACAACCCCGGGAACCTCAGGTGTATACACTCCCCCCT
                                    CH3
301   S   R   D   E   L   T   K   N   Q   V   S   L   T   C   L   V   K   G   F   Y
901   TCCAGGGATGAGCTGACCAAGAACCAAGTCTCCCTGACCTGTCTGGTGAAAGGCTTCTAC 321   P   S   D   I   A   V   E   W   E   S   N   G   Q   P   E   N   N   Y   K   T
961   CCCTCCGACATCGCTGTCGAGTGGGAGAGCAACGGCCAGCCGAAAACAACTATAAGACC 341   T   P   P   V   L   D   S   D   G   S   F   F   L   Y   S   K   L   T   V   D
1021  ACCCCCCCCGTGCTCGATTCCGATGGCAGCTTCTTCCTGTACTCCAAGCTCACAGTCGAC 361   K   S   R   W   Q   Q   G   N   V   F   S   C   S   V   M   H   E   A   L   H
1031  AAGAGCCGGTGGCAACAGGGCAACGTCTTCTCCTGTAGCGTCATGCACGAGGCCCTCCAC 381   N   H   Y   T   Q   K   S   L   S   L   S   P   G   K   -       SEQ ID NO: 22
1141  AACCACTACACCCAGAAGTCCCTCTCCTGAGCCCCGGAAAATGA         SEQ ID NO: 23
                                              Stop
aagctt  SEQ ID NO: 68   HindIII
```

FIGURE 8

Tctagagcggccacc  SEQ ID NO: 69

XbaI Kozak

```
  1   M   E   T   D   L   L   L   W   V   L   L   W   V   P   G   S   T   G
  1   ATGGAGACCGATACACTGCTGCTGTGGGTGCTGCTGCTCTGGGTCCCTGGCAGCACAGGA
      Signal Peptide
 21   D   I   Q   M   T   Q   S   P   S   S   L   S   A   S   V   G   D   R   V   T
 61   GACATCCAGATGACACAGAGCCCTAGCTCCCTGAGCGCTTCCGTGGGAGATAGGGTGACC
      VL
 41   I   T   C   R   T   S   R   S   I   S   Q   Y   L   A   W   Y   Q   Q   K   P
121   ATCACATGCCGGACCTCCAGGTCCATCTCCCAGTACCTGGCCTGGTACCAGCAGAAGCCC 61   G   K   V   P   K   L   L   I   Y   S   G   S   T   L   Q   S   G   V   P   S
181   GGCAAGGTGCCCAAGCTGCTCATCTATAGCGGCAGCACCCTGCAGAGCGGAGTGCCTTCC 81   R   F   S   G   S   G   S   G   T   D   F   T   L   T   I   S   S   L   Q   P
241   CGGTTTTCCGGATCCGGCTCCGGCACAGACTTTACCCTGACCATCTCCAGCCTGCAGCCT 101   E   D   V   A   T   Y   Y   C   Q   Q   H   N   E   N   P   L   T   F   G   G
301   GAGGATGTGGCCACCTACTACTGCCAACAGCACAACGAGAACCCCCTGACCTTCGGCGGC 121   G   T   K   V   E   I   K   S   G   G   G   G   Q   V   Q   L   V   Q   S   G
361   GGAACCAAGGTCGAGATCAAGTCCGGAGGAGGAGGCCAAGTGCAGCTGGTCCAATCCGGC
                                      Linker              VH
141   A   E   V   K   K   P   G   A   T   V   K   I   S   C   K   V   S   G   F   N
421   GCCGAAGTGAAAAAGCCCGGCGCCACCGTGAAGATCAGCTGCAAGGTGTCCGGCTTCAAC 161   I   K   D   T   Y   I   H   W   V   Q   Q   A   P   G   K   G   L   E   W   M
481   ATCAAGGACACCTATATCCACTGGGTCCAGCAAGCCCCCGGAAAAGGCCTGGAGTGGATG 181   G   R   I   D   P   A   N   D   N   T   L   Y   A   S   K   F   Q   G   R   V
541   GGACGGATTGACCCCGCCAACGACAACACACTCTATGCCTCCAAGTTCCAGGGCAGGGTG 201   T   I   T   A   D   T   S   T   D   T   A   Y   M   E   L   S   S   L   R   S
601   ACAATCACCGCCGACACCAGCACCGACACAGCTTATATGGAGCTGTCCTCCCTCCGGTCC 221   E   D   T   A   V   Y   Y   C   A   R   G   Y   G   Y   Y   V   F   D   H   W
661   GAGGATACCGCCGTCTACTACTGCGCCAGGGGCTACGGCTACTACGTGTTTGACCACTGG 241   G   Q   G   T   L   V   T   V   S   S   G   G   C   SEQ ID NO: 12
721   GGCCAGGGCACCCTGGTGACAGTGTCCAGCGGAGGCTGC   SEQ ID NO: 77
                                            Cys
``` aagctt  SEQ ID NO: 70

HinDIII

FIGURE 9 tctagagcgccacc SEQ ID NO: 71

XbaI Kozak

```
  1   M  E  T  D  T  L  L  L  W  V  L  L  L  W  V  P  G  S  T  G
  1   ATGGAGACCGACACCCTGCTGCTCTGGGTCCTCCTGCTGTGGGTGCCTGGCAGCACAGGA
      Signal Peptide
 21   Q  V  Q  L  V  Q  S  G  A  E  V  K  K  P  G  A  T  V  K  I
 61   CAGGTGCAACTGGTGCAGAGCGGCGCCGAGGTCAAGAAACCTGGCGCCACCGTGAAGATC
      VH
 41   S  C  K  V  S  G  F  N  I  K  D  T  Y  I  H  W  V  Q  Q  A
121   AGCTGCAAGGTGTCCGGCTTCAACATCAAGGACACCTACATCCACTGGGTCCAACAAGCC 61   P  G  K  G  L  E  W  M  G  R  I  D  P  A  N  D  N  T  L  Y
181   CCCGGAAAGGGCCTGGAATGGATGGGCCGGATTGACCCTGCCAACGACAACACCCTCTAT 81   A  S  K  F  Q  G  R  V  T  I  T  A  D  T  S  T  D  T  A  Y
241   GCCAGCAAGTTCCAGGGCAGGGTCACCATCACCGCCGACACCAGCACCGACACCGCCTAC 101   M  E  L  S  S  L  R  S  E  D  T  A  V  Y  Y  C  A  R  G  Y
301   ATGGAGCTGAGCAGCCTGCGGAGCGAAGACACCGCCGTGTACTACTGCGCCAGGGGCTAC 121   G  Y  Y  V  F  D  H  W  G  Q  G  T  L  V  T  V  S  S  S  G
361   GGCTACTACGTCTTCGACCATTGGGGACAGGGCACCCTCGTGACAGTGTCCAGCTCCGGC
                                                               Linker
141   G  G  D  I  Q  M  T  Q  S  P  S  S  L  S  A  S  V  G  D
421   GGAGGAGGAGATATCCAGATGACCCAGAGCCCTTCCAGCCTGTCCGCTTCCGTGGGAGAT
                  VL
161   R  V  T  I  T  C  R  T  S  R  S  I  S  Q  Y  L  A  W  Y  Q
481   CGGGTGACCATCACATGCAGGACCTCCAGGTCCATCTCCCAGTACCTGGCCTGGTACCAA 181   Q  K  P  G  K  V  P  K  L  L  I  Y  S  G  S  T  L  Q  S  G
541   CAGAAGCCCGGCAAGGTGCCCAAGCTGCTGATTTACAGCGGCAGCACACTGCAATCCGGC 201   V  P  S  R  F  S  G  S  G  S  G  T  D  F  T  L  T  I  S  S
601   GTCCCTTCCCGGTTTTCCGGATCCGGATCCGGCACCGACTTCACCCTGACCATCAGCTCC 221   L  Q  P  E  D  V  A  T  Y  Y  C  Q  Q  H  N  E  N  P  L  T
661   CTGCAACCCGAGGACGTGGCCACCTACTACTGTCAGCAGCACAACGAGAACCCCCTCACC 241   F  G  G  G  T  K  V  E  I  K  G  G  C    SEQ ID NO: 13
721   TTTGGCGGCGGAACCAAGGTCGAGATCAAGGGCGGCTGC   SEQ ID NO: 78
                                         Cys
``` aagctt SEQ ID NO: 72

HindIII

FIGURE 10

<u>Tctagagccgccacc</u> SEQ ID NO: 73

XbaI Kozak

```
  1   M  E  T  D  T  L  L  W  V  L  L  L  W  V  P  G  S  T  G
  1   ATGGAGACCGATACACTGCTGCTGTGGGTGCTGCTGCTCTGGGTCCCTGGCAGCACAGGA
      Signal Peptide
 21   D  I  Q  M  T  Q  S  P  S  S  L  S  A  S  V  G  D  R  V  T
 61   GACATCCAGATGACACAGAGCCCTAGCTCCCTGAGCGCTTCCGTGGGAGATAGGGTGACC
         VL
 41   I  T  C  R  T  S  R  S  I  S  Q  Y  L  A  W  Y  Q  Q  K  P
121   ATCACATGCCGGACCTCCAGGTCCATCTCCCAGTACCTGGCCTGGTACCAGCAGAAGCCC 61   G  K  V  P  K  L  L  I  Y  S  G  S  T  L  Q  S  G  V  P  S
181   GGCAAGGTGCCCAAGCTGCTCATCTATAGCGGCAGCACCCTGCAGAGCGGAGTGCCTTCC 81   R  F  S  G  S  G  S  G  T  D  F  T  L  T  I  S  S  L  Q  P
241   CGGTTTTCCGGATCCGGCTCCGGCACAGACTTTACCCTGACCATCTCCAGCCTGCAGCCT 101   E  D  V  A  T  Y  Y  C  Q  Q  H  N  E  N  P  L  T  F  G  G
301   GAGGATGTCGCCACCTACTACTGCCAACAGCACAACGAGAACCCCCTGACCTTCGGCGGC 121   G  T  K  V  E  I  K  G  G  G  S  G  G  G  G  Q  V  Q  L  V
361   GGAACCAAGGTCGAGATCAAGGGAGGAGGCTCCGGAGGAGGAGGCCAAGTGCAGCTGGTC
                            Linker                    VH
141   Q  S  G  A  E  V  K  K  P  G  A  T  V  K  I  S  C  R  V  S
421   CAATCCGGCGCCGAAGTGAAAAAGCCCGGCGCCACCGTGAAGATCAGCTGCAAGGTGTCC 161   G  F  N  I  K  D  T  Y  I  H  W  V  Q  Q  A  P  G  K  G  L
481   GGCTTCAACATCAAGGACACCTATATCCACTGGGTCCAGCAAGCCCCCGGAAAAGGCCTG 181   E  W  M  G  R  I  D  P  A  N  D  N  T  L  Y  A  S  K  F  Q
541   GAGTGGATGGGACGGATTGACCCCGCCAACGACAACACACTCTATGCCTCCAAGTTCCAG 201   G  R  V  T  I  T  A  D  T  S  T  D  T  A  Y  M  E  L  S  S
601   GGCAGGGTGACAATCACCGCCGACACCAGCACCGACACAGCTTATATGGAGCTGTCCTCC 221   L  R  S  E  D  T  A  V  Y  Y  C  A  R  G  Y  G  Y  Y  V  F
661   CTCCGGTCCGAGGATACCGCCGTCTACTACTGCGCCAGGGGCTACGGCTACTACGTGTTT 241   D  H  W  G  Q  G  T  L  V  T  V  S  S  G  C        SEQ ID NO: 14
721   GACCACTGGGGCCAGGGCACCCTGGTGACAGTGTCCAGCGGAGGCTGC    SEQ ID NO: 10
                                                  CYS
```

<u>aagctt</u> SEQ ID NO: 74

*HinDIII*

FIGURE 11 tctagagccgccacc SEQ ID NO:75

XbaI Kozak

```
    1   M   E   T   D   T   L   L   L   W   V   L   L   L   W   V   P   G   S   T   G
    1   ATGGAGACCGACACCCTGCTGCTCTGGGTCCTCCTGCTGTGGGTGCCTGGCAGCACAGGA
        Signal Peptide
   21   Q   V   Q   L   V   Q   S   G   A   E   V   K   K   P   G   A   T   V   K   I
   61   CAGGTGCAACTGGTGCAGAGCGGCGCCGAGGTCAAGAAACCTGGCGCCACCGTGAAGATC
        VH
   41   S   C   K   V   S   G   F   N   I   K   D   T   Y   I   H   W   V   Q   Q   A
  121   AGCTGCAAGGTGTCCGGCTTCAACATCAAGGACACCTACATCCACTGGGTCCAACAAGCC 61   P   G   K   G   L   E   W   M   G   R   I   D   P   A   N   D   N   T   L   Y
  181   CCCGGAAAGGGCCTGGAATGGATGGGCCGGATTGACCCCGCCAACGACAACACCCTCTAT 81   A   S   K   F   Q   G   R   V   T   I   T   A   D   T   S   T   D   T   A   Y
  241   GCCAGCAAGTTCCAGGGCAGGGTCACCATCACCGCCGACACCAGCACCGACACCGCCTAC 101   M   E   L   S   S   L   R   S   E   D   T   A   V   Y   Y   C   A   R   G   Y
  301   ATGGAGCTGAGCAGCCTGCGGAGCGAAGACACCGCCGTGTACTACTGCGCCAGGGGCTAC 121   G   Y   Y   V   F   D   H   W   G   Q   G   T   L   V   T   V   S   S   G   G
  361   GGCTACTACGTCTTCGACCATTGGGGACAGGGCACCCTCGTGACAGTGTCCAGCGGAGGA
                                                                          Linker
  141   G   S   G   G   G   D   I   Q   M   T   Q   S   P   S   S   L   S   A   S
  421   GGATCCGGCGGAGGAGGAGATATCCAGATGACCCAGAGCCCTTCCAGCCTGTCCGCTTCC
                                   VL
  161   V   G   D   R   V   T   I   T   C   K   T   S   R   S   I   S   Q   Y   L   A
  481   GTGGGAGATCGGGTGACCATCACATGCAGGACCTCCAGGTCCATCTCCCAGTACCTGGCC 181   W   Y   Q   Q   K   P   G   K   V   P   K   L   L   I   Y   S   G   S   T   L
  541   TGGTACCAACAGAAGCCCGGCAAGGTGCCCAAGCTGCTGATCTACAGCGGCAGCACACTG 201   Q   S   G   V   P   S   R   F   S   G   S   G   S   G   T   D   F   T   L   T
  601   CAATCCGGCGTCCCTTCCCGGTTTTCCGGATCCGGATCCGGCACCGACTTCACCCTGACC 221   I   S   S   L   Q   P   E   D   V   A   T   Y   Y   C   Q   Q   R   N   E   N
  661   ATCAGCTCCCTGCAACCCGAGGACGTGGCCACCTACTACTGTCAGCAGCACAACGAGAAC 241   P   L   T   F   G   G   G   T   K   V   E   I   K   G   G   C              SEQ ID NO: 15
  721   CCCCTCACCTTTGCGGCGGAACCAAGGTCGAGATCAAGGGCGGCTGC              SEQ ID NO: 11
                                                          CYS
``` aagctt SEQ ID NO:76

HinDIII

FIG. 12A  Cys-diabodies

Leader sequence:
```
atggaaacgacacccctgctgctgtgggtgctgctgctctgggtcccaggctccaccggt  SEQ ID NO: 25
 M   E   T   D   T   L   L   L   W   V   L   L   L   W   V   P   G   S   T   G    SEQ ID NO: 26
```

Five aa linker:
```
agtggtggaggaggc  SEQ ID NO: 27
 S   G   G   G   G    SEQ ID NO: 28
```

Eight aa linker:
```
ggcggaggagtggcggaggcggc       SEQ ID NO: 29
 G   G   G   S   G   G   G   G    SEQ ID NO: 30
```

Cysteine tail:
```
ggcggctgc  SEQ ID NO: 31
 G   G   C    SEQ ID NO: 32
```

FIG. 12B  Minibodies

Leader sequence:
```
atggaaacgacacccctgctgctgtgggtgctgctgctctgggtcccaggctccaccggt  SEQ ID NO: 33
 M   E   T   D   T   L   L   L   W   V   L   L   L   W   V   P   G   S   T   G    SEQ ID NO: 34
```

Eighteen aa linker:
```
ggctccacatccggcggaggctctggcggtggatctggcggaggcggctcatcc  SEQ ID NO: 35
 G   S   T   S   G   G   G   S   G   G   G   S   G   G   G   G   S   S    SEQ ID NO: 36
```

IgG1 hinge/linker-CH3 domain:
```
gagcctaagtcctgcgacaagacccacacctgtcccccttgcggcggaggaagcagcgga
 E   P   K   S   C   D   K   T   H   T   C   P   P   C   G   G   G   S   S   G
ggcggatccggtggccagcctcgggagcctcaggtgtacaccctgcctccctcccggac
 G   G   S   G   G   Q   P   R   E   P   Q   V   Y   T   L   P   P   S   R   D
gagctgaccaagaaccaggtgtccctgacctgtctggtcaagggcttctaccctccgat
 E   L   T   K   N   Q   V   S   L   T   C   L   V   K   G   F   Y   P   S   D
atcgccgtggagtgggagtccaacggccagcctgagaacaactacaagaccacccctcct
 I   A   V   E   W   E   S   N   G   Q   P   E   N   N   Y   K   T   T   P   P
gtgctggactccgacggctccttcttcctgtactccaagctcacagtggataagtccgg
 V   L   D   S   D   G   S   F   F   L   Y   S   K   L   T   V   D   K   S   R
tggcagcagggcaacgtgttctcctgctccgtgatgcacgaggccctgcacaaccactat
 W   Q   Q   G   N   V   F   S   C   S   V   M   H   E   A   L   H   N   H   Y
acccagaagtccctgtccctgtctcctggcaag    SEQ ID NO: 37
 T   Q   K   S   L   S   L   S   P   G   K     SEQ ID NO: 38
```

FIG. 12B Continued
Hinge regions:

Amino acid sequences of IgG hinge regions and variants.

|  | Upper | Middle | Lower/extension |
|---|---|---|---|
| IgG1 (SEQ ID NO: 53) | EPKSCDKTHT | CPPCP | APELLGGP |
| IgG1v1 (SEQ ID NO: 54) | EPKSCDKTHT | CPPCP | GGGSSGGSG |
| IgG2.NH (SEQ ID NO: 55) | ERK | CCVECPPCP | APPVA-GP |
| IgG3 (SEQ ID NO: 56) | ELKTPLGDTTHT | CPRCP(EPKSCDTPPPCPRCP)x3 | APELLGGP |
| IgG3v1 (SEQ ID NO: 57) | ELKTPLGDTTHT | CPPCP | APELLGGP |
| IgG3v2 (SEQ ID NO: 58) | EPKSCDTPPP | CPRCP | APELLGGP |
| IgG4 (SEQ ID NO: 59) | ESKYGPP | CPSCP | APEFLGGP |
| IgG4v1 (SEQ ID NO: 60) | ESKYGPP | CPPCP | APEFLGGP |
| IgG2.BH (SEQ ID NO: 79) | EPK | CCVECPPCP | GGGSSGGSG |

CH3 Domains:

Alignment of the hIgG2 CH3 vs hIgG1 CH3 (Amino Acid Sequences):

hIgG2 CH3    GQPREPQVYTLPPSREEMTKNQVSLTCLVKGFYPSDIAVEWESNGQPENNYKTTPPMLDS hIgG1 CH3    GQPREPQVYTLPPSRDELTKNQVSLTCLVKGFYPSDIAVEWESNGQPENNYKTTPPVLDS

************ ;:******************************* :* hIgG2 CH3    DGSFFLYSKLTVDKSRWQQGNVFSCSVMHEALHNHYTQKSLSLSPGK  (SEQ ID NO: 80)

hIgG1 CH3    DGSFFLYSKLTVDKSRWQQGNVFSCSVMHEALHNHYTQKSLSLSPGK- (SEQ ID NO: 81)

Murine VL gatgtccagataaaccagtctccatcttttcttgctgcgtctcctggagaaaccattact
 D   V   Q   I   N   Q   S   P   S   F   L   A   A   S   P   G   E   T   I   T ataaattgc aggacaagtaggagtattagtcaatatttagcc tggtatcaagagaaacct
 I   N   C   R   T   S   R   S   I   S   Q   Y   L   A   W   Y   Q   E   K   P gggaaaactaataagcttcttatctac tctggatccactctgcaatct ggaattccatca
 G   K   T   N   K   L   L   I   Y   S   G   S   T   L   Q   S   G   I   P   S aggttcagtggcagtggatctggtacagatttcactctcaccatcagtggcctggagcct
 R   F   S   G   S   G   S   G   T   D   F   T   L   T   I   S   G   L   E   P gaagattttgcaatgtattactgt caacagcataatgaaaacccgctcacg ttcggtgct
 E   D   F   A   M   Y   Y   C   Q   Q   H   N   E   N   P   L   T   F   G   A gggaccaagctggagctgaag   SEQ ID NO: 39
 G   T   K   L   E   L   K   SEQ ID NO: 40

FIG. 12D huVL gacgtccagataaaccagtctccatcctccctgtctgcatctgtaggagacagagtcacc
 D   V   Q   I   T   Q   S   P   S   S   L   S   A   S   V   G   D   R   V   T atcacttgc aggacaagtaggagtattagtcaatatttagcc tggtatcagcagaaacca
 I   T   C   R   T   S   R   S   I   S   Q   Y   L   A   W   Y   Q   Q   K   P gggaaagttcctaagctcctgatctat tctggatccactctgcaatct ggagtcccatct
 G   K   V   P   K   L   L   I   Y   S   G   S   T   L   Q   S   G   V   P   S cggttcagtggcagtggatctgggacagatttcactctcaccatcagcagcctgcagcct
 R   F   S   G   S   G   S   G   T   D   F   T   L   T   I   S   S   L   Q   P gaagatgttgcaacttattactgt caacagcataatgaaaacccgctcacg ttcggcgga
 E   D   V   A   T   Y   Y   C   Q   Q   H   N   E   N   P   L   T   F   G   G gggaccaaggtggagatcaaa   SEQ ID NO: 41
 G   T   K   V   E   I   K   SEQ ID NO: 42

FIG. 12E

Murine VH gaggtccagctgcagcagtctggggcagagcttgtgaagccaggggcctcagtcaagttg
E V Q L Q Q S G A E L V K P G A S V K L tcctgcacagcttct ggcttcaacattaaagac acctatatacacttcgtgaggcagagg
S C T A S G F N I K D T Y I H F V R Q R cctgaacaggcctggagtggattgga aggattgatcctgcgaatgataatact ttatat
P E Q G L E W I G R I D P A N D N T L Y gcctcaaagttccagggcaaggccactataacagcagacacatcatccaacacagcctac
A S K F Q G K A T I T A D T S S N T A Y atgcacctctgcagcctgacatctggggacactgccgtctattactgtggtaga ggttat
M H L C S L T S G D T A V Y Y C G R G Y ggttactacgtatttgaccac tggggccaaggcaccactctcacagtctcctca SEQ ID NO: 43
G Y Y V F D H W G Q G T T L T V S S    SEQ ID NO: 44

FIG. 12F
huVH version a  (From VH version 1)

gaagtgcagctggtggaaagcggcggcggcctggtgcagccggcggcagcctgcgcctg
E V Q L V E S G G G L V Q P G G S L R L
agctgcgcggcgagc ggctttaacattaaagat acctatattcattttgtgcgccaggcg
S C A A S G F N I K D T Y I H F V R Q A
ccgggcaaaggcctggaatggattggc cgcattgatccggcgaacgataacacc ctgtat
P G K G L E W I G R I D P A N D N T L Y
gcgagcaaatttcagggcaaagcgaccattagcgcggataccagcaaaaacaccgcgtat
A S K F Q G K A T I S A D T S K N T A Y
ctgcagatgaacagcctgcgcgcgggagataccgcggtgtattattgcggccgc ggctat
L Q M N S L R A G D T A V Y Y C G R G Y
ggctattatgtgtttgatcat tggggccagggcaccctggtgaccgtgagcagc SEQ ID NO: 45
G Y Y V F D H W G Q G T L V T V S S    SEQ ID NO: 46

FIG. 12G huVH version b (From VH version 1)

```
gaagtgcagctggtggaaagcggcggcggcctggtgcagccggcggcagcctgcgcctg
 E  V  Q  L  V  E  S  G  G  G  L  V  Q  P  G  G  S  L  R  L
agctgcgcggcgagc ggctttaacattaaagat acctatattcattttgtgcgccaggcg
 S  C  A  A  S   G  F  N  I  K  D   T  Y  I  H  F  V  R  Q  A
ccgggcaaaggcctggaatggattggc cgcattgatccggcgaacgataacacc ctgtat
 P  G  K  G  L  E  W  I  G   R  I  D  P  A  N  D  N  T   L  Y
gcgagcaaattccagggcaaagcgaccattagcgcggataccagcaaaaacaccgcgtat
 A  S  K  F  Q  G  K  A  T  I  S  A  D  T  S  K  N  T  A  Y
ctgcagatgaacagcctgcgcgcggaagataccgcggtgtattattgcggcgc ggctat
 L  Q  M  R  S  L  R  A  E  D  T  A  V  Y  Y  C  G  R   G  Y
ggctattatgtgtttgatcat tggggccagggcaccctggtgaccgtgagcagc  SEQ ID NO: 47
 G  Y  Y  V  F  D  H   W  G  Q  G  T  L  V  T  V  S  S   SEQ ID NO: 48
```

FIG. 12H huVH version c (From VH version 2)

```
caggtgcagctggtgcagagcggcgcgggagtgaaaaaaccggggcgcgaccgtgaaaatt
 Q  V  Q  L  V  Q  S  G  A  E  V  K  K  P  G  A  T  V  K  I
agctgcaaagtgagc ggctttaacattaaagat acctatattcattttgtgcagcaggcg
 S  C  K  V  S   G  F  N  I  K  D   T  Y  I  H  F  V  Q  Q  A
ccgggcaaaggcctggaatggattggc cgcattgatccggcgaacgataacacc ctgtat
 P  G  K  G  L  E  W  I  G   R  I  D  P  A  N  D  N  T   L  Y
gcgagcaaattccagggcaaagcgaccattaccgcggataccagcaccgatacc gcgtat
 A  S  K  F  Q  G  K  A  T  I  T  A  D  T  S  T  D  T  A  Y
atggaactgagcagcctgcgcagcggagataccgcggtgtattattgcggcgc ggctat
 M  E  L  S  S  L  R  S  G  D  T  A  V  Y  Y  C  G  R   G  Y
ggctattatgtgtttgatcat tggggccagggcaccctggtgaccgtgagcagc  SEQ ID NO: 49
 G  Y  Y  V  F  D  H   W  G  Q  G  T  L  V  T  V  S  S   SEQ ID NO: 50
```

FIG. 12I huVH version d (From VH version 2)

```
caggtgcagctggtgcagagcggcgcgggagtgaaaaaaccggggcgcgaccgtgaaaatt
 Q  V  Q  L  V  Q  S  G  A  E  V  K  K  P  G  A  T  V  K  I
agctgcaaagtgagc ggctttaacattaaagat acctatattcattttgtgcagcaggcg
 S  C  K  V  S   G  F  N  I  K  D   T  Y  I  H  F  V  Q  Q  A
ccgggcaaaggcctggaatggattggc cgcattgatccggcgaacgataacacc ctgtat
 P  G  K  G  L  E  W  I  G   R  I  D  P  A  N  D  N  T   L  Y
gcgagcaaattccagggcaaagcgaccattaccgcggataccagcaccgatacc gcgtat
 A  S  K  F  Q  G  K  A  T  I  T  A  D  T  S  T  D  T  A  Y
atggaactgagcagcctgcgcagcgaagataccgcggtgtattattgcggcgc ggctat
 M  E  L  S  S  L  R  S  E  D  T  A  V  Y  Y  C  G  R   G  Y
ggctattatgtgtttgatcat tggggccagggcaccctggtgaccgtgagcagc  SEQ ID NO: 51
 G  Y  Y  V  F  D  H   W  G  Q  G  T  L  V  T  V  S      SEQ ID NO: 52
```

Chimeric IAb_Mb1_CD8

Chimeric IAb_Mb2_CD8

Humanized IAb_Mb1_CD8

Humanized IAb_Mb2_CD8

- 1:81 dilution — 1
- 1:27 dilution — 2
- 1:9 dilution — 3
- 1:3 dilution — 4
- Neat — 5
- Unstained cells — 6

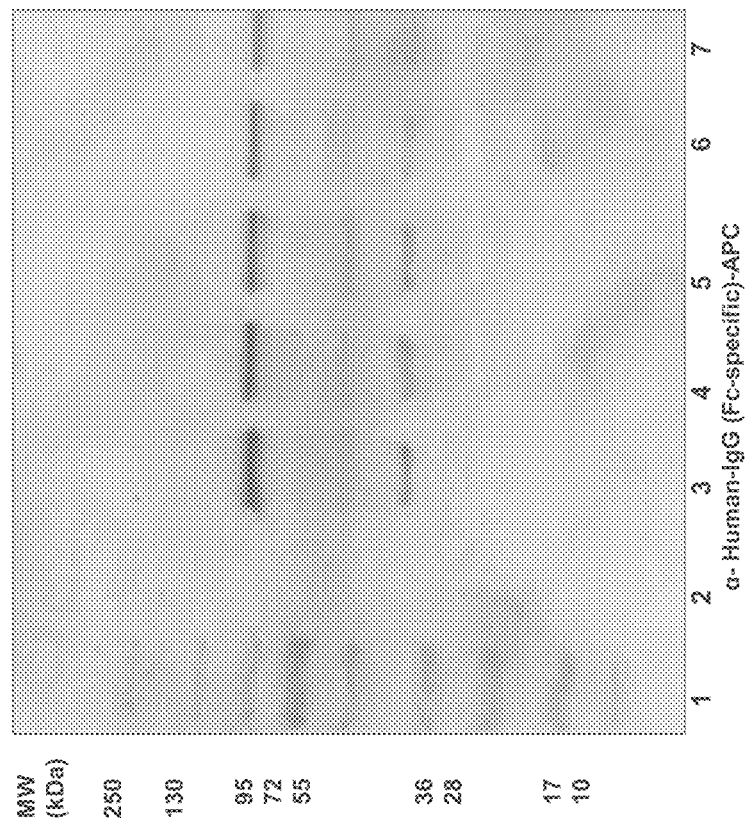

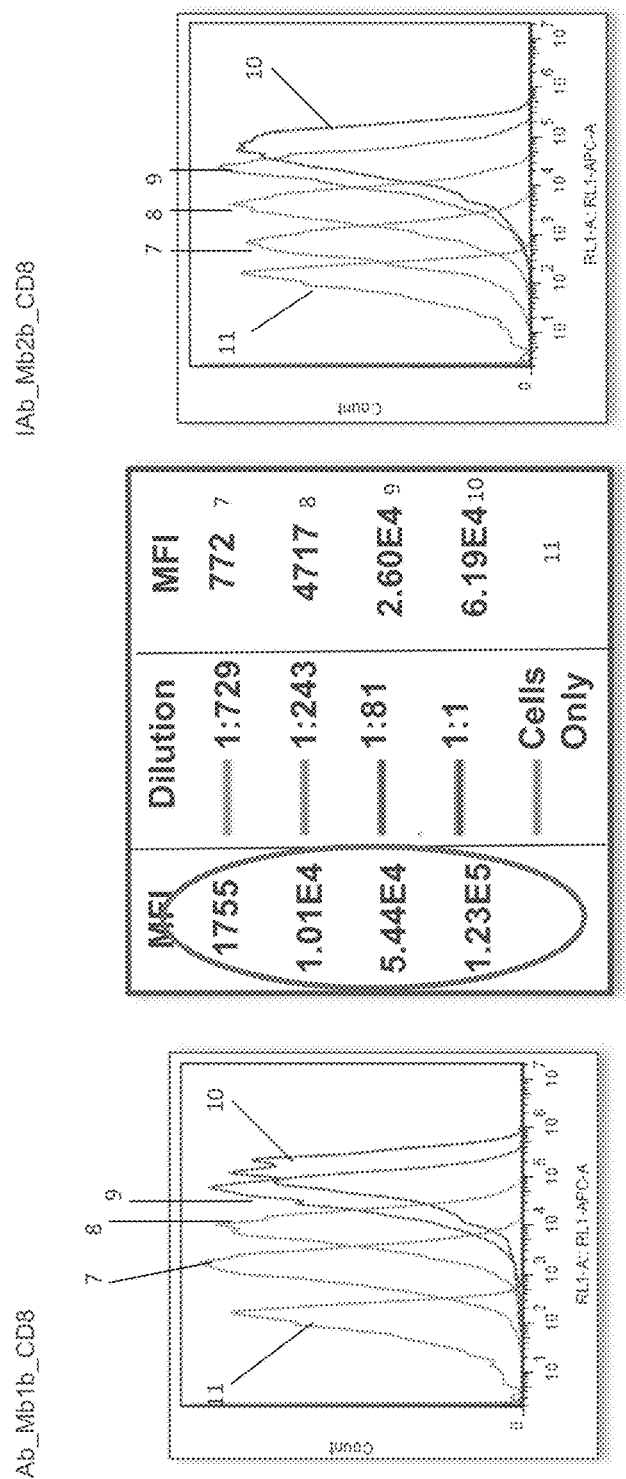

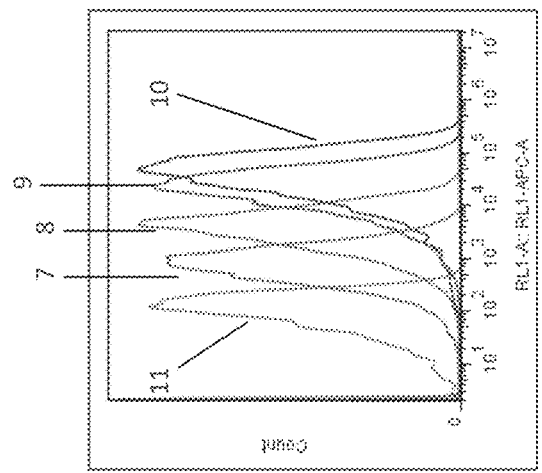
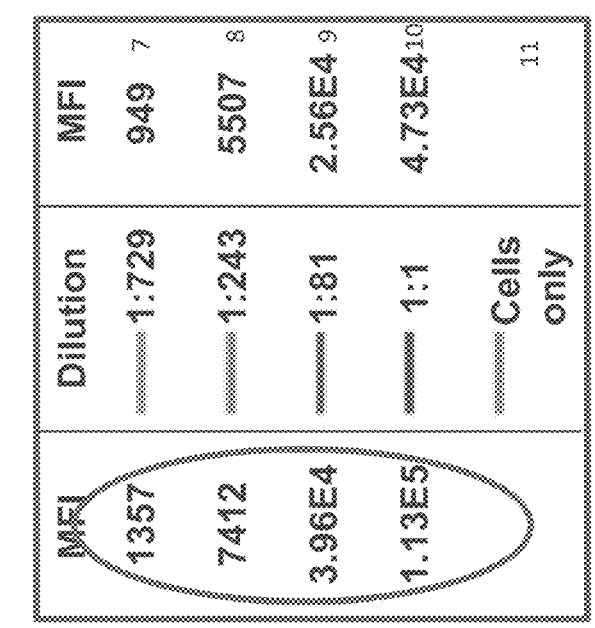
FIG. 22B
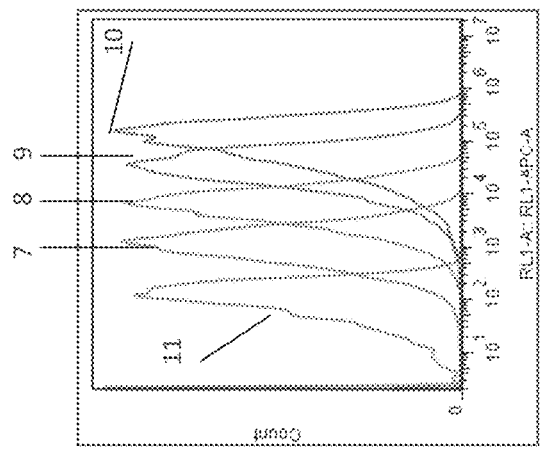

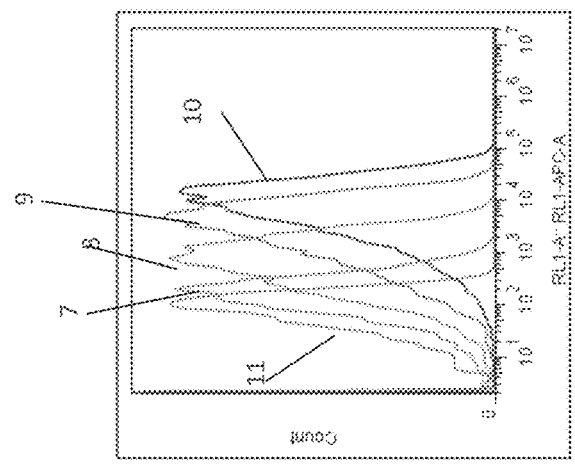
FIG. 23A
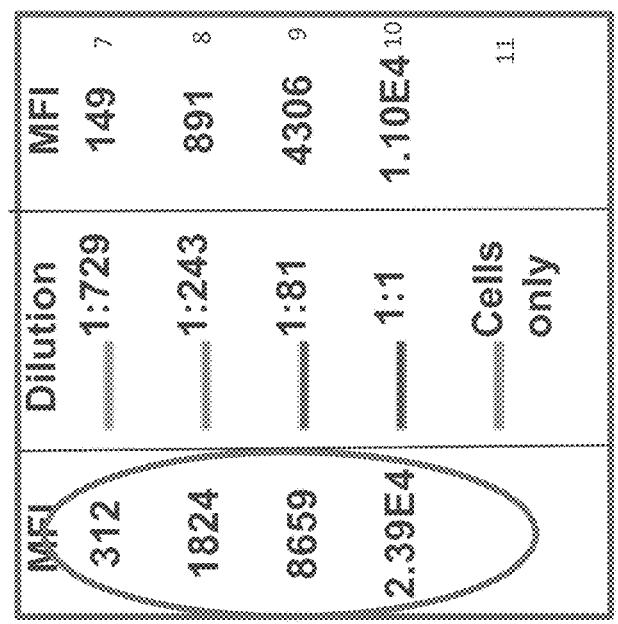
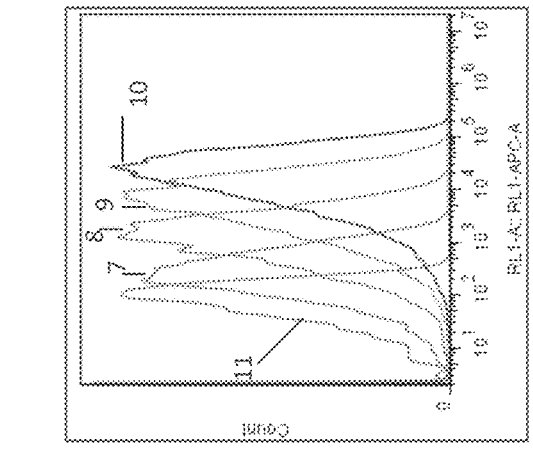

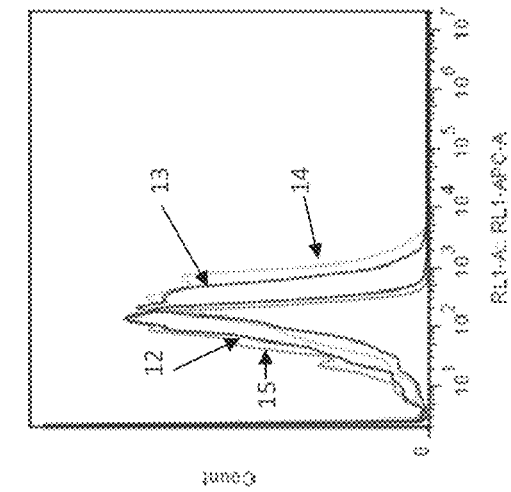
FIG. 26A
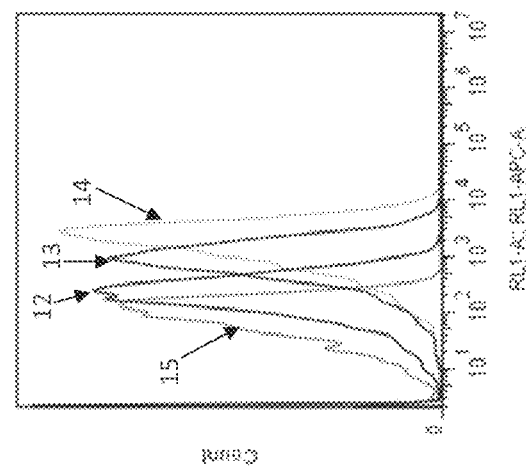

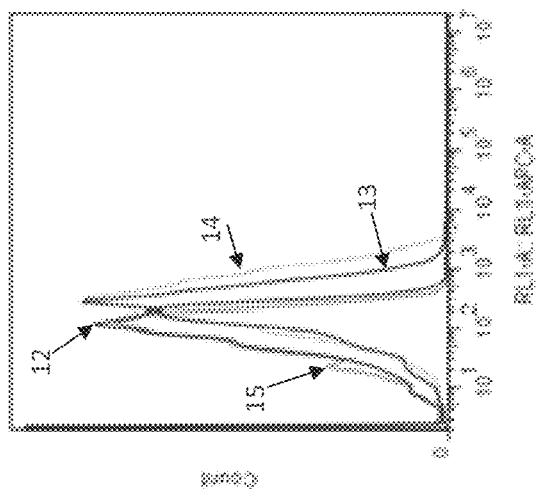
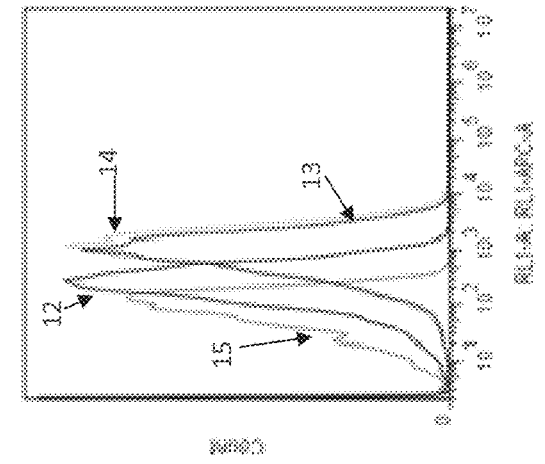
FIG. 26B

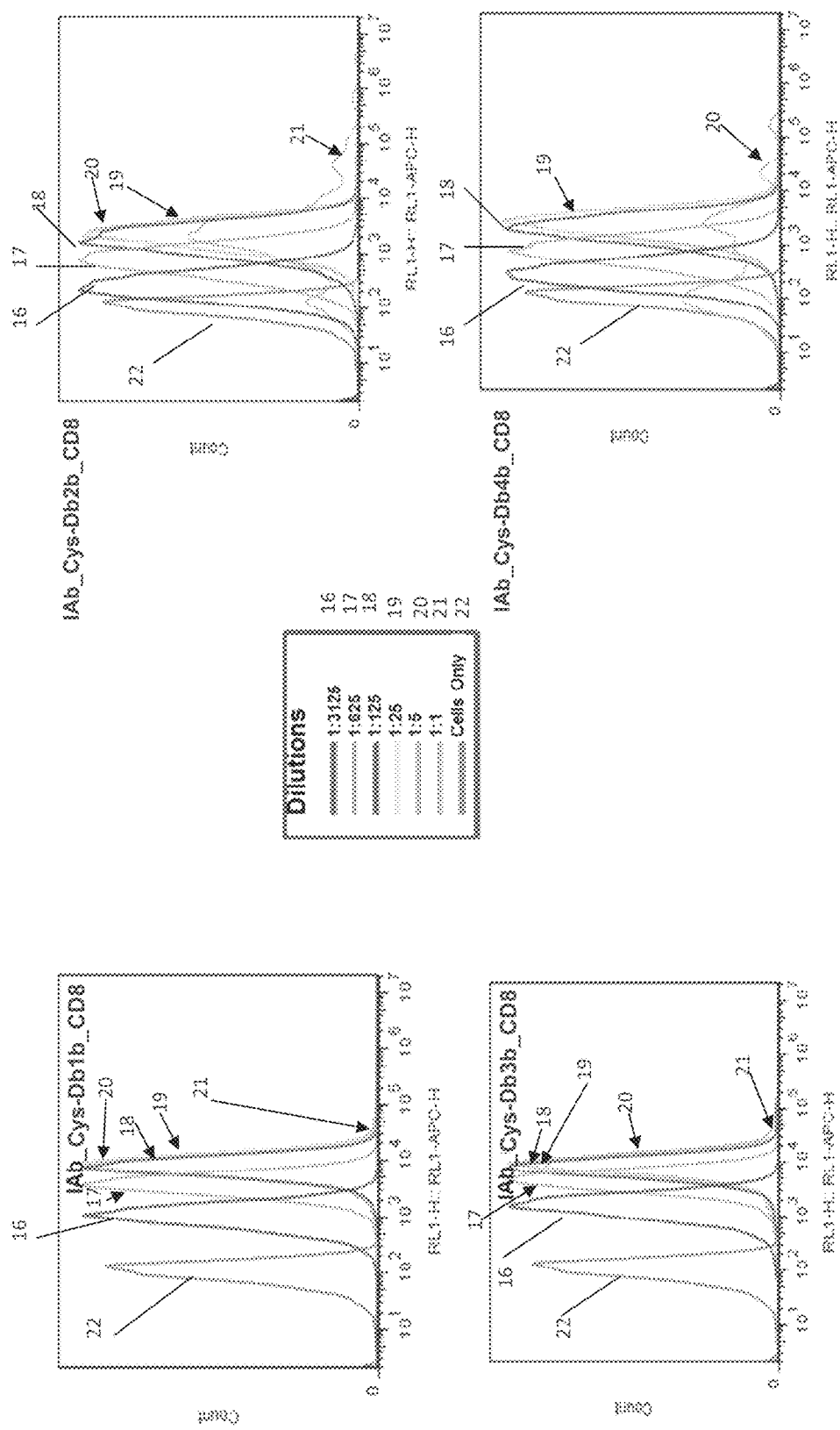

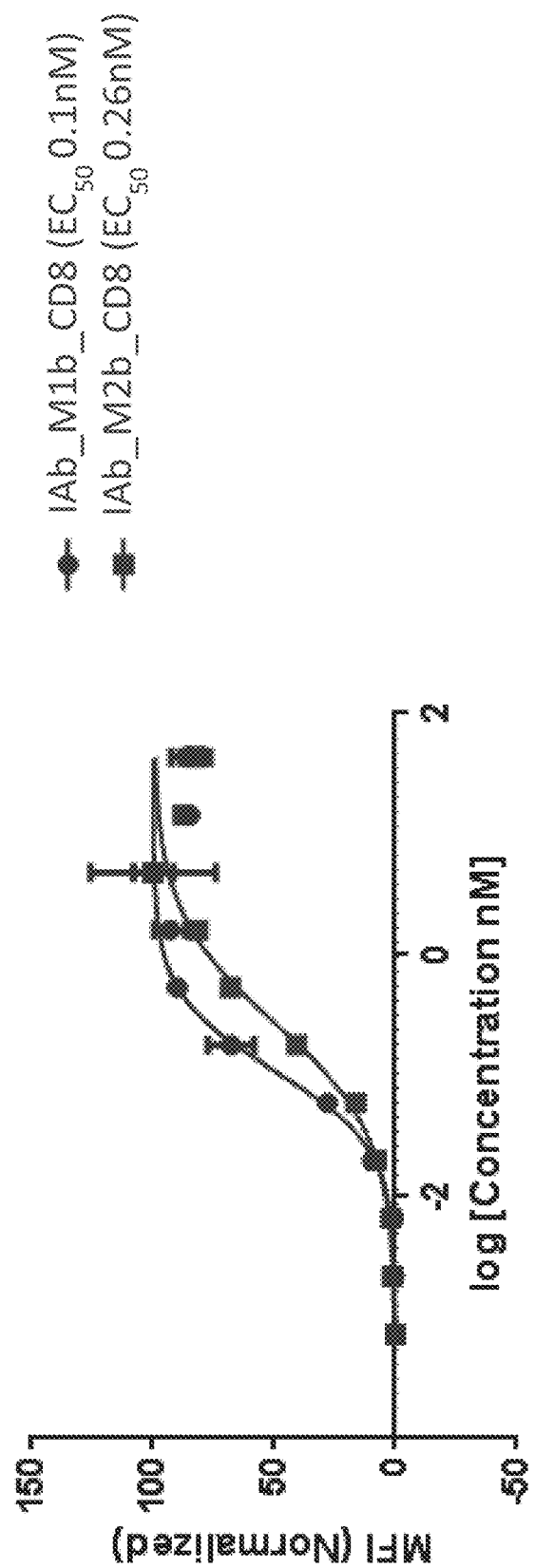

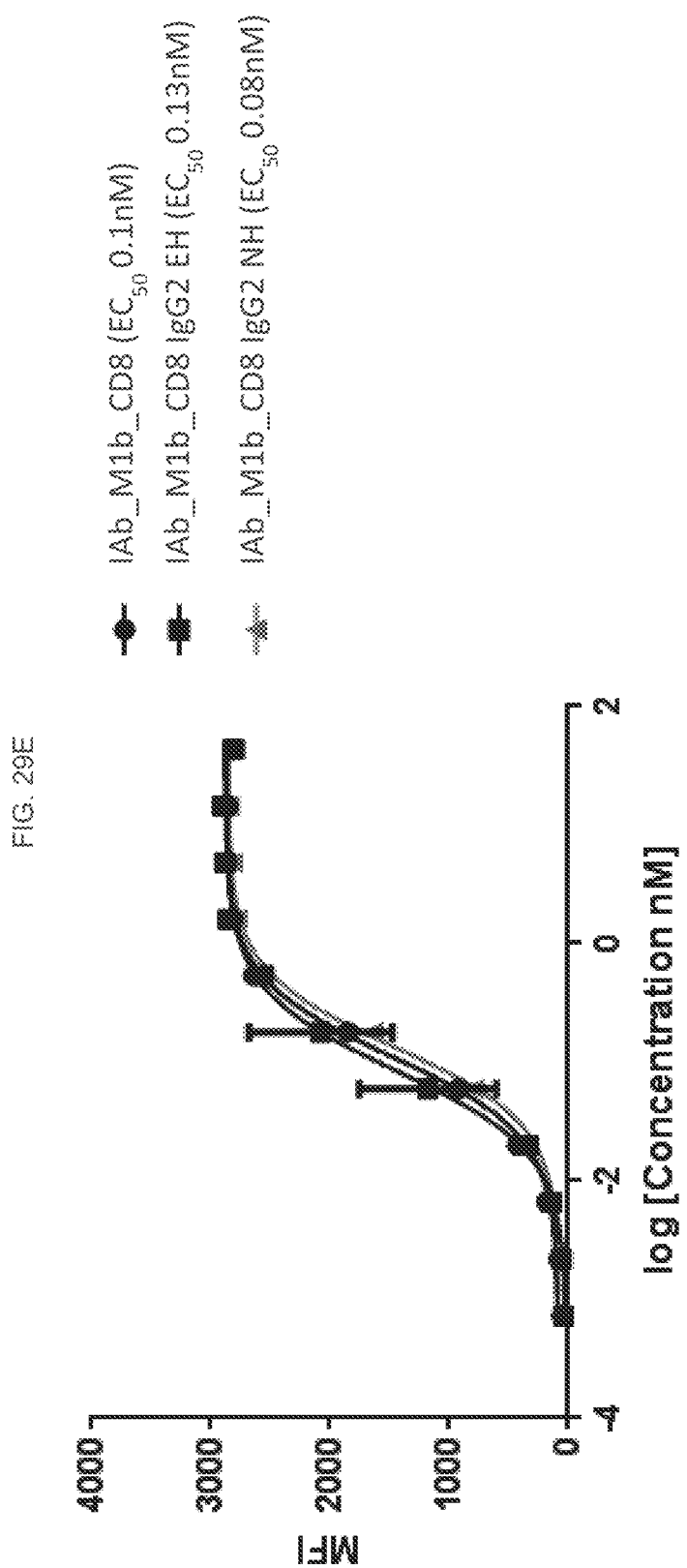

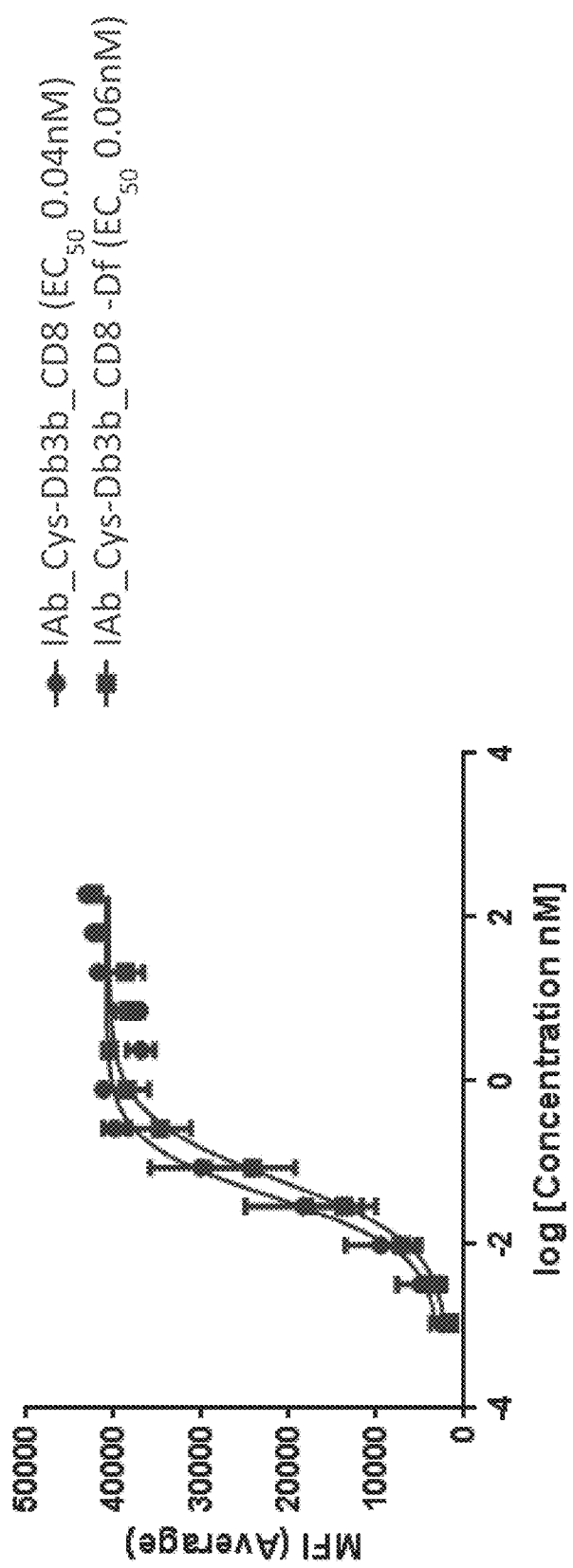

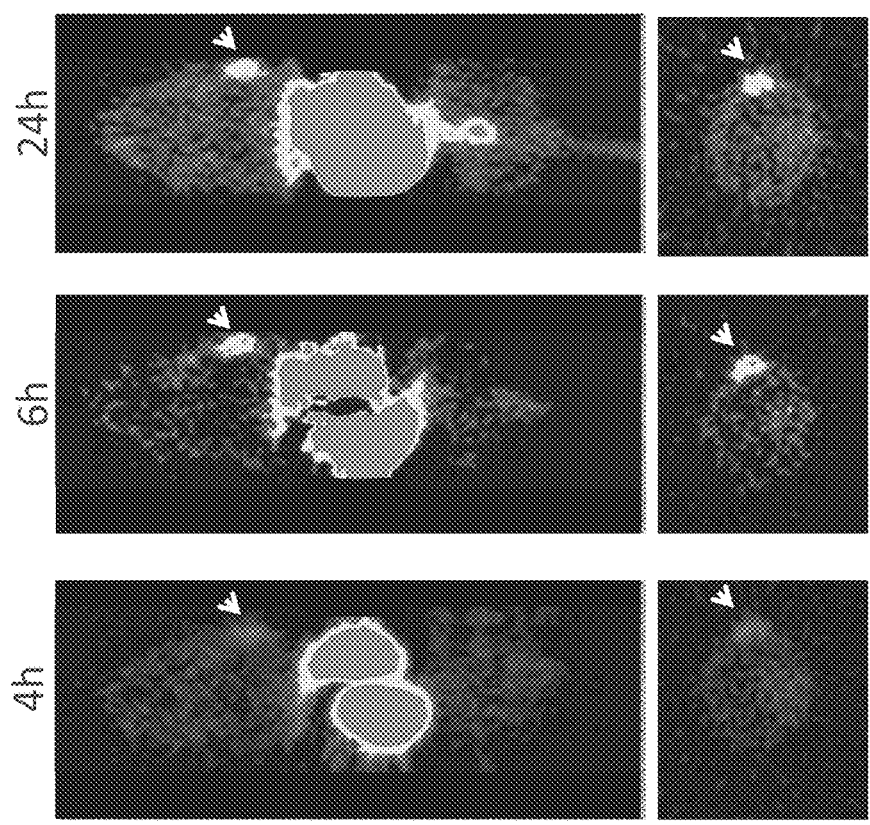

SEQUENCE LISTING

```
<160> NUMBER OF SEQ ID NOS: 81

<210> SEQ ID NO 1
<211> LENGTH: 118
<212> TYPE: PRT
<213> ORGANISM: Murine

<400> SEQUENCE: 1

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Phe Val Arg Gln Arg Pro Glu Gln Gly Leu Glu Trp Ile
        35                  40                  45

Gly Arg Ile Asp Pro Ala Asn Asp Asn Thr Leu Tyr Ala Ser Lys Phe
    50                  55                  60
```

```
Gln Gly Lys Ala Thr Ile Thr Ala Asp Thr Ser Ser Asn Thr Ala Tyr
 65                  70                  75                  80

Met His Leu Cys Ser Leu Thr Ser Gly Asp Thr Ala Val Tyr Tyr Cys
                 85                  90                  95

Gly Arg Gly Tyr Gly Tyr Tyr Val Phe Asp His Trp Gly Gln Gly Thr
            100                 105                 110

Thr Leu Thr Val Ser Ser
        115

<210> SEQ ID NO 2
<211> LENGTH: 120
<212> TYPE: PRT
<213> ORGANISM: Homo sapiens

<400> SEQUENCE: 2

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 3
<211> LENGTH: 118
<212> TYPE: PRT
<213> ORGANISM: Artificial Sequence
<220> FEATURE:
<223> OTHER INFORMATION: Antigen binding construct or fragment thereof

<400> SEQUENCE: 3

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Asp Pro Ala Asn Asp Asn Thr Leu Tyr Ala Ser Lys Phe
 50                  55                  60

Gln Gly Arg Ala Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Gly Arg Gly Tyr Gly Tyr Tyr Val Phe Asp His Trp Gly Gln Gly Thr
            100                 105                 110

Leu Val Thr Val Ser Ser
        115
```

<210> SEQ ID NO 4
<211> LENGTH: 118
<212> TYPE: PRT
<213> ORGANISM: Murine

<400> SEQUENCE: 4

Gln Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Phe Val Arg Gln Arg Pro Glu Gln Gly Leu Glu Trp Ile
        35                  40                  45

Gly Arg Ile Asp Pro Ala Asn Asp Asn Thr Leu Tyr Ala Ser Lys Phe
    50                  55                  60

Gln Gly Lys Ala Thr Ile Thr Ala Asp Thr Ser Ser Asn Thr Ala Tyr
65                  70                  75                  80

Met His Leu Cys Ser Leu Thr Ser Gly Asp Thr Ala Val Tyr Tyr Cys
                85                  90                  95

Gly Arg Gly Tyr Gly Tyr Tyr Val Phe Asp His Trp Gly Gln Gly Thr
            100                 105                 110

Thr Leu Thr Val Ser Ser
        115

<210> SEQ ID NO 5
<211> LENGTH: 115
<212> TYPE: PRT
<213> ORGANISM: Homo sapiens

<400> SEQUENCE: 5

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ala Glu Tyr Phe Gln His Trp Gly Gln Gly Thr Leu Val Thr
            100                 105                 110

Val Ser Ser
        115

<210> SEQ ID NO 6
<211> LENGTH: 118
<212> TYPE: PRT
<213> ORGANISM: Artificial Sequence
<220> FEATURE:
<223> OTHER INFORMATION: Antigen binding construct or fragment thereof

<400> SEQUENCE: 6

Gln Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Thr
            20                  25                  30

Tyr Ile His Trp Val Gln Gln Ala Pro Gly Lys Gly Leu Glu Trp Met
            35                  40                  45

Gly Arg Ile Asp Pro Ala Asn Asp Asn Thr Leu Tyr Ala Ser Lys Phe
        50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Gly Tyr Tyr Val Phe Asp His Trp Gly Gln Gly Thr
            100                 105                 110

Leu Val Thr Val Ser Ser
        115

<210> SEQ ID NO 7
<211> LENGTH: 107
<212> TYPE: PRT
<213> ORGANISM: Murine

<400> SEQUENCE: 7

Asp Val Gln Ile Asn Gln Ser Pro Ser Phe Leu Ala Ala Ser Pro Gly
1               5                   10                  15

Glu Thr Ile Thr Ile Asn Cys Arg Thr Ser Arg Ser Ile Ser Gln Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Gly Leu Glu Pro
65                  70                  75                  80

Glu Asp Phe Ala Met Tyr Tyr Cys Gln Gln His Asn Glu Asn Pro Leu
                85                  90                  95

Thr Phe Gly Ala Gly Thr Lys Leu Glu Leu Lys
            100                 105

<210> SEQ ID NO 8
<211> LENGTH: 107
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Leu
                85                  90                  95

Thr Phe Gly Gly Gly Thr Lys Val Glu Ile Lys
            100                 105

<210> SEQ ID NO 9

<211> LENGTH: 107
<212> TYPE: PRT
<213> ORGANISM: Artificial Sequence
<220> FEATURE:
<223> OTHER INFORMATION: Antigen binding construct or fragment thereof

<400> SEQUENCE: 9

Asp Val Gln Ile Thr Gln Ser Pro Ser Ser Leu Ser Ala Ser Val Gly
1               5                   10                  15

Asp Arg Val Thr Ile Thr Cys Arg Thr Ser Arg Ser Ile Ser Gln Tyr
            20                  25                  30

Leu Ala Trp Tyr Gln Gln Lys Pro Gly Lys Val Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln His Asn Glu Asn Pro Leu
                85                  90                  95

Thr Phe Gly Gly Gly Thr Lys Val Glu Ile Lys
            100                 105

<210> SEQ ID NO 10
<211> LENGTH: 768
<212> TYPE: DNA
<213> ORGANISM: Artificial Sequence
<220> FEATURE:
<223> OTHER INFORMATION: Antigen binding construct or fragment thereof

<400> SEQUENCE: 10
atggagaccg atacactgct gctgtgggtg ctgctgctct gggtccctgg cagcacagga      60
gacatccaga tgacacagag ccctagctcc ctgagcgctt ccgtgggaga tagggtgacc     120
atcacatgcc ggacctccag gtccatctcc cagtacctgg cctggtacca gcagaagccc     180
ggcaaggtgc ccaagctgct catctatagc ggcagcaccc tgcagagcgg agtgccttcc     240
cggttttccg gatccggctc cggcacagac tttacccctga ccatctccag cctgcagcct     300
gaggatgtcg ccacctacta ctgccaacag cacaacgaga ccccctgac cttcggcggc     360
ggaaccaagg tcgagatcaa gggaggaggc tccggaggag aggccaagt gcagctggtc     420
caatccggcg ccgaagtgaa aaagcccggc gccaccgtga gatcagctg caaggtgtcc     480
ggcttcaaca tcaaggacac ctatatccac tgggtccagc aagcccccgg aaaaggcctg     540
gagtggatgg gacggattga ccccgccaac gacaacacac tctatgcctc aagttccag     600
ggcagggtga caatcaccgc cgacaccagc accgacacag cttatatgga gctgtcctcc     660
ctccggtccg aggataccgc cgtctactac tgcgccaggg gctacggcta ctacgtgttt     720
gaccactggg gccagggcac cctggtgaca gtgtccagcg aggctgc                   768

<210> SEQ ID NO 11
<211> LENGTH: 768
<212> TYPE: DNA
<213> ORGANISM: Artificial Sequence
<220> FEATURE:
<223> OTHER INFORMATION: Antigen binding construct or fragment thereof

<400> SEQUENCE: 11
atggagaccg acaccctgct gctctgggtc ctcctgctgt gggtgcctgg cagcacagga      60
caggtgcaac tggtgcagag cggcgccgag gtcaagaaac tggcgccac cgtgaagatc     120

-continued

```
agctgcaagg tgtccggctt caacatcaag gacacctaca tccactgggt ccaacaagcc      180
cccggaaagg gcctggaatg gatgggccgg attgaccccg ccaacgacaa cacccctctat     240 gccagcaagt tccagggcag ggtcaccatc accgccgaca ccagcaccga caccgcctac     300
atggagctga gcagcctgcg gagcgaagac accgccgtgt actactgcgc cagggggctac    360 ggctactacg tcttcgacca ttggggacag ggcaccctcg tgacagtgtc cagcggagga    420
ggatccggcg gaggaggaga tatccagatg acccagagcc cttccagcct gtccgcttcc    480
gtgggagatc gggtgaccat cacatgcagg acctccaggt ccatctccca gtacctggcc    540
tggtaccaac agaagcccgg caaggtgccc aagctgctga tctacagcgg cagcacactg    600
caatccggcg tcccttcccg gttttccgga tccggatccg gcaccgactt cacccctgacc   660 atcagctccc tgcaacccga ggacgtggcc acctactact gtcagcagca caacgagaac    720 ccctcacct ttggcggcgg aaccaaggtc gagatcaagg gcggctgc                 768
```

<210> SEQ ID NO 12
<211> LENGTH: 253
<212> TYPE: PRT
<213> ORGANISM: Artificial Sequence
<220> FEATURE:
<223> OTHER INFORMATION: Antigen binding construct or fragment thereof

<400> SEQUENCE: 12

```
Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Arg Thr Ser Arg Ser
        35                  40                  45

Ile Ser Gln Tyr Leu Ala Trp Tyr Gln Gln Lys Pro Gly Lys Val Pro
    50                  55                  60

Lys Leu Leu Ile Tyr Ser Gly Ser Thr Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Val Ala Thr Tyr Tyr Cys Gln Gln His Asn
            100                 105                 110

Glu Asn Pro Leu Thr Phe Gly Gly Gly Thr Lys Val Glu Ile Lys Ser
        115                 120                 125

Gly Gly Gly Gly Gln Val Gln Leu Val Gln Ser Gly Ala Glu Val Lys
    130                 135                 140

Lys Pro Gly Ala Thr Val Lys Ile Ser Cys Lys Val Ser Gly Phe Asn
145                 150                 155                 160

Ile Lys Asp Thr Tyr Ile His Trp Val Gln Gln Ala Pro Gly Lys Gly
                165                 170                 175

Leu Glu Trp Met Gly Arg Ile Asp Pro Ala Asn Asp Asn Thr Leu Tyr
            180                 185                 190

Ala Ser Lys Phe Gln Gly Arg Val Thr Ile Thr Ala Asp Thr Ser Thr
        195                 200                 205

Asp Thr Ala Tyr Met Glu Leu Ser Ser Leu Arg Ser Glu Asp Thr Ala
    210                 215                 220

Val Tyr Tyr Cys Ala Arg Gly Tyr Gly Tyr Tyr Val Phe Asp His Trp
225                 230                 235                 240

Gly Gln Gly Thr Leu Val Thr Val Ser Ser Gly Gly Cys
                245                 250
```

<210> SEQ ID NO 13
<211> LENGTH: 253
<212> TYPE: PRT
<213> ORGANISM: Artificial Sequence
<220> FEATURE:
<223> OTHER INFORMATION: Antigen binding construct or fragment thereof

<400> SEQUENCE: 13

```
Met Glu Thr Asp Thr Leu Leu Leu Trp Val Leu Leu Leu Trp Val Pro
1               5                   10                  15

Gly Ser Thr Gly Gln Val Gln Leu Val Gln Ser Gly Ala Glu Val Lys
            20                  25                  30

Lys Pro Gly Ala Thr Val Lys Ile Ser Cys Lys Val Ser Gly Phe Asn
        35                  40                  45

Ile Lys Asp Thr Tyr Ile His Trp Val Gln Gln Ala Pro Gly Lys Gly
    50                  55                  60

Leu Glu Trp Met Gly Arg Ile Asp Pro Ala Asn Asp Asn Thr Leu Tyr
65                  70                  75                  80

Ala Ser Lys Phe Gln Gly Arg Val Thr Ile Thr Ala Asp Thr Ser Thr
                85                  90                  95

Asp Thr Ala Tyr Met Glu Leu Ser Ser Leu Arg Ser Glu Asp Thr Ala
            100                 105                 110

Val Tyr Tyr Cys Ala Arg Gly Tyr Gly Tyr Tyr Val Phe Asp His Trp
        115                 120                 125

Gly Gln Gly Thr Leu Val Thr Val Ser Ser Gly Gly Gly Gly Gly Asp
    130                 135                 140

Ile Gln Met Thr Gln Ser Pro Ser Ser Leu Ser Ala Ser Val Gly Asp
145                 150                 155                 160

Arg Val Thr Ile Thr Cys Arg Thr Ser Arg Ser Ile Ser Gln Tyr Leu
                165                 170                 175

Ala Trp Tyr Gln Gln Lys Pro Gly Lys Val Pro Lys Leu Leu Ile Tyr
            180                 185                 190

Ser Gly Ser Thr Leu Gln Ser Gly Val Pro Ser Arg Phe Ser Gly Ser
        195                 200                 205

Gly Ser Gly Thr Asp Phe Thr Leu Thr Ile Ser Ser Leu Gln Pro Glu
    210                 215                 220

Asp Val Ala Thr Tyr Tyr Cys Gln Gln His Asn Glu Asn Pro Leu Thr
225                 230                 235                 240

Phe Gly Gly Gly Thr Lys Val Glu Ile Lys Gly Gly Cys
                245                 250
```

<210> SEQ ID NO 14
<211> LENGTH: 256
<212> TYPE: PRT
<213> ORGANISM: Artificial Sequence
<220> FEATURE:
<223> OTHER INFORMATION: Antigen binding construct or fragment thereof

<400> SEQUENCE: 14

```
Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Arg Thr Ser Arg Ser
        35                  40                  45

Ile Ser Gln Tyr Leu Ala Trp Tyr Gln Gln Lys Pro Gly Lys Val Pro
```

```
             50                  55                  60
Lys Leu Leu Ile Tyr Ser Gly Ser Thr Leu Gln Ser Gly Val Pro Ser
 65                  70                  75                  80

Arg Phe Ser Gly Ser Gly Ser Gly Thr Asp Phe Thr Leu Thr Ile Ser
                     85                  90                  95

Ser Leu Gln Pro Glu Asp Val Ala Thr Tyr Tyr Cys Gln Gln His Asn
                100                 105                 110

Glu Asn Pro Leu Thr Phe Gly Gly Gly Thr Lys Val Glu Ile Lys Gly
            115                 120                 125

Gly Gly Ser Gly Gly Gly Gly Gln Val Gln Leu Val Gln Ser Gly Ala
        130                 135                 140

Glu Val Lys Lys Pro Gly Ala Thr Val Lys Ile Ser Cys Lys Val Ser
145                 150                 155                 160

Gly Phe Asn Ile Lys Asp Thr Tyr Ile His Trp Val Gln Gln Ala Pro
                165                 170                 175

Gly Lys Gly Leu Glu Trp Met Gly Arg Ile Asp Pro Ala Asn Asp Asn
            180                 185                 190

Thr Leu Tyr Ala Ser Lys Phe Gln Gly Arg Val Thr Ile Thr Ala Asp
        195                 200                 205

Thr Ser Thr Asp Thr Ala Tyr Met Glu Leu Ser Ser Leu Arg Ser Glu
210                 215                 220

Asp Thr Ala Val Tyr Tyr Cys Ala Arg Gly Tyr Gly Tyr Tyr Val Phe
225                 230                 235                 240

Asp His Trp Gly Gln Gly Thr Leu Val Thr Val Ser Ser Gly Gly Cys
                245                 250                 255

<210> SEQ ID NO 15
<211> LENGTH: 256
<212> TYPE: PRT
<213> ORGANISM: Artificial Sequence
<220> FEATURE:
<223> OTHER INFORMATION: Antigen binding construct or fragment thereof

<400> SEQUENCE: 15

Met Glu Thr Asp Thr Leu Leu Leu Trp Val Leu Leu Leu Trp Val Pro
  1               5                  10                  15

Gly Ser Thr Gly Gln Val Gln Leu Val Gln Ser Gly Ala Glu Val Lys
                 20                  25                  30

Lys Pro Gly Ala Thr Val Lys Ile Ser Cys Lys Val Ser Gly Phe Asn
             35                  40                  45

Ile Lys Asp Thr Tyr Ile His Trp Val Gln Gln Ala Pro Gly Lys Gly
 50                  55                  60

Leu Glu Trp Met Gly Arg Ile Asp Pro Ala Asn Asp Asn Thr Leu Tyr
 65                  70                  75                  80

Ala Ser Lys Phe Gln Gly Arg Val Thr Ile Thr Ala Asp Thr Ser Thr
                 85                  90                  95

Asp Thr Ala Tyr Met Glu Leu Ser Ser Leu Arg Ser Glu Asp Thr Ala
            100                 105                 110

Val Tyr Tyr Cys Ala Arg Gly Tyr Gly Tyr Tyr Val Phe Asp His Trp
        115                 120                 125

Gly Gln Gly Thr Leu Val Thr Val Ser Ser Gly Gly Ser Gly Gly Gly
    130                 135                 140

Gly Gly Asp Ile Gln Met Thr Gln Ser Pro Ser Ser Leu Ser Ala Ser
145                 150                 155                 160

Val Gly Asp Arg Val Thr Ile Thr Cys Arg Thr Ser Arg Ser Ile Ser
```

```
                    165                 170                 175
Gln Tyr Leu Ala Trp Tyr Gln Gln Lys Pro Gly Lys Val Pro Lys Leu
                180                 185                 190

Leu Ile Tyr Ser Gly Ser Thr Leu Gln Ser Gly Val Pro Ser Arg Phe
            195                 200                 205

Ser Gly Ser Gly Ser Gly Thr Asp Phe Thr Leu Thr Ile Ser Ser Leu
        210                 215                 220

Gln Pro Glu Asp Val Ala Thr Tyr Tyr Cys Gln Gln His Asn Glu Asn
225                 230                 235                 240

Pro Leu Thr Phe Gly Gly Gly Thr Lys Val Glu Ile Lys Gly Gly Cys
                245                 250                 255

<210> SEQ ID NO 16
<211> LENGTH: 394
<212> TYPE: PRT
<213> ORGANISM: Artificial Sequence
<220> FEATURE:
<223> OTHER INFORMATION: Antigen binding construct or fragment thereof

<400> SEQUENCE: 16

Met Glu Thr Asp Thr Leu Leu Leu Trp Val Leu Leu Leu Trp Val Pro
1               5                   10                  15

Gly Ser Thr Gly Asp Val Gln Ile Asn Gln Ser Pro Ser Phe Leu Ala
            20                  25                  30

Ala Ser Pro Gly Glu Thr Ile Thr Ile Asn Cys Arg Thr Ser Arg Ser
        35                  40                  45

Ile Ser Gln Tyr Leu Ala Trp Tyr Gln Glu Lys Pro Gly Lys Thr Asn
    50                  55                  60

Lys Leu Leu Ile Tyr Ser Gly Ser Thr Leu Gln Ser Gly Ile Pro Ser
65                  70                  75                  80

Arg Phe Ser Gly Ser Gly Ser Gly Thr Asp Phe Thr Leu Thr Ile Ser
                85                  90                  95

Gly Leu Glu Pro Glu Asp Phe Ala Met Tyr Tyr Cys Gln Gln His Asn
            100                 105                 110

Glu Asn Pro Leu Thr Phe Gly Ala Gly Thr Lys Leu Glu Leu Lys Gly
        115                 120                 125

Ser Thr Ser Gly Gly Gly Ser Gly Gly Ser Gly Gly Gly Gly Ser
    130                 135                 140

Ser Glu Val Gln Leu Gln Gln Ser Gly Ala Glu Leu Val Lys Pro Gly
145                 150                 155                 160

Ala Ser Val Lys Leu Ser Cys Thr Ala Ser Gly Phe Asn Ile Lys Asp
                165                 170                 175

Thr Tyr Ile His Phe Val Arg Gln Arg Pro Glu Gln Gly Leu Glu Trp
            180                 185                 190

Ile Gly Arg Ile Asp Pro Ala Asn Asp Asn Thr Leu Tyr Ala Ser Lys
        195                 200                 205

Phe Gln Gly Lys Ala Thr Ile Thr Ala Asp Thr Ser Ser Asn Thr Ala
    210                 215                 220

Tyr Met His Leu Ser Ser Leu Thr Ser Gly Asp Thr Ala Val Tyr Tyr
225                 230                 235                 240

Cys Gly Arg Gly Tyr Gly Tyr Tyr Val Phe Asp His Trp Gly Gln Gly
                245                 250                 255

Thr Thr Leu Thr Val Ser Ser Glu Pro Lys Ser Cys Asp Lys Thr His
            260                 265                 270

Thr Cys Pro Pro Cys Gly Gly Gly Ser Ser Gly Gly Gly Ser Gly Gly
```

```
                275                 280                 285
Gln Pro Arg Glu Pro Gln Val Tyr Thr Leu Pro Pro Ser Arg Asp Glu
    290                 295                 300

Leu Thr Lys Asn Gln Val Ser Leu Thr Cys Leu Val Lys Gly Phe Tyr
305                 310                 315                 320

Pro Ser Asp Ile Ala Val Glu Trp Glu Ser Asn Gly Gln Pro Glu Asn
                325                 330                 335

Asn Tyr Lys Thr Thr Pro Pro Val Leu Asp Ser Asp Gly Ser Phe Phe
            340                 345                 350

Leu Tyr Ser Lys Leu Thr Val Asp Lys Ser Arg Trp Gln Gln Gly Asn
        355                 360                 365

Val Phe Ser Cys Ser Val Met His Glu Ala Leu His Asn His Tyr Thr
370                 375                 380

Gln Lys Ser Leu Ser Leu Ser Pro Gly Lys
385                 390

<210> SEQ ID NO 17
<211> LENGTH: 1185
<212> TYPE: DNA
<213> ORGANISM: Artificial Sequence
<220> FEATURE:
<223> OTHER INFORMATION: Antigen binding construct or fragment thereof

<400> SEQUENCE: 17
atggagacag acaccctgct cctgtgggtg ctgctcctct gggtccctgg atccaccggc      60
gatgtccaga tcaaccaaag ccccagcttt ctggctgcct cccctggaga gacaatcacc     120
atcaattgcc ggaccagccg gagcatttcc cagtacctcg cctggtacca ggaaaagcct     180
ggcaagacca caagctgct gatctactcc ggctccacac tccagagcgg cattcccctcc    240 aggtttagcg atccggatc cggaaccgac ttcacactca ccatctccgg cctggagccc     300
gaggacttcg ccatgtatta ttgccagcag cacaatgaga ccccctgac cttcggcgct      360 ggcaccaagc tggagctgaa aggctccacc agcggaggcg gatccggagg aggaagcggc    420
ggcggaggct cctccgaagt gcagctgcaa cagagcggcg ccgaactggt gaagcctgga    480
gcttccgtga aactcagctg taccgccagc ggcttcaaca tcaaggatac ctacatccac    540
ttcgtgcggc aaaggcctga gcagggcctg gaatggatcg gcaggatcga ccccgccaac    600
gacaacaccc tctacgcctc caagttccaa ggcaaggcca caatcaccgc tgatacaagc    660
tccaacaccg cctacatgca cctcagctcc ctgaccagcg agacaccgc cgtgtactac     720 tgcgacggg gatacggcta ctatgtgttc gaccactggg gccaaggcac cacactcacc     780
gtgtcctccg agcccaagtc ctgcgacaag acacacacct gtcccccttg tggaggagga   840
tcctccggag gcggtccggg cggacagcct agggagcccc aggtgtacac actgcccct    900 tccagggacg aactcaccaa gaaccaggtg tccctgacct gcctggtgaa gggattctac    960
cccagcgaca tcgccgtgga gtgggagtcc aacggccaac ccgagaacaa ttacaagacc   1020
accccccctg tgctcgattc cgacggctcc ttcttcctgt actccaagct caccgtggac   1080 aagtccggt ggcaacaggg caatgtgttc tcctgcagcg tcatgcacga ggccctgcat    1140
aaccactaca cccagaaatc cctcagcctc tcccctggaa aatga                  1185

<210> SEQ ID NO 18
<211> LENGTH: 394
<212> TYPE: PRT
<213> ORGANISM: Artificial Sequence
<220> FEATURE:
```

<223> OTHER INFORMATION: Antigen binding construct or fragment thereof

<400> SEQUENCE: 18

```
Met Glu Thr Asp Thr Leu Leu Leu Trp Val Leu Leu Trp Val Pro
1               5                   10                  15
Gly Ser Thr Gly Glu Val Gln Leu Gln Gln Ser Gly Ala Glu Leu Val
            20                  25                  30
Lys Pro Gly Ala Ser Val Lys Leu Ser Cys Thr Ala Ser Gly Phe Asn
        35                  40                  45
Ile Lys Asp Thr Tyr Ile His Phe Val Arg Gln Arg Pro Glu Gln Gly
    50                  55                  60
Leu Glu Trp Ile Gly Arg Ile Asp Pro Ala Asn Asp Asn Thr Leu Tyr
65                  70                  75                  80
Ala Ser Lys Phe Gln Gly Lys Ala Thr Ile Thr Ala Asp Thr Ser Ser
                85                  90                  95
Asn Thr Ala Tyr Met His Leu Ser Ser Leu Thr Ser Gly Asp Thr Ala
            100                 105                 110
Val Tyr Tyr Cys Gly Arg Gly Tyr Gly Tyr Tyr Val Phe Asp His Trp
        115                 120                 125
Gly Gln Gly Thr Thr Leu Thr Val Ser Ser Gly Ser Thr Ser Gly Gly
130                 135                 140
Gly Ser Gly Gly Gly Ser Gly Gly Gly Ser Ser Asp Val Gln Ile
145                 150                 155                 160
Asn Gln Ser Pro Ser Phe Leu Ala Ala Ser Pro Gly Glu Thr Ile Thr
                165                 170                 175
Ile Asn Cys Arg Thr Ser Arg Ser Ile Ser Gln Tyr Leu Ala Trp Tyr
            180                 185                 190
Gln Glu Lys Pro Gly Lys Thr Asn Lys Leu Leu Ile Tyr Ser Gly Ser
        195                 200                 205
Thr Leu Gln Ser Gly Ile Pro Ser Arg Phe Ser Gly Ser Gly Ser Gly
    210                 215                 220
Thr Asp Phe Thr Leu Thr Ile Ser Gly Leu Glu Pro Glu Asp Phe Ala
225                 230                 235                 240
Met Tyr Tyr Cys Gln Gln His Asn Glu Asn Pro Leu Thr Phe Gly Ala
                245                 250                 255
Gly Thr Lys Leu Glu Leu Lys Glu Pro Lys Ser Cys Asp Lys Thr His
            260                 265                 270
Thr Cys Pro Pro Cys Gly Gly Gly Ser Gly Gly Gly Ser Gly Gly
        275                 280                 285
Gln Pro Arg Glu Pro Gln Val Tyr Thr Leu Pro Pro Ser Arg Asp Glu
    290                 295                 300
Leu Thr Lys Asn Gln Val Ser Leu Thr Cys Leu Val Lys Gly Phe Tyr
305                 310                 315                 320
Pro Ser Asp Ile Ala Val Glu Trp Glu Ser Asn Gly Gln Pro Glu Asn
                325                 330                 335
Asn Tyr Lys Thr Thr Pro Pro Val Leu Asp Ser Asp Gly Ser Phe Phe
            340                 345                 350
Leu Tyr Ser Lys Leu Thr Val Asp Lys Ser Arg Trp Gln Gln Gly Asn
        355                 360                 365
Val Phe Ser Cys Ser Val Met His Glu Ala Leu His Asn His Tyr Thr
    370                 375                 380
Gln Lys Ser Leu Ser Leu Ser Pro Gly Lys
385                 390
```

<210> SEQ ID NO 19
<211> LENGTH: 1185
<212> TYPE: DNA
<213> ORGANISM: Artificial Sequence
<220> FEATURE:
<223> OTHER INFORMATION: Antigen binding construct or fragment thereof

<400> SEQUENCE: 19

```
atggagaccg acacactcct gctctgggtg ctcctgctgt gggtgcctgg cagcacagga      60
gaagtgcagc tgcagcagtc cggcgccgaa ctcgtcaaac ccggagcctc cgtcaaactg     120
tcctgcacag ccagcggctt caacatcaag gacacctaca tccatttcgt gcggcaaagg     180
cctgaacagg gactcgagtg gatcggcagg atcgaccccg ccaacgacaa taccctctac     240
gcctccaagt tccagggaaa ggccaccatt accgccgaca catccagcaa caccgcctac     300
atgcacctca gctccctgac atccggcgac accgccgtgt actactgcgg cagggggctac     360
ggctactacg tgtttgacca ctggggccag ggaacaaccc tgaccgtgtc cagcggctcc     420
acctccggag gcggaagcgg cggaggatcc ggaggaggag gctcctccga cgtgcaaatc     480
aaccagtccc ctagcttcct ggccgctagc cctggcgaga caatcacaat caattgtcgg     540
accagccggt ccatctccca gtatctggcc tggtaccagg agaagcccgg caagacaaac     600
aagctgctca tctacagcgg cagcaccctc aatccggca tcccttcccg gtttagcggc     660
tccggatccg gaaccgactt taccctgacc atcagcggcc tggaacccga ggatttcgcc     720
atgtactact gccagcagca acgagaat ccctgacct ttggagccgg cacaaagctc     780
gagctgaagg agcccaagag ctgcgacaaa acccacacct gtcccccttg cggaggagga     840
tcctccggcg gcggaagcgg aggacaaccc agggagcccc aggtctacac cctgcctcct     900
agccgggacg aactgacaaa gaaccaggtg tccctgacct gtctcgtcaa gggcttctac     960
ccttccgaca tcgccgtcga gtgggaaagc aacggccagc ccgagaacaa ttacaagacc    1020
acaccccccg tcctggacag cgatggcagc ttcttcctct actccaagct gaccgtggac    1080
aagagccggt ggcaacaagg caacgtgttc tcctgcagcg tcatgcatga ggccctgcac    1140
aatcactaca cccagaagag cctgagcctc tccccccggca agtga               1185
```

<210> SEQ ID NO 20
<211> LENGTH: 394
<212> TYPE: PRT
<213> ORGANISM: Artificial Sequence
<220> FEATURE:
<223> OTHER INFORMATION: Antigen binding construct or fragment thereof

<400> SEQUENCE: 20

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Arg Thr Ser Arg Ser
        35                  40                  45

Ile Ser Gln Tyr Leu Ala Trp Tyr Gln Gln Lys Pro Gly Lys Val Pro
    50                  55                  60

Lys Leu Leu Ile Tyr Ser Gly Ser Thr Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Val Ala Thr Tyr Tyr Cys Gln Gln His Asn 100                 105                 110
Glu Asn Pro Leu Thr Phe Gly Gly Gly Thr Lys Val Glu Ile Lys Gly
            115                 120                 125

Ser Thr Ser Gly Gly Gly Ser Gly Gly Gly Ser Gly Gly Gly Gly Ser
130                 135                 140

Ser Gln Val Gln Leu Val Gln Ser Gly Ala Glu Val Lys Lys Pro Gly
145                 150                 155                 160

Ala Thr Val Lys Ile Ser Cys Lys Val Ser Gly Phe Asn Ile Lys Asp
                165                 170                 175

Thr Tyr Ile His Trp Val Gln Gln Ala Pro Gly Lys Gly Leu Glu Trp
            180                 185                 190

Met Gly Arg Ile Asp Pro Ala Asn Asp Asn Thr Leu Tyr Ala Ser Lys
        195                 200                 205

Phe Gln Gly Arg Val Thr Ile Thr Ala Asp Thr Ser Thr Asp Thr Ala
    210                 215                 220

Tyr Met Glu Leu Ser Ser Leu Arg Ser Glu Asp Thr Ala Val Tyr Tyr
225                 230                 235                 240

Cys Ala Arg Gly Tyr Gly Tyr Tyr Val Phe Asp His Trp Gly Gln Gly
                245                 250                 255

Thr Leu Val Thr Val Ser Ser Glu Pro Lys Ser Cys Asp Lys Thr His
            260                 265                 270

Thr Cys Pro Pro Cys Gly Gly Ser Gly Gly Gly Ser Gly Gly Gly Gly
        275                 280                 285

Gln Pro Arg Glu Pro Gln Val Tyr Thr Leu Pro Pro Ser Arg Asp Glu
    290                 295                 300

Leu Thr Lys Asn Gln Val Ser Leu Thr Cys Leu Val Lys Gly Phe Tyr
305                 310                 315                 320

Pro Ser Asp Ile Ala Val Glu Trp Glu Ser Asn Gly Gln Pro Glu Asn
                325                 330                 335

Asn Tyr Lys Thr Thr Pro Pro Val Leu Asp Ser Asp Gly Ser Phe Phe
            340                 345                 350

Leu Tyr Ser Lys Leu Thr Val Asp Lys Ser Arg Trp Gln Gln Gly Asn
        355                 360                 365

Val Phe Ser Cys Ser Val Met His Glu Ala Leu His Asn His Tyr Thr
    370                 375                 380

Gln Lys Ser Leu Ser Leu Ser Pro Gly Lys
385                 390

<210> SEQ ID NO 21
<211> LENGTH: 1185
<212> TYPE: DNA
<213> ORGANISM: Artificial Sequence
<220> FEATURE:
<223> OTHER INFORMATION: Antigen binding construct or fragment thereof

<400> SEQUENCE: 21
atggagacag acaccctcct gctgtgggtc ctgctgctgt gggtgcctgg cagcacagga      60
gacatccaaa tgacccagtc ccctagcagc ctcagcgctt ccgtcggaga cagggtcacc     120
atcacatgca ggacctccag gtccatcagc cagtatctgg cctggtatca gcagaaaccc     180
ggcaaggtgc ctaagctgct gatctacagc ggcagcacac tccagagcgg agtgcccagc     240
cggttttccg gaagcggatc cggaaccgac ttcaccctga ccatttccag cctgcaacct     300
gaagacgtgg ccacctacta ctgtcagcag cacaacgaga ccccctcac cttcggcgga     360 ggcaccaaag tcgagatcaa ggcagcacc agcggaggag gaagcggcgg aggctccgga     420

```
ggaggaggct cctcccaagt gcagctcgtc caaagcggcg ctgaggtgaa aaagcccggc      480
gccacagtca aatctcctg caaggtcagc ggcttcaaca tcaaggatac ctacatccac      540
tgggtgcaac aggcccccgg caaaggactc gaatggatgg gccggatcga ccctgctaac      600
gacaacacac tctacgcctc caagttccag ggcagggtga ccatcaccgc cgataccttcc    660 accgacacag cctacatgga gctgagcagc ctgaggtccg aggacaccgc cgtctattac     720
tgcgcccggg gatacggcta ctacgtgttt gaccattggg gacagggaac actcgtgacc     780
gtgagctccg agcccaagag ctgcgacaag acccacacat gtcctccttg cggaggaggc     840
agctccggag gcggatccgg cggacaacct agggagcccc aggtctatac cctgcccccc     900
agcagggacg agctgacaaa gaaccaggtc tccctgacct gcctggtgaa aggattctac     960
cccagcgaca tcgctgtcga atgggagtcc aacggccagc ccgagaacaa ctacaagaca     1020 acccccccg tgctggattc cgacggcagc ttcttcctct actccaagct gaccgtcgac      1080
aagtccaggt ggcagcaggg caacgtgttt tcctgctccg tgatgcatga ggccctgcac     1140
aaccactaca cccagaagtc cctgagcctc agccctggca agtga                     1185
```

<210> SEQ ID NO 22
<211> LENGTH: 394
<212> TYPE: PRT
<213> ORGANISM: Artificial Sequence
<220> FEATURE:
<223> OTHER INFORMATION: Antigen binding construct or fragment thereof

<400> SEQUENCE: 22

```
Met Glu Thr Asp Thr Leu Leu Leu Trp Val Leu Leu Leu Trp Val Pro
1               5                   10                  15

Gly Ser Thr Gly Gln Val Gln Leu Val Gln Ser Gly Ala Glu Val Lys
            20                  25                  30

Lys Pro Gly Ala Thr Val Lys Ile Ser Cys Lys Val Ser Gly Phe Asn
        35                  40                  45

Ile Lys Asp Thr Tyr Ile His Trp Val Gln Gln Ala Pro Gly Lys Gly
    50                  55                  60

Leu Glu Trp Met Gly Arg Ile Asp Pro Ala Asn Asp Asn Thr Leu Tyr
65                  70                  75                  80

Ala Ser Lys Phe Gln Gly Arg Val Thr Ile Thr Ala Asp Thr Ser Thr
                85                  90                  95

Asp Thr Ala Tyr Met Glu Leu Ser Ser Leu Arg Ser Glu Asp Thr Ala
            100                 105                 110

Val Tyr Tyr Cys Ala Arg Gly Tyr Gly Tyr Tyr Val Phe Asp His Trp
        115                 120                 125

Gly Gln Gly Thr Leu Val Thr Val Ser Ser Gly Ser Thr Ser Gly Gly
    130                 135                 140

Gly Ser Gly Gly Gly Ser Gly Gly Gly Ser Ser Asp Ile Gln Met
145                 150                 155                 160

Thr Gln Ser Pro Ser Ser Leu Ser Ala Ser Val Gly Asp Arg Val Thr
                165                 170                 175

Ile Thr Cys Arg Thr Ser Arg Ser Ile Ser Gln Tyr Leu Ala Trp Tyr
            180                 185                 190

Gln Gln Lys Pro Gly Lys Val Pro Lys Leu Leu Ile Tyr Ser Gly Ser
        195                 200                 205

Thr Leu Gln Ser Gly Val Pro Ser Arg Phe Ser Gly Ser Gly Ser Gly
    210                 215                 220
```

```
Thr Asp Phe Thr Leu Thr Ile Ser Ser Leu Gln Pro Glu Asp Val Ala
225                 230                 235                 240

Thr Tyr Tyr Cys Gln Gln His Asn Glu Asn Pro Leu Thr Phe Gly Gly
            245                 250                 255

Gly Thr Lys Val Glu Ile Lys Glu Pro Lys Ser Cys Asp Lys Thr His
        260                 265                 270

Thr Cys Pro Pro Cys Gly Gly Ser Ser Gly Gly Ser Gly Gly
    275                 280                 285

Gln Pro Arg Glu Pro Gln Val Tyr Thr Leu Pro Pro Ser Arg Asp Glu
    290                 295                 300

Leu Thr Lys Asn Gln Val Ser Leu Thr Cys Leu Val Lys Gly Phe Tyr
305                 310                 315                 320

Pro Ser Asp Ile Ala Val Glu Trp Glu Ser Asn Gly Gln Pro Glu Asn
            325                 330                 335

Asn Tyr Lys Thr Thr Pro Pro Val Leu Asp Ser Asp Gly Ser Phe Phe
        340                 345                 350

Leu Tyr Ser Lys Leu Thr Val Asp Lys Ser Arg Trp Gln Gln Gly Asn
    355                 360                 365

Val Phe Ser Cys Ser Val Met His Glu Ala Leu His Asn His Tyr Thr
370                 375                 380

Gln Lys Ser Leu Ser Leu Ser Pro Gly Lys
385                 390
```

<210> SEQ ID NO 23
<211> LENGTH: 1185
<212> TYPE: DNA
<213> ORGANISM: Artificial Sequence
<220> FEATURE:
<223> OTHER INFORMATION: Antigen binding construct or fragment thereof

<400> SEQUENCE: 23

```
atggagaccg atacactgct gctctgggtg ctgctgctgt gggtgcctgg aagcaccgga      60
caggtgcaac tggtccagtc cggcgccgag gtgaaaaagc tggcgccac cgtcaagatc     120
tcctgtaagg tgagcggctt caacatcaag gacacctaca tccactgggt gcagcaggct     180
cccggaaagg gactggagtg gatgggcagg atcgaccctg caatgacaa caccctctac     240
gccagcaagt tccaaggacg ggtgaccatc acagccgaca catccaccga cacagcctat     300
atggagctct ccagcctgag gtccgaggac accgccgtgt actactgtgc cagggggatac     360
ggctattacg tgttcgacca ctggggacag ggcaccctgg tgaccgtgag cagcggaagc     420
accagcggcg gaggcagcgg aggcggaagc ggcggcggcg gatcctccga cattcagatg     480
acccaatccc cctccagcct gtccgctagc gtgggagaca gggtgacaat cacatgtcgg     540
acctccaggt ccatcagcca atatctcgcc tggtatcagc agaagcccgg caaggtgccc     600
aagctcctga tctacagcgg ctccacctc caaagcggag tgccttcccg gtttagcgga     660
agcggcagcg gcacagactt taccctgaca atcagctccc tgcaacctga ggacgtcgcc     720
acatactact gccagcagca caacgagaac cctctcacct ttggcggcgg caccaaagtg     780
gagatcaagg agcccaaatc ctgcgacaag acacacacct gccccccttg tggaggaggc     840
agctccggcg gcggcagcgg cggacaaccc ggaaccctc aggtgtatac actcccccct     900
tccagggatg agctgaccaa gaaccaagtc tccctgacct gtctggtgaa aggcttctac     960
ccctccgaca tcgctgtcga gtgggagagc aacggccagc cgaaaacaa ctataagacc    1020
accccccccg tgctcgattc cgatggcagc ttcttcctgt actccaagct cacagtcgac    1080
```

```
aagagccggt ggcaacaggg caacgtcttc tcctgtagcg tcatgcacga ggccctccac    1140
aaccactaca cccagaagtc cctctccctg agcccggaa aatga                      1185
```

<210> SEQ ID NO 24
<211> LENGTH: 235
<212> TYPE: PRT
<213> ORGANISM: Homo sapiens

<400> SEQUENCE: 24

```
Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235
```

<210> SEQ ID NO 25
<211> LENGTH: 60
<212> TYPE: DNA
<213> ORGANISM: Artificial Sequence
<220> FEATURE:
<223> OTHER INFORMATION: Antigen binding construct or fragment thereof

<400> SEQUENCE: 25

```
atggaaaccg acaccctgct gctgtgggtg ctgctgctct gggtcccagg ctccaccggt    60
```

<210> SEQ ID NO 26
<211> LENGTH: 20
<212> TYPE: PRT
<213> ORGANISM: Artificial Sequence
<220> FEATURE:
<223> OTHER INFORMATION: Antigen binding construct or fragment thereof

<400> SEQUENCE: 26

Met Glu Thr Asp Thr Leu Leu Leu Trp Val Leu Leu Leu Trp Val Pro
1               5                   10                  15

Gly Ser Thr Gly
            20

<210> SEQ ID NO 27
<211> LENGTH: 15
<212> TYPE: DNA
<213> ORGANISM: Artificial Sequence
<220> FEATURE:
<223> OTHER INFORMATION: Antigen binding construct or fragment thereof

<400> SEQUENCE: 27
agtggtggag gaggc                                                    15

<210> SEQ ID NO 28
<211> LENGTH: 5
<212> TYPE: PRT
<213> ORGANISM: Artificial Sequence
<220> FEATURE:
<223> OTHER INFORMATION: Antigen binding construct or fragment thereof

<400> SEQUENCE: 28

Ser Gly Gly Gly Gly
1               5

<210> SEQ ID NO 29
<211> LENGTH: 24
<212> TYPE: DNA
<213> ORGANISM: Artificial Sequence
<220> FEATURE:
<223> OTHER INFORMATION: Antigen binding construct or fragment thereof

<400> SEQUENCE: 29
ggcggaggga gtggcggagg cggc                                          24

<210> SEQ ID NO 30
<211> LENGTH: 8
<212> TYPE: PRT
<213> ORGANISM: Artificial Sequence
<220> FEATURE:
<223> OTHER INFORMATION: Antigen binding construct or fragment thereof

<400> SEQUENCE: 30

Gly Gly Gly Ser Gly Gly Gly Gly
1               5

<210> SEQ ID NO 31
<211> LENGTH: 9
<212> TYPE: DNA
<213> ORGANISM: Artificial Sequence
<220> FEATURE:
<223> OTHER INFORMATION: Antigen binding construct or fragment thereof

<400> SEQUENCE: 31 ggcggctgc                                                            9

<210> SEQ ID NO 32
<211> LENGTH: 3
<212> TYPE: PRT
<213> ORGANISM: Artificial Sequence
<220> FEATURE:
<223> OTHER INFORMATION: Antigen binding construct or fragment thereof

<400> SEQUENCE: 32

Gly Gly Cys

<210> SEQ ID NO 33
<211> LENGTH: 60
<212> TYPE: DNA
<213> ORGANISM: Artificial Sequence
<220> FEATURE:
<223> OTHER INFORMATION: Antigen binding construct or fragment thereof

<400> SEQUENCE: 33

```
atggaaaccg acaccctgct gctgtgggtg ctgctgctct gggtcccagg ctccaccggt    60
```

<210> SEQ ID NO 34
<211> LENGTH: 20
<212> TYPE: PRT
<213> ORGANISM: Artificial Sequence
<220> FEATURE:
<223> OTHER INFORMATION: Antigen binding construct or fragment thereof

<400> SEQUENCE: 34

Met Glu Thr Asp Thr Leu Leu Leu Trp Val Leu Leu Leu Trp Val Pro
1               5                  10                  15

Gly Ser Thr Gly
            20

<210> SEQ ID NO 35
<211> LENGTH: 54
<212> TYPE: DNA
<213> ORGANISM: Artificial Sequence
<220> FEATURE:
<223> OTHER INFORMATION: Antigen binding construct or fragment thereof

<400> SEQUENCE: 35

```
ggctccacat ccggcggagg ctctggcggt ggatctggcg gaggcggctc atcc           54
```

<210> SEQ ID NO 36
<211> LENGTH: 18
<212> TYPE: PRT
<213> ORGANISM: Artificial Sequence
<220> FEATURE:
<223> OTHER INFORMATION: Antigen binding construct or fragment thereof

<400> SEQUENCE: 36

Gly Ser Thr Ser Gly Gly Gly Ser Gly Gly Gly Ser Gly Gly Gly Gly
1               5                  10                  15

Ser Ser

<210> SEQ ID NO 37
<211> LENGTH: 393
<212> TYPE: DNA
<213> ORGANISM: Artificial Sequence
<220> FEATURE:
<223> OTHER INFORMATION: Antigen binding construct or fragment thereof

<400> SEQUENCE: 37

```
gagcctaagt cctgcgacaa gacccacacc tgtcccccctt gcggcggagg aagcagcgga    60
ggcggatccg gtggccagcc tcgggagcct caggtgtaca ccctgcctcc ctcccgggac   120
gagctgacca gaaccaggt gtccctgacc tgtctggtca aggcttcta cccttccgat     180
atcgccgtgg agtgggagtc caacggccag cctgagaaca actacaagac cacccctcct   240
gtgctggact ccgacggctc cttcttcctg tactccaagc tcacagtgga taagtcccgg   300
tggcagcagg gcaacgtgtt ctcctgctcc gtgatgcacg aggccctgca caaccactat   360
```
acccagaagt ccctgtccct gtctcctggc aag                                   393

<210> SEQ ID NO 38
<211> LENGTH: 131
<212> TYPE: PRT
<213> ORGANISM: Artificial Sequence
<220> FEATURE:
<223> OTHER INFORMATION: Antigen binding construct or fragment thereof

<400> SEQUENCE: 38

Glu Pro Lys Ser Cys Asp Lys Thr His Thr Cys Pro Pro Cys Gly Gly
1               5                   10                  15

Gly Ser Ser Gly Gly Gly Ser Gly Gly Gln Pro Arg Glu Pro Gln Val
            20                  25                  30

Tyr Thr Leu Pro Pro Ser Arg Asp Glu Leu Thr Lys Asn Gln Val Ser
        35                  40                  45

Leu Thr Cys Leu Val Lys Gly Phe Tyr Pro Ser Asp Ile Ala Val Glu
    50                  55                  60

Trp Glu Ser Asn Gly Gln Pro Glu Asn Asn Tyr Lys Thr Thr Pro Pro
65                  70                  75                  80

Val Leu Asp Ser Asp Gly Ser Phe Phe Leu Tyr Ser Lys Leu Thr Val
                85                  90                  95

Asp Lys Ser Arg Trp Gln Gln Gly Asn Val Phe Ser Cys Ser Val Met
            100                 105                 110

His Glu Ala Leu His Asn His Tyr Thr Gln Lys Ser Leu Ser Leu Ser
        115                 120                 125

Pro Gly Lys
    130

<210> SEQ ID NO 39
<211> LENGTH: 321
<212> TYPE: DNA
<213> ORGANISM: Murine

<400> SEQUENCE: 39
gatgtccaga taaaccagtc tccatctttt cttgctgcgt ctcctggaga aaccattact    60
ataaattgca ggacaagtag gagtattagt caatatttag cctggtatca agagaaacct   120
gggaaaacta ataagcttct tatctactct ggatccactc tgcaatctgg aattccatca   180
aggttcagtg gcagtggatc tggtacagat ttcactctca ccatcagtgg cctggagcct   240
gaagattttg caatgtatta ctgtcaacag cataatgaaa acccgctcac gttcggtgct   300
gggaccaagc tggagctgaa g                                             321

<210> SEQ ID NO 40
<211> LENGTH: 107
<212> TYPE: PRT
<213> ORGANISM: Murine

<400> SEQUENCE: 40

Asp Val Gln Ile Asn Gln Ser Pro Ser Phe Leu Ala Ala Ser Pro Gly
1               5                   10                  15

Glu Thr Ile Thr Ile Asn Cys Arg Thr Ser Arg Ser Ile Ser Gln Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

```
Ser Gly Ser Gly Thr Asp Phe Thr Leu Thr Ile Ser Gly Leu Glu Pro
 65                  70                  75                  80

Glu Asp Phe Ala Met Tyr Tyr Cys Gln Gln His Asn Glu Asn Pro Leu
                 85                  90                  95

Thr Phe Gly Ala Gly Thr Lys Leu Glu Leu Lys
            100                 105

<210> SEQ ID NO 41
<211> LENGTH: 321
<212> TYPE: DNA
<213> ORGANISM: Artificial Sequence
<220> FEATURE:
<223> OTHER INFORMATION: Antigen binding construct or fragment thereof

<400> SEQUENCE: 41
gacgtccaga taacccagtc tccatcctcc ctgtctgcat ctgtaggaga cagagtcacc      60
atcacttgca ggacaagtag gagtattagt caatatttag cctggtatca gcagaaacca     120
gggaaagttc ctaagctcct gatctattct ggatccactc tgcaatctgg agtcccatct     180
cggttcagtg gcagtggatc tgggacagat ttcactctca ccatcagcag cctgcagcct     240
gaagatgttg caacttatta ctgtcaacag cataatgaaa acccgctcac gttcggcgga     300
gggaccaagg tggagatcaa a                                               321

<210> SEQ ID NO 42
<211> LENGTH: 107
<212> TYPE: PRT
<213> ORGANISM: Artificial Sequence
<220> FEATURE:
<223> OTHER INFORMATION: Antigen binding construct or fragment thereof

<400> SEQUENCE: 42

Asp Val Gln Ile Thr Gln Ser Pro Ser Ser Leu Ser Ala Ser Val Gly
  1               5                  10                  15

Asp Arg Val Thr Ile Thr Cys Arg Thr Ser Arg Ser Ile Ser Gln Tyr
                 20                  25                  30

Leu Ala Trp Tyr Gln Gln Lys Pro Gly Lys Val Pro Lys Leu Leu Ile
             35                  40                  45

Tyr Ser Gly Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Gln His Asn Glu Asn Pro Leu
                 85                  90                  95

Thr Phe Gly Gly Gly Thr Lys Val Glu Ile Lys
            100                 105

<210> SEQ ID NO 43
<211> LENGTH: 354
<212> TYPE: DNA
<213> ORGANISM: Murine

<400> SEQUENCE: 43
gaggtccagc tgcagcagtc tggggcagag cttgtgaagc caggggcctc agtcaagttg      60
tcctgcacag cttctggctt caacattaaa gacacctata cacttcgt gaggcagagg      120 cctgaacagg gcctggagtg gattggaagg attgatcctg cgaatgataa tactttatat     180
gcctcaaagt tccagggcaa ggccactata acagcagaca catcatccaa cacagcctac     240
atgcacctct gcagcctgac atctggggac actgccgtct attactgtgg tagaggttat     300
```

```
ggttactacg tatttgacca ctggggccaa ggcaccactc tcacagtctc ctca          354
```

<210> SEQ ID NO 44
<211> LENGTH: 118
<212> TYPE: PRT
<213> ORGANISM: Murine

<400> SEQUENCE: 44

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Phe Val Arg Gln Arg Pro Glu Gln Gly Leu Glu Trp Ile
        35                  40                  45

Gly Arg Ile Asp Pro Ala Asn Asp Asn Thr Leu Tyr Ala Ser Lys Phe
    50                  55                  60

Gln Gly Lys Ala Thr Ile Thr Ala Asp Thr Ser Ser Asn Thr Ala Tyr
65                  70                  75                  80

Met His Leu Cys Ser Leu Thr Ser Gly Asp Thr Ala Val Tyr Tyr Cys
                85                  90                  95

Gly Arg Gly Tyr Gly Tyr Tyr Val Phe Asp His Trp Gly Gln Gly Thr
            100                 105                 110

Thr Leu Thr Val Ser Ser
        115
```

<210> SEQ ID NO 45
<211> LENGTH: 354
<212> TYPE: DNA
<213> ORGANISM: Artificial Sequence
<220> FEATURE:
<223> OTHER INFORMATION: Antigen binding construct or fragment thereof

<400> SEQUENCE: 45

```
gaagtgcagc tggtggaaag cggcggcggc ctggtgcagc cgggcggcag cctgcgcctg    60
agctgcgcgg cgagcggctt taacattaaa gataccctata ttcatttttgt gcgccaggcg   120 ccgggcaaag cctggaatg gattggccgc attgatccgg cgaacgataa caccctgtat     180
gcgagcaaat ttcagggcaa agcgaccatt agcgcggata ccagcaaaaa caccgcgtat    240
ctgcagatga acagcctgcg cgcgggagat accgcggtgt attattgcgg ccgcggctat    300
ggctattatg tgtttgatca ttggggccag ggcaccctgg tgaccgtgag cagc          354
```

<210> SEQ ID NO 46
<211> LENGTH: 118
<212> TYPE: PRT
<213> ORGANISM: Artificial Sequence
<220> FEATURE:
<223> OTHER INFORMATION: Antigen binding construct or fragment thereof

<400> SEQUENCE: 46

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Phe Val Arg Gln Ala Pro Gly Lys Gly Leu Glu Trp Ile
        35                  40                  45

Gly Arg Ile Asp Pro Ala Asn Asp Asn Thr Leu Tyr Ala Ser Lys Phe
    50                  55                  60
```

```
Gln Gly Lys Ala Thr Ile Ser Ala Asp Thr Ser Lys Asn Thr Ala Tyr
 65                  70                  75                  80

Leu Gln Met Asn Ser Leu Arg Ala Gly Asp Thr Ala Val Tyr Tyr Cys
                 85                  90                  95

Gly Arg Gly Tyr Gly Tyr Tyr Val Phe Asp His Trp Gly Gln Gly Thr
            100                 105                 110

Leu Val Thr Val Ser Ser
            115

<210> SEQ ID NO 47
<211> LENGTH: 354
<212> TYPE: DNA
<213> ORGANISM: Artificial Sequence
<220> FEATURE:
<223> OTHER INFORMATION: Antigen binding construct or fragment thereof

<400> SEQUENCE: 47
gaagtgcagc tggtggaaag cggcggcggc ctggtgcagc cgggcggcag cctgcgcctg      60
agctgcgcgg cgagcggctt taacattaaa gataccttata ttcattttgt gcgccaggcg    120
ccgggcaaag gcctggaatg gattggccgc attgatccgg cgaacgataa caccctgtat     180
gcgagcaaat ttcagggcaa agcgaccatt agcgcggata ccagcaaaaa caccgcgtat     240
ctgcagatga acagcctgcg cgcggaagat accgcggtgt attattgcgg ccgcggctat     300
ggctattatg tgtttgatca ttggggccag ggcacccttgg tgaccgtgag cagc          354

<210> SEQ ID NO 48
<211> LENGTH: 118
<212> TYPE: PRT
<213> ORGANISM: Artificial Sequence
<220> FEATURE:
<223> OTHER INFORMATION: Antigen binding construct or fragment thereof

<400> SEQUENCE: 48

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
             20                  25                  30

Tyr Ile His Phe Val Arg Gln Ala Pro Gly Lys Gly Leu Glu Trp Ile
         35                  40                  45

Gly Arg Ile Asp Pro Ala Asn Asp Asn Thr Leu Tyr Ala Ser Lys Phe
     50                  55                  60

Gln Gly Lys Ala Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Gly Arg Gly Tyr Gly Tyr Tyr Val Phe Asp His Trp Gly Gln Gly Thr
            100                 105                 110

Leu Val Thr Val Ser Ser
            115

<210> SEQ ID NO 49
<211> LENGTH: 354
<212> TYPE: DNA
<213> ORGANISM: Artificial Sequence
<220> FEATURE:
<223> OTHER INFORMATION: Antigen binding construct or fragment thereof

<400> SEQUENCE: 49
caggtgcagc tggtgcagag cggcgcggaa gtgaaaaaac cgggcgcgac cgtgaaaatt      60
```

```
agctgcaaag tgagcggctt taacattaaa gatacctata ttcattttgt gcagcaggcg    120
ccgggcaaag gcctggaatg gattggccgc attgatccgg cgaacgataa cacccctgtat   180 gcgagcaaat ttcagggcaa agcgaccatt accgcggata ccagcaccga taccgcgtat    240
atggaactga gcagcctgcg cagcggagat accgcggtgt attattgcgg ccgcggctat    300
ggctattatg tgtttgatca ttggggccag ggcaccctgg tgaccgtgag cagc          354
```

<210> SEQ ID NO 50
<211> LENGTH: 118
<212> TYPE: PRT
<213> ORGANISM: Artificial Sequence
<220> FEATURE:
<223> OTHER INFORMATION: Antigen binding construct or fragment thereof

<400> SEQUENCE: 50

```
Gln Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Thr
            20                  25                  30

Tyr Ile His Phe Val Gln Gln Ala Pro Gly Lys Gly Leu Glu Trp Ile
        35                  40                  45

Gly Arg Ile Asp Pro Ala Asn Asp Asn Thr Leu Tyr Ala Ser Lys Phe
    50                  55                  60

Gln Gly Lys Ala Thr Ile Thr Ala Asp Thr Ser Thr Asp Thr Ala Tyr
65                  70                  75                  80

Met Glu Leu Ser Ser Leu Arg Ser Gly Asp Thr Ala Val Tyr Tyr Cys
                85                  90                  95

Gly Arg Gly Tyr Gly Tyr Tyr Val Phe Asp His Trp Gly Gln Gly Thr
            100                 105                 110

Leu Val Thr Val Ser Ser
        115
```

<210> SEQ ID NO 51
<211> LENGTH: 354
<212> TYPE: DNA
<213> ORGANISM: Artificial Sequence
<220> FEATURE:
<223> OTHER INFORMATION: Antigen binding construct or fragment thereof

<400> SEQUENCE: 51

```
caggtgcagc tggtgcagag cggcgcggaa gtgaaaaaac cgggcgcgac cgtgaaaatt    60
agctgcaaag tgagcggctt taacattaaa gatacctata ttcattttgt gcagcaggcg   120
ccgggcaaag gcctggaatg gattggccgc attgatccgg cgaacgataa cacccctgtat  180 gcgagcaaat ttcagggcaa agcgaccatt accgcggata ccagcaccga taccgcgtat   240
atggaactga gcagcctgcg cagcgaagat accgcggtgt attattgcgg ccgcggctat   300
ggctattatg tgtttgatca ttggggccag ggcaccctgg tgaccgtgag cagc         354
```

<210> SEQ ID NO 52
<211> LENGTH: 117
<212> TYPE: PRT
<213> ORGANISM: Artificial Sequence
<220> FEATURE:
<223> OTHER INFORMATION: Antigen binding construct or fragment thereof

<400> SEQUENCE: 52

```
Gln Val Gln Leu Val Gln Ser Gly Ala Glu Val Lys Lys Pro Gly Ala
1               5                   10                  15
```

Thr Val Lys Ile Ser Cys Lys Val Ser Gly Phe Asn Ile Lys Asp Thr
            20                  25                  30

Tyr Ile His Phe Val Gln Gln Ala Pro Gly Lys Gly Leu Glu Trp Ile
        35                  40                  45

Gly Arg Ile Asp Pro Ala Asn Asp Asn Thr Leu Tyr Ala Ser Lys Phe
50                  55                  60

Gln Gly Lys Ala Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Gly Arg Gly Tyr Gly Tyr Val Phe Asp His Trp Gly Gln Gly Thr
            100                 105                 110

Leu Val Thr Val Ser
        115

<210> SEQ ID NO 53
<211> LENGTH: 23
<212> TYPE: PRT
<213> ORGANISM: Artificial Sequence
<220> FEATURE:
<223> OTHER INFORMATION: Antigen binding construct or fragment thereof

<400> SEQUENCE: 53

Glu Pro Lys Ser Cys Asp Lys Thr His Thr Cys Pro Pro Cys Pro Ala
1               5                   10                  15

Pro Glu Leu Leu Gly Gly Pro
            20

<210> SEQ ID NO 54
<211> LENGTH: 25
<212> TYPE: PRT
<213> ORGANISM: Artificial Sequence
<220> FEATURE:
<223> OTHER INFORMATION: Antigen binding construct or fragment thereof

<400> SEQUENCE: 54

Glu Pro Lys Ser Cys Asp Lys Thr His Thr Cys Pro Pro Cys Pro Gly
1               5                   10                  15

Gly Gly Ser Ser Gly Gly Gly Ser Gly
            20                  25

<210> SEQ ID NO 55
<211> LENGTH: 19
<212> TYPE: PRT
<213> ORGANISM: Artificial Sequence
<220> FEATURE:
<223> OTHER INFORMATION: Antigen binding construct or fragment thereof

<400> SEQUENCE: 55

Glu Arg Lys Cys Cys Val Glu Cys Pro Pro Cys Pro Ala Pro Pro Val
1               5                   10                  15

Ala Gly Pro

<210> SEQ ID NO 56
<211> LENGTH: 70
<212> TYPE: PRT
<213> ORGANISM: Artificial Sequence
<220> FEATURE:
<223> OTHER INFORMATION: Antigen binding construct or fragment thereof

<400> SEQUENCE: 56

```
Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
            35                  40                  45

Pro Lys Ser Cys Asp Thr Pro Pro Cys Pro Arg Cys Pro Ala Pro
        50                  55                  60

Glu Leu Leu Gly Gly Pro
65              70

<210> SEQ ID NO 57
<211> LENGTH: 25
<212> TYPE: PRT
<213> ORGANISM: Artificial Sequence
<220> FEATURE:
<223> OTHER INFORMATION: Antigen binding construct or fragment thereof

<400> SEQUENCE: 57

Glu Leu Lys Thr Pro Leu Gly Asp Thr Thr His Thr Cys Pro Arg Cys
1               5                   10                  15

Pro Ala Pro Glu Leu Leu Gly Gly Pro
            20                  25

<210> SEQ ID NO 58
<211> LENGTH: 23
<212> TYPE: PRT
<213> ORGANISM: Artificial Sequence
<220> FEATURE:
<223> OTHER INFORMATION: Antigen binding construct or fragment thereof

<400> SEQUENCE: 58

Glu Pro Lys Ser Cys Asp Thr Pro Pro Cys Pro Arg Cys Pro Ala
1               5                   10                  15

Pro Glu Leu Leu Gly Gly Pro
            20

<210> SEQ ID NO 59
<211> LENGTH: 20
<212> TYPE: PRT
<213> ORGANISM: Artificial Sequence
<220> FEATURE:
<223> OTHER INFORMATION: Antigen binding construct or fragment thereof

<400> SEQUENCE: 59

Glu Ser Lys Tyr Gly Pro Pro Cys Pro Ser Cys Pro Ala Pro Glu Phe
1               5                   10                  15

Leu Gly Gly Pro
            20

<210> SEQ ID NO 60
<211> LENGTH: 20
<212> TYPE: PRT
<213> ORGANISM: Artificial Sequence
<220> FEATURE:
<223> OTHER INFORMATION: Antigen binding construct or fragment thereof

<400> SEQUENCE: 60

Glu Ser Lys Tyr Gly Pro Pro Cys Pro Pro Cys Pro Ala Pro Glu Phe
1               5                   10                  15

Leu Gly Gly Pro
            20
```

```
<210> SEQ ID NO 61
<211> LENGTH: 15
<212> TYPE: DNA
<213> ORGANISM: Artificial Sequence
<220> FEATURE:
<223> OTHER INFORMATION: Restriction site

<400> SEQUENCE: 61
tctagagccg ccacc                                                    15

<210> SEQ ID NO 62
<211> LENGTH: 15
<212> TYPE: DNA
<213> ORGANISM: Artificial Sequence
<220> FEATURE:
<223> OTHER INFORMATION: Restriction site

<400> SEQUENCE: 62
tctagagccg ccacc                                                    15

<210> SEQ ID NO 63
<211> LENGTH: 6
<212> TYPE: DNA
<213> ORGANISM: Artificial Sequence
<220> FEATURE:
<223> OTHER INFORMATION: Restriction site

<400> SEQUENCE: 63 aagctt                                                               6

<210> SEQ ID NO 64
<211> LENGTH: 6
<212> TYPE: DNA
<213> ORGANISM: Artificial Sequence
<220> FEATURE:
<223> OTHER INFORMATION: Restriction site

<400> SEQUENCE: 64 aagctt                                                               6

<210> SEQ ID NO 65
<211> LENGTH: 15
<212> TYPE: DNA
<213> ORGANISM: Artificial Sequence
<220> FEATURE:
<223> OTHER INFORMATION: Restriction site

<400> SEQUENCE: 65
tctagagccg ccacc                                                    15

<210> SEQ ID NO 66
<211> LENGTH: 6
<212> TYPE: DNA
<213> ORGANISM: Artificial Sequence
<220> FEATURE:
<223> OTHER INFORMATION: Restriction site

<400> SEQUENCE: 66 aagctt                                                               6

<210> SEQ ID NO 67
<211> LENGTH: 15
<212> TYPE: DNA
<213> ORGANISM: Artificial Sequence
<220> FEATURE:
<223> OTHER INFORMATION: Restriction site
```

```
<400> SEQUENCE: 67
tctagagccg ccacc                                                    15

<210> SEQ ID NO 68
<211> LENGTH: 6
<212> TYPE: DNA
<213> ORGANISM: Artificial Sequence
<220> FEATURE:
<223> OTHER INFORMATION: Restriction site

<400> SEQUENCE: 68 aagctt                                                               6

<210> SEQ ID NO 69
<211> LENGTH: 15
<212> TYPE: DNA
<213> ORGANISM: Artificial Sequence
<220> FEATURE:
<223> OTHER INFORMATION: Restriction site

<400> SEQUENCE: 69
tctagagccg ccacc                                                    15

<210> SEQ ID NO 70
<211> LENGTH: 6
<212> TYPE: DNA
<213> ORGANISM: Artificial Sequence
<220> FEATURE:
<223> OTHER INFORMATION: Restriction site

<400> SEQUENCE: 70 aagctt                                                               6

<210> SEQ ID NO 71
<211> LENGTH: 15
<212> TYPE: DNA
<213> ORGANISM: Artificial Sequence
<220> FEATURE:
<223> OTHER INFORMATION: Restriction site

<400> SEQUENCE: 71
tctagagccg ccacc                                                    15

<210> SEQ ID NO 72
<211> LENGTH: 6
<212> TYPE: DNA
<213> ORGANISM: Artificial Sequence
<220> FEATURE:
<223> OTHER INFORMATION: Restriction site

<400> SEQUENCE: 72 aagctt                                                               6

<210> SEQ ID NO 73
<211> LENGTH: 15
<212> TYPE: DNA
<213> ORGANISM: Artificial Sequence
<220> FEATURE:
<223> OTHER INFORMATION: Restriction site

<400> SEQUENCE: 73
tctagagccg ccacc                                                    15

<210> SEQ ID NO 74
```

```
<211> LENGTH: 6
<212> TYPE: DNA
<213> ORGANISM: Artificial Sequence
<220> FEATURE:
<223> OTHER INFORMATION: Restriction site

<400> SEQUENCE: 74 aagctt                                                              6

<210> SEQ ID NO 75
<211> LENGTH: 15
<212> TYPE: DNA
<213> ORGANISM: Artificial Sequence
<220> FEATURE:
<223> OTHER INFORMATION: Restriction site

<400> SEQUENCE: 75
tctagagccg ccacc                                                   15

<210> SEQ ID NO 76
<211> LENGTH: 6
<212> TYPE: DNA
<213> ORGANISM: Artificial Sequence
<220> FEATURE:
<223> OTHER INFORMATION: Restriction site

<400> SEQUENCE: 76 aagctt                                                              6

<210> SEQ ID NO 77
<211> LENGTH: 759
<212> TYPE: DNA
<213> ORGANISM: Artificial Sequence
<220> FEATURE:
<223> OTHER INFORMATION: Antigen binding construct or fragment thereof

<400> SEQUENCE: 77
atggagaccg atacactgct gctgtgggtg ctgctgctct gggtccctgg cagcacagga     60
gacatccaga tgacacagag ccctagctcc ctgagcgctt ccgtgggaga tagggtgacc    120
atcacatgcc ggacctccag gtccatctcc cagtacctgg cctggtacca gcagaagccc    180
ggcaaggtgc ccaagctgct catctatagc ggcagcaccc tgcagagcgg agtgccttcc    240
cggttttccg gatccggctc cggcacagac tttaccctga ccatctccag cctgcagcct    300
gaggatgtcg ccacctacta ctgccaacag cacaacgaga ccccctgac cttcggcggc     360 ggaaccaagg tcgagatcaa gtccggagga ggaggccaag tgcagctggt ccaatccggc    420
gccgaagtga aaaagcccgg cgccaccgtg aagatcagct gcaaggtgtc cggcttcaac    480
atcaaggaca cctatatcca ctgggtccag caagcccccg gaaaaggcct ggagtggatg    540
ggacggattg accccgccaa cgacaacaca ctctatgcct ccaagttcca gggcagggtg    600
acaatcaccg ccgacaccag caccgacaca gcttatatgg agctgtcctc cctccggtcc    660
gaggataccg ccgtctacta ctgcgccagg ggctacggct actacgtgtt tgaccactgg    720
ggccagggca ccctggtgac agtgtccagc ggaggctgc                          759

<210> SEQ ID NO 78
<211> LENGTH: 759
<212> TYPE: DNA
<213> ORGANISM: Artificial Sequence
<220> FEATURE:
<223> OTHER INFORMATION: Antigen binding construct or fragment thereof

<400> SEQUENCE: 78
```

```
atggagaccg acaccctgct gctctgggtc ctcctgctgt gggtgcctgg cagcacagga    60
caggtgcaac tggtgcagag cggcgccgag gtcaagaaac tggcgccac cgtgaagatc    120 agctgcaagg tgtccggctt caacatcaag gacacctaca tccactgggt ccaacaagcc   180
cccggaaagg gcctggaatg gatgggccgg attgaccccg ccaacgacaa caccctctat   240
gccagcaagt tccagggcag ggtcaccatc accgccgaca ccagcaccga caccgcctac   300
atggagctga gcagcctgcg gagcgaagac accgccgtgt actactgcgc caggggctac   360
ggctactacg tcttcgacca ttggggacag ggcaccctcg tgacagtgtc cagctccggc   420
ggaggaggag atatccagat gacccagagc ccttccagcc tgtccgcttc cgtgggagat   480
cgggtgacca tcacatgcag gacctccagg tccatctccc agtacctggc ctggtaccaa   540
cagaagcccg gcaaggtgcc caagctgctg atctacagcg gcagcacact gcaatccggc   600
gtcccttccc ggttttccgg atccggatcc ggcaccgact caccctgac catcagctcc    660 ctgcaacccg aggacgtggc cacctactac tgtcagcagc acaacgagaa ccccctcacc   720
tttggcggcg gaaccaaggt cgagatcaag ggcggctgc                           759
```

<210> SEQ ID NO 79  
<211> LENGTH: 22  
<212> TYPE: PRT  
<213> ORGANISM: Artificial Sequence  
<220> FEATURE:  
<223> OTHER INFORMATION: Antigen binding construct or fragment thereof

<400> SEQUENCE: 79

```
Glu Arg Lys Cys Cys Val Glu Cys Pro Pro Cys Pro Gly Gly Gly Ser
1               5                   10                  15

Ser Gly Gly Gly Ser Gly
            20
```

<210> SEQ ID NO 80  
<211> LENGTH: 107  
<212> TYPE: PRT  
<213> ORGANISM: Artificial Sequence  
<220> FEATURE:  
<223> OTHER INFORMATION: Antigen binding construct or fragment thereof

<400> SEQUENCE: 80

```
Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
                100                 105
```

<210> SEQ ID NO 81  
<211> LENGTH: 107  
<212> TYPE: PRT  
<213> ORGANISM: Artificial Sequence

```
<220> FEATURE:
<223> OTHER INFORMATION: Antigen binding construct or fragment thereof

<400> SEQUENCE: 81

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

ANTIGEN BINDING CONSTRUCTS TO CD8

CROSS-REFERENCE TO RELATED APPLICATIONS

The present application is the U.S. national phase entry under 35 U.S.C. § 371 of PCT/US2014/022782, filed Mar. 10, 2014, which claims the benefit of U.S. Provisional Application No. 61/780,286, filed Mar. 13, 2013, which is hereby incorporated by reference in its entirety.

REFERENCE TO SEQUENCE LISTING, TABLE, OR COMPUTER PROGRAM LISTING

The present application is being filed along with a Sequence Listing in electronic format. The Sequence Listing is provided as a file entitled SeqListIGNAB014WO.txt, created on Feb. 28, 2014, which is 68,230 bytes in size. The information in the electronic format of the Sequence Listing is incorporated herein by reference in its entirety.

FIELD

Embodiments described herein relate generally to antigen binding constructs, such as antibodies, including antibody fragments, that bind to CD8, (such as minibodies, cys-diabodies, scFv), as well as methods for their use.

BACKGROUND

CD8 (cluster of differentiation 8) is a transmembrane glycoprotein which is a specific marker for a subclass of T-cells (which includes cytotoxic T-cells). CD8 assembles as either a heterodimer of the CD8 alpha and CD8 beta subunits or a CD8 alpha homodimer. The assembled dimeric CD8 complex acts as a co-receptor together with the T-cell receptor (TCR) to recognize antigen presentation by MHC class I cells. CD8 plays a role in the development of T-cells and activation of mature T-cells. Changes in T-cell localization can reflect the progression of an immune response and can occur over time.

SUMMARY

Some embodiments provided herein relate to antigen binding constructs, such as antibodies, including antibody fragments, that include a HCDR1 ("heavy chain complementary determining region 1") of a HCDR1 sequence in SEQ ID NO: 3 or 6; a HCDR2 ("heavy chain complementary determining region 2") of a HCDR2 sequence in SEQ ID NO: 3 or 6; a HCDR3 ("heavy chain complementary determining region 3") of a HCDR3 sequence in SEQ ID NO: 3 or 6; a LCDR1 ("light chain complementary determining region 1") of a LCDR1 sequence in SEQ ID NO: 9; a LCDR2 ("light chain complementary determining region 2") of a LCDR2 sequence in SEQ ID NO: 9; and a LCDR3 ("light chain complementary determining region 3") of a LCDR3 sequence in SEQ ID NO: 9). In some embodiments, the antigen binding construct binds specifically to CD8. In some embodiments, the antigen binding construct includes a detectable marker as described herein. In some embodiments, the antigen binding construct includes a therapeutic agent as described herein.

Some embodiments provided herein relate to a humanized cys-diabody that binds to CD8. The humanized cys-diabody can include a polypeptide that comprises from N-terminus to C-terminus: a single-chain variable fragment (scFv) comprising a variable heavy ($V_H$) domain linked to a variable light ($V_L$) domain; and a C-terminal cysteine.

Some embodiments provided herein relate to a humanized minibody that binds to CD8. The humanized minibody can include a polypeptide that comprises, from N-terminus to C-terminus: a single-chain variable fragment (scFv) comprising a variable heavy ($V_H$) domain linked to a variable light ($V_L$) domain; a hinge-extension domain comprising a human IgG1 or IgG2 hinge region; and a human IgG $C_H3$ sequence. In some embodiments, the hinge extension domain comprises a native IgG2 hinge sequence, for example a hinge sequence that comprises an IgG2 hinge sequence of SEQ ID NO: 55. In some embodiments, the hinge extension domain comprises an artificial IgG2 hinge sequence, for example a hinge-extension sequence that comprises a hinge-extension sequence of SEQ ID NO: 79.

Some embodiments provided herein relate to a nucleic acid encoding an antigen binding construct as described herein, for example a CD8 antibody or antibody fragment.

Some embodiments provided herein relate to a cell line that produces an antigen binding construct as described herein, for example a CD8 antibody or antibody fragment.

Some embodiments provided herein relate to a kit. The kit can include an antigen binding construct as described herein, for example a CD8 antigen binding fragment. In some embodiments, the kit includes a detectable marker.

Some embodiments provided herein relate to a method of detecting the presence or absence of CD8. The method can comprise applying an antigen binding construct as described herein, for example a CD8 antigen binding construct to a sample. The method can include detecting a binding or an absence of binding of the antigen binding construct to CD8. In some embodiments, the method is performed in vivo. In some embodiments, the method is performed in vitro. In some embodiments, part of the method is performed in vivo, and part of the method is performed in vitro.

Some embodiments provided herein relate to a method of targeting a therapeutic agent to a CD8. The method can include administering to a subject an antigen binding construct as described herein, for example a CD8 antibody or antibody fragment. In some embodiments, the antigen binding construct is conjugated to a therapeutic agent.

BRIEF DESCRIPTION OF THE DRAWINGS

FIG. 1C provides an example of a CD8 alpha.

FIG. 2A illustrates some embodiments of an alignment of the murine OKT8 Variable Heavy ($V_H$) region against a human antibody and a humanized $V_H$ region (the huOKT8 construct). Some embodiments of the CDR regions (Chothia) are indicated by the boxed region).

FIG. 2B illustrates some embodiments of an alignment of the murine OKT8 Variable Light ($V_L$) region against a humanized $V_L$ region and the huOKT8 construct. Some embodiments of the CDR regions (Chothia) are indicated by the boxed region).

FIG. 4 illustrates some embodiments of a chimeric OKT8 minibody $V_L$-$V_H$ sequence.

FIG. 5 illustrates some embodiments of a chimeric OKT8 minibody $V_H$-$V_L$ sequence.

FIG. 6 illustrates some embodiments of a humanized OKT8 minibody $V_L$-$V_H$ sequence.

FIG. 7 illustrates some embodiments of a humanized OKT8 minibody $V_H$-$V_L$ sequence.

FIG. 8 illustrates some embodiments of a humanized OKT8 cys-diabody $V_L$-5-$V_H$ sequence.

FIG. 9 illustrates some embodiments of a humanized OKT8 cys-diabody $V_H$-5-$V_L$ sequence.

FIG. 10 illustrates some embodiments of a humanized OKT8 cys-diabody $V_L$-8-$V_H$ sequence.

FIG. 11 illustrates some embodiments of a humanized OKT8 cys-diabody $V_H$-8-$V_L$ sequence.

FIG. 12A depicts some embodiments of sequences for cys-diabodies.

FIG. 12B depicts some embodiments of sequences for minibodies.

FIG. 12C depicts some embodiments of sequences for $V_L$.

FIG. 12D depicts some embodiments of sequences for hu$V_L$.

FIG. 12E depicts some embodiments of sequences for $V_H$.

FIG. 12F depicts some embodiments of sequences for hu$V_H$ (version "a" from Version 1).

FIG. 12G depicts some embodiments of sequences for hu$V_H$ (version "b" from Version 1).

FIG. 12H depicts some embodiments of sequences for hu$V_H$ (version "c" from Version 2).

FIG. 12I depicts some embodiments of sequences for hu$V_H$ (version "c" from Version 2).

FIGS. 18A and 18B are depictions of gels of western blots of the humanized OKT8 Minibodies.

FIGS. 22A and 22B are graphs displaying the flow cytometry analysis of the IAb_Mb_CD8 variants A and B.

FIGS. 23A and 23B are graphs displaying the flow cytometry analysis of the IAb_Mb_CD8 variants C and D.

FIGS. 26A and 26B display flow cytometry analysis of the IAb_Cys-Dba_CD8 variants.

FIG. 27 is a set of graphs depicting the flow cytometry analysis of the IAb_Cys-Dba_CD8 variants.

FIG. 29B is a graph depicting flow cytometry analysis of an IAb M1b CD8 and IAb M2b CD8 construct according to some embodiments herein.

FIG. 29E is a graph depicting flow cytometry analysis of an IAb_M1b CD8, IAb_M1bCD8 IgG2 EH, and IAb M1b CD8 IgG2 NH construct according to some embodiments herein.

FIG. 30C is a graph depicting flow cytometry analysis of an IAb_CysDb3b_CD8 and IAb_Cys-Db3b_CD8-Df construct according to some embodiments herein.

FIG. 31 is a series of PET images of mice labeled with $^{89}$Zr-Df-IAb_Cys-Db3b_CD8 constructs according to some embodiments herein.

DETAILED DESCRIPTION

Described herein are antigen binding constructs, including antibodies and fragments thereof, such as cys-diabodies and minibodies, that bind to a target molecule, CD8. Such antigen binding constructs can be useful for detecting the presence, localization, and/or quantities of the target molecule (CD8 and/or CD8+ cells, for example, certain classes of T-cells). Such antigen binding constructs can also be useful for targeting therapeutic agents to cells that express the target molecule. In some embodiments, methods are provided for detecting the presence or absence of the target molecule (or "target") using antigen binding constructs (including antibodies, and constructs such as cys-diabodies and/or minibodies). In some embodiments, methods are provided for using the antigen binding constructs for therapeutic purposes.

Definitions and Various Embodiments

"Treating" or "treatment" of a condition may refer to preventing the condition, slowing the onset and/or rate of development of the condition, reducing the risk of developing the condition, preventing and/or delaying the development of symptoms associated with the condition, reducing or ending symptoms associated with the condition, generating a complete or partial regression of the condition, or some combination thereof. The term "prevent" does not require the absolute prohibition of the disorder or disease.

A "therapeutically effective amount" or a "therapeutically effective dose" is an amount that produces a desired therapeutic effect in a subject, such as preventing, treating a target condition, delaying the onset of the disorder and/or symptoms, and/or alleviating symptoms associated with the condition. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and/or the route of administration. One skilled in the clinical and pharmacological arts will be able to determine a therapeutically effective amount through routine experimentation, for example by monitoring a subject's response to administration of a compound and adjusting the dosage accordingly, given the present disclosure. For additional guidance, see Remington: The Science and Practice of Pharmacy 21.sup.st Edition, Univ. of Sciences in Philadelphia (USIP), Lippincott Williams & Wilkins, Philadelphia, Pa., 2005.

Figure 1A:
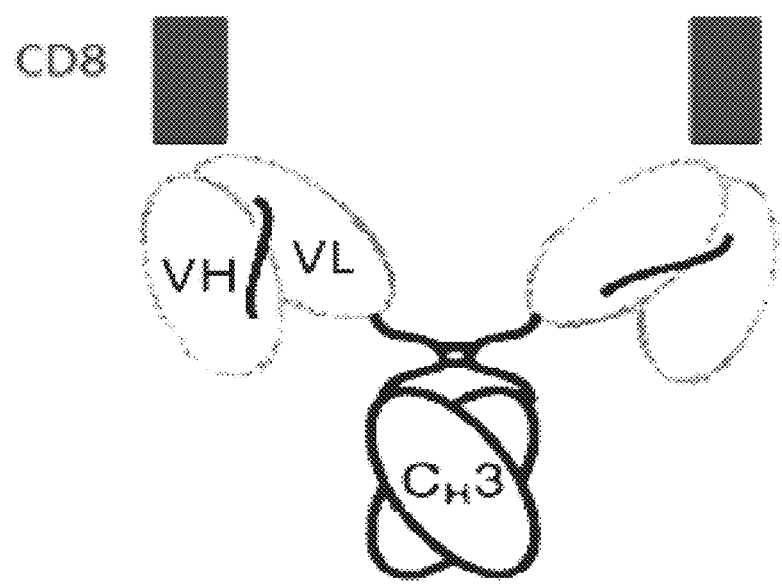
FIG. 1A illustrates some embodiments of a schematic of a minibody having bivalent binding to CD8.

The term "antigen binding construct" includes all varieties of antibodies, including binding fragments thereof. Further included are constructs that include 1, 2, 3, 4, 5, and/or 6 CDRs. In some embodiments, these CDRs can be distributed between their appropriate framework regions in a traditional antibody. In some embodiments, the CDRs can be contained within a heavy and/or light chain variable region. In some embodiments, the CDRs can be within a heavy chain and/or a light chain. In some embodiments, the CDRs can be within a single peptide chain. In some embodiments, the CDRs can be within two or more peptides that are covalently linked together. In some embodiments, they can be covalently linked together by a disulfide bond. In some embodiments, they can be linked via a linking molecule or moiety. In some embodiments, the antigen binding proteins are non-covalent, such as a diabody and a monovalent scFv. Unless otherwise denoted herein, the antigen binding constructs described herein bind to the noted target molecule. The term "target" or "target molecule" denotes the CD8 protein. Examples of CD8 proteins are known in the art, and include, for example the CD8 protein of SEQ ID NO: 24, FIG. 1C.

The term "antibody" includes, but is not limited to, genetically engineered or otherwise modified forms of immunoglobulins, such as intrabodies, chimeric antibodies, fully human antibodies, humanized antibodies, antibody fragments, and heteroconjugate antibodies (e.g., bispecific antibodies, diabodies, triabodies, tetrabodies, etc.). The term "antibody" includes cys-diabodies and minibodies. Thus, each and every embodiment provided herein in regard to "antibodies" is also envisioned as cys-diabody and/or minibody embodiments, unless explicitly denoted otherwise. The term "antibody" includes a polypeptide of the immunoglobulin family or a polypeptide comprising fragments of an immunoglobulin that is capable of noncovalently, reversibly, and in a specific manner binding a corresponding antigen. An exemplary antibody structural unit comprises a tetramer. In some embodiments, a full length antibody can be composed of two identical pairs of polypeptide chains, each pair having one "light" and one "heavy" chain (, connected through a disulfide bond. The recognized immunoglobulin genes include the kappa, lambda, alpha, gamma, delta, epsilon, and mu constant region genes, as well as the myriad immunoglobulin variable region genes. For full length chains, the light chains are classified as either kappa or lambda. For full length chains, the heavy chains are classified as gamma, mu, alpha, delta, or epsilon, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain ($V_L$) and variable heavy chain ($V_H$) refer to these regions of light and heavy chains respectively. As used in this application, an "antibody" encompasses all variations of antibody and fragments thereof. Thus, within the scope of this concept are full length antibodies, chimeric antibodies, humanized antibodies, single chain antibodies (scFv), Fab, Fab', and multimeric versions of these fragments (e.g., $F(ab')_2$) with the same binding specificity. In some embodiments, the antibody binds specifically to a desired target.

"Complementarity-determining domains" or "complementarity-determining regions ("CDRs") interchangeably refer to the hypervariable regions of $V_L$ and $V_H$. The CDRs are the target protein-binding site of the antibody chains that harbors specificity for such target protein. In some embodiments, there are three CDRs (CDR1-3, numbered sequentially from the N-terminus) in each $V_L$ and/or $V_H$, constituting about 15-20% of the variable domains. The CDRs are structurally complementary to the epitope of the target protein and are thus directly responsible for the binding specificity. The remaining stretches of the $V_L$ or $V_H$, the so-called framework regions (FRs), exhibit less variation in amino acid sequence (Kuby, Immunology, 4th ed., Chapter 4. W.H. Freeman & Co., New York, 2000).

The positions of the CDRs and framework regions can be determined using various well known definitions in the art, e.g., Kabat (Wu, T. T., E. A. Kabat. 1970. An analysis of the sequences of the variable regions of Bence Jones proteins and myeloma light chains and their implications for antibody complementarity. J. Exp. Med. 132: 211-250; Kabat, E. A., Wu, T. T., Perry, H., Gottesman, K., and Foeller, C. (1991) Sequences of Proteins of Immunological Interest, 5th ed., NIH Publication No. 91-3242, Bethesda, Md.), Chothia (Chothia and Lesk, J. Mol. Biol., 196:901-917 (1987); Chothia et al., Nature, 342:877-883 (1989); Chothia et al., J. Mol. Biol., 227:799-817 (1992); Al-Lazikani et al., J. Mol. Biol., 273:927-748 (1997)), ImMunoGeneTics database (IMGT) (on the worldwide web at imgt.org/) Giudicelli, V., Duroux, P., Ginestoux, C., Folch, G., Jabado-Michaloud, J., Chaume, D. and Lefranc, M.-P. IMGT/LIGM-DB, the IMGT® comprehensive database of immunoglobulin and T cell receptor nucleotide sequences Nucl. Acids Res., 34, D781-D784 (2006), PMID: 16381979; Lefranc, M.-P., Pommié, C., Ruiz, M., Giudicelli, V., Foulquier, E., Truong, L., Thouvenin-Contet, V. and Lefranc, G., IMGT unique numbering for immunoglobulin and T cell receptor variable domains and Ig superfamily V-like domains Dev. Comp. Immunol., 27, 55-77 (2003). PMID: 12477501; Brochet, X., Lefranc, M.-P. and Giudicelli, V. IMGT/V-QUEST: the highly customized and integrated system for IG and TR standardized V-J and V-D-J sequence analysis Nucl. Acids Res, 36, W503-508 (2008); AbM (Martin et al., Proc. Natl. Acad. Sci. USA, 86:9268-9272 (1989); the contact definition (MacCallum et al., J. Mol. Biol., 262:732-745 (1996)), and/or the automatic modeling and analysis tool Honegger A, Plückthun A. (world wide web at bioc dot uzh dot ch/antibody/Numbering/index dot html).

The term "binding specificity determinant" or "BSD" interchangeably refer to the minimum contiguous or non-contiguous amino acid sequence within a complementarity determining region necessary for determining the binding specificity of an antibody. A minimum binding specificity determinant can be within one or more CDR sequences. In some embodiments, the minimum binding specificity determinants reside within (i.e., are determined solely by) a portion or the full-length of the CDR3 sequences of the heavy and light chains of the antibody. In some embodiments, CDR3 of the heavy chain variable region is sufficient for the antigen binding construct specificity.

An "antibody variable light chain" or an "antibody variable heavy chain" as used herein refers to a polypeptide comprising the $V_L$ or $V_H$, respectively. The endogenous $V_L$ is encoded by the gene segments V (variable) and J (junctional), and the endogenous $V_H$ by V, D (diversity), and J. Each of $V_L$ or $V_H$ includes the CDRs as well as the framework regions. In this application, antibody variable light chains and/or antibody variable heavy chains may, from time to time, be collectively referred to as "antibody chains." These terms encompass antibody chains containing mutations that do not disrupt the basic structure of $V_L$ or $V_H$, as one skilled in the art will readily recognize. In some embodiments, full length heavy and/or light chains are contemplated. In some embodiments, only the variable region of the heavy and/or light chains are contemplated as being present.

Antibodies can exist as intact immunoglobulins or as a number of fragments produced by digestion with various peptidases. Thus, for example, pepsin digests an antibody below the disulfide linkages in the hinge region to produce $F(ab)'_2$, a dimer of Fab' which itself is a light chain ($V_L$—$C_L$) joined to $V_H$-$C_H$1 by a disulfide bond. The $F(ab)'_2$ may be reduced under mild conditions to break the disulfide linkage in the hinge region, thereby converting the $F(ab)'_2$ dimer into an Fab' monomer. The Fab' monomer is a Fab with part of the hinge region. (Paul, Fundamental Immunology 3d ed. (1993). While various antibody fragments are defined in terms of the digestion of an intact antibody, one of skill will appreciate that such fragments may be synthesized de novo either chemically or by using recombinant DNA methodology. Thus, the term "antibody," as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

For preparation of monoclonal or polyclonal antibodies, any technique known in the art can be used (see, e.g., Kohler & Milstein, Nature 256:495-497 (1975); Kozbor et al., Immunology Today 4:72 (1983); Cole et al., Monoclonal Antibodies and Cancer Therapy, pp. 77-96. Alan R. Liss, Inc. 1985; Advances in the production of human monoclonal antibodies Shixia Wang, Antibody Technology Journal 2011:1 1-4; J Cell Biochem. 2005 Oct. 1; 96(2):305-13; Recombinant polyclonal antibodies for cancer therapy; Sharon J, Liebman M A, Williams B R; and Drug Discov Today. 2006 Jul. 11(13-14):655-60, Recombinant polyclonal antibodies: the next generation of antibody therapeutics?, Haurum J S). Techniques for the production of single chain antibodies (U.S. Pat. No. 4,946,778) can be adapted to produce antibodies to polypeptides of this invention. Also, transgenic mice, or other organisms such as other mammals, may be used to express fully human monoclonal antibodies. Alternatively, phage display technology can be used to identify high affinity binders to selected antigens (see, e.g., McCafferty et al., supra; Marks et al., Biotechnology, 10:779-783, (1992)).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. In some embodiments, the terms "donor" and "acceptor" sequences can be employed. Humanization can be essentially performed following the method of Winter and co-workers (see, e.g., Jones et al., Nature 321:522-525 (1986); Riechmann et al., Nature 332:323-327 (1988); Verhoeyen et al., Science 239:1534-1536 (1988) and Presta, Curr. Op. Struct. Biol. 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some complementarity determining region ("CDR") residues and possibly some framework ("FR") residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, and drug; or (b) the variable region, or a portion thereof, is altered, replaced or exchanged with a variable region having a different or altered antigen specificity.

Antibodies further include one or more immunoglobulin chains that are chemically conjugated to, or expressed as, fusion proteins with other proteins. In some embodiments, the antigen binding constructs can be monovalent scFv constructs. In some embodiments, the antigen binding constructs can be bispecific constructs. A bispecific or bifunctional antibody is an artificial hybrid antibody having two different heavy/light chain pairs and two different binding sites. Other antigen-binding fragments or antibody portions of the invention include bivalent scFv (diabody), bispecific scFv antibodies where the antibody molecule recognizes two different epitopes, single binding domains (sdAb or nanobodies), and minibodies.

The term "antibody fragment" includes, but is not limited to one or more antigen binding fragments of antibodies alone or in combination with other molecules, including, but not limited to Fab', $F(ab')_2$, Fab, Fv, rIgG (reduced IgG), scFv fragments (monovalent, tri-valent, etc.), single domain fragments (nanobodies), peptibodies, minibodies, diabodies, and cys-diabodies. The term "scFv" refers to a single chain Fv ("fragment variable") antibody in which the variable domains of the heavy chain and of the light chain of a traditional two chain antibody have been joined to form one chain.

A pharmaceutically acceptable carrier may be a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier is "pharmaceutically acceptable" in that it is be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits. The pharmaceutical compositions described herein may be administered by any suitable route of administration. A route of administration may refer to any administration pathway known in the art, including but not limited to aerosol, enteral, nasal, ophthalmic, oral, parenteral, rectal, transdermal (e.g., topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. In some embodiments, the antigen binding construct can be delivered intraoperatively as a local administration during an intervention or resection.

The term "CD8 dependent disorder" includes cancers for which there is an immunological component (including response to cancer immunotherapies), autoimmune disorders inflammation disorders, and cancers, including but not limited to lung, ovarian, colorectal melanoma etc.

A minibody is an antibody format that has a smaller molecular weight than the full-length antibody while maintaining the bivalent binding property against an antigen. Because of its smaller size, the minibody has a faster clearance from the system and enhanced penetration when targeting tumor tissue. With the ability for strong targeting combined with rapid clearance, the minibody is advantageous for diagnostic imaging and delivery of cytotoxic/radioactive payloads for which prolonged circulation times may result in adverse patient dosing or dosimetry.

The phrase "specifically (or selectively) bind," when used in the context of describing the interaction between an antigen, e.g., a protein, to an antibody or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under designated immunoassay conditions, in some embodiments, the antibodies or binding agents with a particular binding specificity bind to a particular antigen at least two times the background and do not substantially bind in a significant amount to other antigens present in the sample. Specific binding to an antibody or binding agent under such conditions may require the antibody or agent to have been selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least than 10 to 100 times over the background.

The term "equilibrium dissociation constant ($K_D$, M)" refers to the dissociation rate constant ($k_d$, time$^{-1}$) divided by the association rate constant ($k_a$, time$^-$, M$^{-1}$). Equilibrium dissociation constants can be measured using any known method in the art. The antibodies of the present invention generally will have an equilibrium dissociation constant of less than about $10^{-7}$ or $10^{-8}$ M, for example, less than about $10^{-9}$ M or $10^{-10}$ M, in some embodiments, less than about $10^{-11}$ M, $10^{-12}$ M, or $10^{-13}$ M.

The term "isolated," when applied to a nucleic acid or protein, denotes that the nucleic acid or protein is essentially free of other cellular components with which it is associated in the natural state. In some embodiments, it can be in either a dry or aqueous solution. Purity and homogeneity can be determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. In some embodiments, this can denote that the nucleic acid or protein is at least 85% pure, more preferably at least 95% pure, and most preferably at least 99% pure of molecules that are present under in vivo conditions.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refer to compounds that have the same basic chemical structure as a naturally occurring amino acid, i.e., an .alpha.-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Percentage of sequence identity" can be determined by comparing two optimally aligned sequences over a comparison window, wherein the portion of the polynucleotide sequence in the comparison window may comprise additions or deletions (i.e., gaps) as compared to the reference sequence (e.g., a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (for example, 70%, 75%, 80%, 85%, 90%, 95%, 96%, 97%, 98% or 99% sequence identity over a specified region, or, when not specified, over the entire sequence of a reference sequence), when compared and aligned for maximum correspondence over a comparison window, or designated region as measured using one of the following sequence comparison algorithms or by manual alignment and visual inspection. Some embodiments provided herein provide polypeptides or polynucleotides that are substantially identical to the polypeptides or polynucleotides, respectively, exemplified herein (e.g., the variable regions exemplified in any one FIG. 2A, 2B, or 4-11, 12C-12I; the CDRs exemplified in any one of FIG. 2A, 2B, or 12C to 12I; the FRs exemplified in any one of FIG. 2A, 2B, or 12C-12I; and the nucleic acid sequences exemplified in any one of FIG. 12A-12I or 4-11). Optionally, the identity exists over a region that is at least about 15, 25 or 50 nucleotides in length, or more preferably over a region that is 100 to 500 or 1000 or more nucleotides in length, or over the full length of the reference sequence. With respect to amino acid sequences, identity or substantial identity can exist over a region that is at least 5, 10, 15 or 20 amino acids in length, optionally at least about 25, 30, 35, 40, 50, 75 or 100 amino acids in length, optionally at least about 150, 200 or 250 amino acids in length, or over the full length of the reference sequence. With respect to shorter amino acid sequences, e.g., amino acid sequences of 20 or fewer amino acids, in some embodiments, substantial identity exists when one or two amino acid residues are conservatively substituted, according to the conservative substitutions defined herein.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

Two examples of algorithms that are suitable for determining percent sequence identity and sequence similarity are the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, in some embodiments, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The terms "subject," "patient," and "individual" interchangeably refer to an entity that is being examined and/or treated. This can include, for example, a mammal, for example, a human or a non-human primate mammal. The mammal can also be a laboratory mammal, e.g., mouse, rat, rabbit, hamster. In some embodiments, the mammal can be an agricultural mammal (e.g., equine, ovine, bovine, porcine, camelid) or domestic mammal (e.g., canine, feline).

The term "therapeutically acceptable amount" or "therapeutically effective dose" interchangeably refer to an amount sufficient to effect the desired result. In some embodiments, a therapeutically acceptable amount does not induce or cause undesirable side effects. A therapeutically acceptable amount can be determined by first administering a low dose, and then incrementally increasing that dose until the desired effect is achieved.

The term "co-administer" refers to the administration of two active agents in the blood of an individual or in a sample to be tested. Active agents that are co-administered can be concurrently or sequentially delivered.

Antigen Binding Constructs (Including Antibodies and Binding Fragments)

Antigen binding constructs that bind to the target are described herein. An antigen binding construct is a molecule that includes one or more portions of an immunoglobulin or immunoglobulin-related molecule that specifically binds to, or is immunologically reactive with the target molecule.

In some embodiments, the antigen binding constructs allow for the detection of human CD8 which is a specific biomarker found on the surface of a subset of T-cells for diagnostic imaging of the immune system. Imaging of CD8 allows for the in vivo detection of T-cell localization. Changes in T-cell localization can reflect the progression of an immune response and can occur over time as a result various therapeutic treatments or even disease states.

In some embodiments, this is useful for imaging T-cell localization for immunotherapy. Adoptive immunotherapy is a form of therapy where a patient's own T-cells are manipulated in vitro and re-introduced into the patient. For this form of treatment, imaging of T-cells is useful for determining the status of the treatment.

In addition, CD8 plays a role in activating downstream signaling pathways that are important for the activation of cytolytic T cells that function to clear viral pathogens and provide immunity to tumors. CD8 positive T cells can recognize short peptides presented within the MHCI protein of antigen presenting cells. In some embodiments, engineered fragments directed to CD8 can potentiate signaling through the T cell receptor and enhance the ability of a subject to clear viral pathogens and respond to tumor antigens. Thus, in some embodiments, the antigen binding constructs provided herein can be agonists and can activate the CD8 target. In some embodiments, an agonist scFv, minibody, cys-diabody, and/or antibody is provided. In some embodiments, the agonist antigen binding construct includes one or more of the CDRs, heavy chain variable regions, or light chain variable regions provided herein. In some embodiments, the agonist can activate downstream signaling pathways through CD8 for the activation of cytolytic T cells that function to clear viral pathogens and provide immunity to tumors.

In some situations, using full-length antibodies for imaging is not optimal since they typically require imaging times to be scheduled more than 1 week after administration due to the long serum half-lives of full-length antibodies.

Another target-based approach for imaging subtypes of immune cells involves small molecules. For example, one approach for diagnostic imaging of the endogenous immune system has involved the use of small molecule tracers which detect changes in the cell's metabolic pathway such as $^{18}$F-fluoroacetate ([$^{18}$F]FAC). Since such tracers detect changes in the metabolic pathway, they target cell populations with elevated metabolic activities which primarily include activated T-cells. The limitation of this approach is that it will only detect the activated subset of T-cells, whereas imaging with anti-CD8 antibody fragments will detect the entire population of CD8 expressing T-cells as the target is expressed on both activated and resting CD8 cells.

Figure 1B:
FIG. 1B illustrates some embodiments of a schematic of a minibody.

The variable regions of the OKT8 antibody were reformatted by protein engineering into various alternative antigen binding constructs. The minibody format is a homodimer with each monomer having a single-chain variable fragment (scFv) linked to the human IgG1 $C_H3$ domain (see FIGS. 1A and 1B). In some embodiments, the scFv is composed of the variable heavy ($V_H$) and light ($V_L$) domains and is connected by an 18 amino acid GlySer-rich linker. In some embodiments, the scFv is tethered to the human IgG1 $C_H3$ domain by the human IgG1 upper and core hinge regions (15 residues) followed by a 10 amino acid GlySer linker. The minibody ($V_H$-$V_L$-$C_H3$) exists as a stable dimer due to the association between the $C_H3$ domains as well as the formation of disulfide bonds within the hinge regions. To allow for secretion of the minibody, a signal sequence is fused at the N-terminus of the variable heavy domain. In some embodiments, the GlySer residues allow for flexibility.

In some embodiments, glutamine and/or lysine residues can be added to enhance solubility.

Two variants of the chimeric OKT8 minibody were engineered that differed in the orientation of the variable regions ($V_H$ to $V_L$ and $V_L$ to $V_H$). Every antibody V domain contains two cysteines that form intra-disulfide bonds. The murine OKT8 $V_H$ has an extra cysteine in framework 3 (FR3) which may interfere with the expression of the protein as it may lead to aggregation and consequently retention in the endoplasmic reticulum (ER). The chimeric minibodies were made with a serine replacing the extra cysteine in the framework (C84S of the murine $V_H$). In some embodiments, any of the embodiments provided herein can be adjusted to include the C84S adjustment. Tables 0.1, 0.2, and 0.3 provide a summary of come embodiments of the arrangements of various antigen binding constructs provided herein.

TABLE 0.1

Minibodies

| 1 Name | 2 Leader | 3 Region 1 | 4 Linker | 5 Region 2 | 6 Remainder |
| --- | --- | --- | --- | --- | --- |
| Chimeric IAb_Mb1_CD8 SEQ ID NO: | Leader SEQ ID NO: 34 | murine $V_L$ SEQ ID NO: 40 | 18 aa linker SEQ ID NO: 36 | Murine $V_H$ SEQ ID NO: 44 | IgG1 hinge/linker-$C_H3$ domain SEQ ID NO: 38 |
| Chimeric IAb_Mb2_CD8 | Leader SEQ ID NO: 34 | murine $V_H$ SEQ ID NO: 44 | 18 aa linker SEQ ID NO: 36 | Murine $V_L$ SEQ ID NO: 40 | IgG1 hinge/linker-$C_H3$ domain SEQ ID NO: 38 |
| Humanized IAb_Mb1_CD8 | Leader SEQ ID NO: 34 | hu $V_L$ SEQ ID NO: 9 | 18 aa linker SEQ ID NO: 36 | hu$V_H$ ($2^{nd}$) SEQ ID NO: 6 | IgG1 hinge/linker-$C_H3$ domain SEQ ID NO: 38 |
| Humanized IAb_Mb2_CD8 | Leader SEQ ID NO: 34 | Hu $V_H$ ($2^{nd}$) SEQ ID NO: 6 | 18 aa linker SEQ ID NO: 36 | hu$V_L$ SEQ ID NO: 9 | IgG1 hinge/linker-$C_H3$ domain SEQ ID NO: 38 |

TABLE 0.2

Affinity Matured Minibodies

| 1 Name | 2 Leader | 3 Region 1 | 4 Linker | 5 Region 2 | 6 Remainder |
| --- | --- | --- | --- | --- | --- |
| IAb_Mb1a_CD8 | Leader SEQ ID NO: 34 | hu$V_L$ SEQ ID NO: 42 | 18aa Linker SEQ ID NO: 36 | hu$V_H$ (version a) SEQ ID NO: 46 | IgG1 hinge/linker-$C_H3$ domain SEQ ID NO: 38 |
| IAb_Mb2a_CD8 | Leader SEQ ID NO: 34 | hu$V_H$ (version a) SEQ ID NO: 46 | 18aa Linker SEQ ID NO: 36 | hu$V_L$ SEQ ID NO: 42 | IgG1 hinge/linker-$C_H3$ domain SEQ ID NO: 38 |
| IAb_Mb1b_CD8 | Leader SEQ ID NO: 34 | hu$V_L$ SEQ ID NO: 42 | 18aa Linker SEQ ID NO: 36 | hu$V_H$ (version b) SEQ ID NO: 48 | IgG1 hinge/linker-$C_H3$ domain SEQ ID NO: 38 |
| IAb_M1b_CD8 IgG2 NH | Leader SEQ ID NO: 34 | hu$V_L$ SEQ ID NO: 42 | 18aa Linker SEQ ID NO: 36 | hu$V_H$ (version b) SEQ ID NO: 48 | IgG2 native hinge SEQ ID NO: 55, IgG2 $C_H3$ domain, SEQ ID NO: 80 |
| IAb_M1b_CD8 IgG2 EH | Leader SEQ ID NO: 34 | hu$V_L$ SEQ ID NO: 42 | 18aa Linker SEQ ID NO: 36 | hu$V_H$ (version b) SEQ ID NO: 48 | IgG2 hinge-extension SEQ ID NO: 79, IgG2 $C_H3$ domain, SEQ ID NO: 80 |
| IAb_Mb2b_CD8 | Leader SEQ ID NO: 34 | hu$V_H$ (version b) | 18aa Linker | hu$V_L$ SEQ ID | IgG1 hinge/linker- |

TABLE 0.2-continued

Affinity Matured Minibodies

| 1<br>Name | 2<br>Leader | 3<br>Region 1 | 4<br>Linker | 5<br>Region 2 | 6<br>Remainder |
|---|---|---|---|---|---|
| | NO: 34 | SEQ ID<br>NO: 48 | SEQ ID<br>NO: 36 | NO: 42 | $C_H3$ domain<br>SEQ ID NO: 38 |
| IAb_Mb1c_CD8 | Leader<br>SEQ ID<br>NO: 34 | $huV_L$<br>SEQ ID<br>NO: 42 | 18aa<br>Linker<br>SEQ ID<br>NO: 36 | $huV_H$<br>(version c)<br>SEQ ID<br>NO: 50 | IgG1<br>hinge/linker-<br>$C_H3$ domain<br>SEQ ID NO: 38 |
| IAb_Mb2c_CD8 | Leader<br>SEQ ID<br>NO: 34 | $huV_H$<br>(version c)<br>SEQ ID<br>NO: 50 | 18aa<br>Linker<br>SEQ ID<br>NO: 36 | $huV_L$<br>SEQ ID<br>NO: 42 | IgG1<br>hinge/linker-<br>$C_H3$ domain<br>SEQ ID NO: 38 |
| IAb_Mb1d_CD8 | Leader<br>SEQ ID<br>NO: 34 | $huV_L$<br>SEQ ID<br>NO: 42 | 18aa<br>Linker<br>SEQ ID<br>NO: 36 | $huV_H$<br>(version d)<br>SEQ ID<br>NO: 52 | IgG1<br>hinge/linker-<br>$C_H3$ domain<br>SEQ ID NO: 38 |
| IAb_Mb2d_CD8 | Leader<br>SEQ ID<br>NO: 34 | $huV_H$<br>(version d)<br>SEQ ID<br>NO: 52 | 18aa<br>Linker<br>SEQ ID<br>NO: 36 | $huV_L$<br>SEQ ID<br>NO: 42 | IgG1<br>hinge/linker-<br>$C_H3$ domain<br>SEQ ID NO: 38 |

TABLE 0.3

Cys-Diabodies

| 1<br>Name | 2<br>Leader | 3<br>Region 1 | 4<br>Linker | 5<br>Region 2 | 6<br>Remainder |
|---|---|---|---|---|---|
| IAb_Cys-<br>Db1b_CD8 | Leader<br>SEQ ID NO: 26 | $huV_L$<br>SEQ ID NO: 42 | 5aa Linker<br>SEQ ID NO: 28 | $huV_H$<br>(version b)<br>SEQ ID NO: 48 | Cys Tail<br>SEQ ID NO: 32 |
| IAb_Cys-<br>Db2b_CD8 | Leader<br>SEQ ID NO: 26 | $huV_H$<br>(version b)<br>SEQ ID NO: 48 | 5aa Linker<br>SEQ ID NO: 28 | $huV_L$<br>SEQ ID NO: 42 | Cys Tail<br>SEQ ID NO: 32 |
| IAb_Cys-<br>Db3b_CD8 | Leader<br>SEQ ID NO: 26 | $huV_L$<br>SEQ ID NO: 42 | 8aa Linker<br>SEQ ID NO: 30 | $huV_H$<br>(version a)<br>SEQ ID NO: 48 | Cys Tail<br>SEQ ID NO: 32 |
| IAb_Cys-<br>Db4b_CD8 | Leader<br>SEQ ID NO: 26 | $huV_H$<br>(version a)<br>SEQ ID NO: 48 | 8aa Linker<br>SEQ ID NO: 30 | $huV_L$<br>SEQ ID NO: 42 | Cys Tail<br>SEQ ID NO: 32 |

Depicted in Tables 0.1, 0.2, and 03 are arrangements of sequences for monomers that can be used in minibodies (Table 0.1 and 0.2) and cys-diabodies (Table 0.3). Each row of the table represents the sequence of a monomer construct, with left-to-right representing N-terminus to C-terminus. In some embodiments, the shown sequences of each monomer construct are directly linked to each other. Thus, in some embodiments, the construct can include any of the constructs on a single row in Table 0.1, Table 0.2, or Table 0.3. In some embodiments, the constructs can include any combination in Table 0.1, Table 0.2, or Table 0.3. In some embodiments, for example, the first item in the first row, column 2 can be combined with the first row, column 3 to the first row column 4, to the first row column 5, to the first row, column 6. In some embodiments, column 3 and column 6 can be swapped with one another. In some embodiments, the first item in the first row, column 2 can be combined with the first row, column 3 to the second row column 4, to the second row column 5, to the second row, column 6. Thus, the tables represent all possible combinations, both within a single row and across various rows (and with columns swapped).

In some embodiments, an antigen binding construct includes a heavy chain CDR1 (HCDR1) of the HCDR1 in SEQ ID NOs: 3, 6, 44, 46, 48, 50, or 52; a heavy chain CDR2 (HCDR2) of the HCDR2 in SEQ ID NOs: 3, 6, 44, 46, 48, 50, or 52; a heavy chain CDR3 (HCDR3) of the HCDR3 in SEQ ID NOs: 3, 6, 44, 46, 48, 50, or 52; a light chain CDR1 (LCDR1) of the LCDR1 in SEQ ID NOs: 9 or 42; a light chain CDR2 (LCDR2) of the LCDR2 in SEQ ID NOs: 9 or 42; and/or a light chain CDR3 (LCDR3) of the LCDR3 in SEQ ID NOs: 9 or 42. In some embodiments, an antigen binding construct includes the HCDR1 of the HCDR1 in SEQ ID NO: 48, the HCDR2 of the HCDR2 in SEQ ID NO: 48, the HCDR3 of the HCDR3 in SEQ ID NO: 48, the LCDR1 of the LCDR1 in SEQ ID NO: 42, the LCDR2 of the LCDR2 in SEQ ID NO: 42, and the LCDR3 of the LCDR3 in SEQ ID NO: 42.

In some embodiments, the antigen binding construct includes 6, 5, 4, 3, 2, or 1, the above CDRs (some embodiments of the CDRs are indicated in FIGS. 2A, 2B, 12C-12I). In some embodiments, the antigen binding construct includes HCDR3. In some embodiments, the antigen binding construct binds specifically to the target molecule. In some embodiments, the antigen binding construct competes for binding with one or more of the antibodies having the herein provided CDRs. In some embodiments, the antigen binding construct includes at least the 3 heavy chain CDRs noted herein. In some embodiments, the antigen binding construct includes heavy chain CDR3. In some embodiments, the antigen binding construct further includes any one of the heavy chain CDR2 sequences provided herein.

In some embodiments, the antigen binding construct is human or humanized. In some embodiments, the antigen binding construct includes at least one human framework region, or a framework region with at least about 80% sequence identity, for example at least about 80%, 85%, 90%, 93%, 95%, 97%, or 99% identity to a human framework region. In some embodiments the antigen binding construct includes a heavy chain FR1 (HFR1) of the HFR1 in SEQ ID NO: 3, 6, 44, 46, 48, 50, or 52; a heavy chain FR2 (HFR2) of the HFR2 in SEQ ID NO: 3, 6, 44, 46, 48, 50, or 52; a heavy chain FR3 (HFR3) of the HFR3 in SEQ ID NO: 3, 6, 44, 46, 48, 50, or 52; a heavy chain FR4 (HFR4) of the HFR4 in SEQ ID NO: 3, 6, 44, 46, 48, 50, or 52; a light chain FR1 (LFR1) of the LFR1 in SEQ ID NO: 9 or 42; a light chain FR2 (LFR2) of the LFR2 in SEQ ID NO: 9 or 42; a light chain FR3 (LFR3) of the LFR3 in SEQ ID NO: 9 or 42; and a light chain FR4 (LFR4) of the LFR4 in SEQ ID NO: 9 or 42. In some embodiments the antigen binding construct includes a heavy chain FR1 (HFR1) of the HFR1 in SEQ ID NO: 48; a heavy chain FR2 (HFR2) of the HFR2 in SEQ ID NO: 48; a heavy chain FR3 (HFR3) of the HFR3 in SEQ ID NO: 48; a heavy chain FR4 (HFR4) of the HFR4 in SEQ ID NO: 48; a light chain FR1 (LFR1) of the LFR1 in SEQ ID NO: 42; a light chain FR2 (LFR2) of the LFR2 in SEQ ID NO: 42; a light chain FR3 (LFR3) of the LFR3 in SEQ ID NO: 42; and a light chain FR4 (LFR4) of the LFR4 in SEQ ID NO: 42. In some embodiments, the antigen binding construct includes 8, 7, 6, 5, 4, 3, 2, or 1 of the listed FRs.

In some embodiments, the antigen binding construct includes a detectable marker. In some embodiments, the antigen binding construct includes a therapeutic agent.

In some embodiments, the antigen binding construct is bivalent. Bivalent antigen binding construct can include at least a first antigen binding domain, for example a first scFv, and at least a second antigen binding domain, for example a second scFv. In some embodiments, a bivalent antigen binding construct is a multimer that includes at least two monomers, for example at least 2, 3, 4, 5, 6, 7, or 8 monomers, each of which has an antigen binding domain. In some embodiments, the antigen binding construct is a minibody. In some embodiments, the antigen binding construct is a diabody, including, for example, a cys-diabody. The scFv, and/or minibody and/or the cys-diabody can include any of the CDR and heavy chain variable region and/or light chain variable region embodiments provided herein (for example, the CDR sequences provided in FIGS. 2A, 2B, and 12C-12I). In some embodiments, the antigen binding construct is a monovalent scFv. In some embodiments, a monovalent scFv is provided that includes the HCDR1 in the HCDR1 of FIG. 2A, FIG. 12E-12I, or SEQ ID NO: 3, 6, 44, 46, 48, 50, or 52; the HCDR2 in the HCDR2 of FIG. 2A, FIG. 12E-12I, or SEQ ID NO: 3, 6, 44, 46, 48, 50, or 52; the HCDR3 in the HCDR3 of FIG. 2A, FIG. 12E-12I, or SEQ ID NO: 3, 6, 44, 46, 48, 50, or 52; the LCDR1 in the LCDR1 of FIG. 2B, FIG. 12C, FIG. 12D, SEQ ID NO: 9 or 42; the LCDR2 in the LCDR2 of FIG. 2B, FIG. 12C, FIG. 12D, SEQ ID NO: 9 or 42, and the LCDR3 in the LCDR3 of FIG. 2B, FIG. 12C, FIG. 12D, SEQ ID NO: 9 or 42. In some embodiments, a monovalent scFv is provided that includes the HCDR1 in the HCDR1 of SEQ ID NO: 48, the HCDR2 in the HCDR2 of SEQ ID NO: 48, the HCDR3 in the HCDR3 of SEQ ID NO: 48, the LCDR1 in the LCDR1 of SEQ ID NO: 42, the LCDR2 in the LCDR2 of SEQ ID NO: 42, and the LCDR3 in the LCDR3 of SEQ ID NO: 42. In some embodiments, the CDRs are defined in accordance with Chothia, as shown in FIG. 12D.

In some embodiments, the monovalent scFv includes the heavy chain variable region of the heavy chain variable region in FIG. 2A, FIGS. 4-11, FIG. 12C-12I, or SEQ ID NO: 3, 6, 44, 46, 48, 50, or 52. In some embodiments, the monovalent scFv includes the light chain variable region of the light chain variable region in FIG. 2B, 4-11, 12C, 12D, SEQ ID NO: 9, 42, or 40. In some embodiments, the monovalent scFv includes the heavy chain variable region of the heavy chain variable region in FIG. 2A, FIGS. 4-11, FIGS. 12C-12I, or SEQ ID NO: 3, 6, 44, 46, 48, 50, or 52 and the light chain variable region of the light chain variable region in in FIG. 2B, 4-11, 12C, 12D, SEQ ID NO: 9, 42, or 40. In some embodiments, the monovalent scFv includes the heavy chain variable region of the heavy chain variable region in SEQ ID NO: 48, and the light chain variable region of the light chain variable region in in SEQ ID NO: 42.

In some embodiments, the antigen binding construct is bispecific. Bispecific antibodies can include at least a first binding domain, for example an scFv that binds specifically to a first epitope, and at least a second binding domain, for example an scFv that binds specifically to a second epitope. Thus, bispecific antigen binding constructs can bind to two or more epitopes. In some embodiments, the first epitope and the second epitope are part of the same antigen, and the bispecific antigen binding construct can thus bind to two epitopes of the same antigen. In some embodiments, the first epitope is part of a first antigen, and the second epitope is part of a second antigen, and the bispecific antigen binding construct can thus bind to two different antigens. In some embodiments, the antigen binding construct binds to two epitopes simultaneously.

In some embodiments, the antigen binding construct has a heavy chain variable region of the heavy chain variable region in SEQ ID NO: 3, 6, 16, 18, 20, 22, 44, 46, 48, 50, or 52. In some embodiments, the antigen binding construct has a heavy chain variable region that includes a sequence with at least about 80% identity, for example at least about 80%, 85%, 86%, 87%, 88%, 89%, 90%, 91%, 92%, 93%, 94%, 95%, 96%, 97%, 98%, or 99% identity to SEQ ID NO: 3. In some embodiments, the antigen binding construct has a heavy chain variable region that includes a sequence with at least about 80% identity, for example at least about 80%, 85%, 86%, 87%, 88%, 89%, 90%, 91%, 92%, 93%, 94%, 95%, 96%, 97%, 98%, or 99% identity to SEQ ID NO: 6. In some embodiments, the antigen binding construct has a heavy chain variable region that includes a sequence with at least about 80% identity, for example at least about 80%, 85%, 86%, 87%, 88%, 89%, 90%, 91%, 92%, 93%, 94%, 95%, 96%, 97%, 98%, or 99% identity to SEQ ID NO: 44. In some embodiments, the antigen binding construct has a heavy chain variable region that includes a sequence with at least about 80% identity, for example at least about 80%, 85%, 86%, 87%, 88%, 89%, 90%, 91%, 92%, 93%, 94%, 95%, 96%, 97%, 98%, or 99% identity to SEQ ID NO: 46. In some embodiments, the antigen binding construct has a heavy chain variable region that includes a sequence with at least about 80% identity, for example at least about 80%, 85%, 86%, 87%, 88%, 89%, 90%, 91%, 92%, 93%, 94%, 95%, 96%, 97%, 98%, or 99% identity to SEQ ID NO: 48. In some embodiments, the antigen binding construct has a heavy chain variable region that includes a sequence with at least about 80% identity, for example at least about 80%, 85%, 86%, 87%, 88%, 89%, 90%, 91%, 92%, 93%, 94%, 95%, 96%, 97%, 98%, or 99% identity to SEQ ID NO: 50. In some embodiments, the antigen binding construct has a heavy chain variable region that includes a sequence with at least about 80% identity, for example at least about 80%, 85%, 86%, 87%, 88%, 89%, 90%, 91%, 92%, 93%, 94%, 95%, 96%, 97%, 98%, or 99% identity to SEQ ID NO: 52.

In some embodiments, the antigen binding construct has a light chain variable region that includes SEQ ID NO: 9, 16, 18, 20, 22, 40, or 42. In some embodiments, the antigen binding construct has a light chain variable region that includes a sequence with least about 80% identity, for example at least about 80%, 85%, 86%, 87%, 88%, 89%, 90%, 91%, 92%, 93%, 94%, 95%, 96%, 97%, 98%, or 99% identity to SEQ ID NO: 9. In some embodiments, the antigen binding construct has a light chain variable region that includes a sequence with least about 80% identity, for example at least about 80%, 85%, 86%, 87%, 88%, 89%, 90%, 91%, 92%, 93%, 94%, 95%, 96%, 97%, 98%, or 99% identity to SEQ ID NO: 40. In some embodiments, the antigen binding construct has a light chain variable region that includes a sequence with least about 80% identity, for example at least about 80%, 85%, 86%, 87%, 88%, 89%, 90%, 91%, 92%, 93%, 94%, 95%, 96%, 97%, 98%, or 99% identity to SEQ ID NO: 42. In some embodiments, the antigen binding construct is a human antigen binding construct and has a heavy chain variable region, a light chain variable region, or a heavy and light chain that is at least as identical as at least the heavy and/or light chain variable sequences noted above. In some embodiments, the antigen binding construct includes a heavy chain variable region that includes a sequence with least about 80% identity, for example at least about 80%, 85%, 86%, 87%, 88%, 89%, 90%, 91%, 92%, 93%, 94%, 95%, 96%, 97%, 98%, or 99% identity to SEQ ID NO: 48, and a light chain variable region that includes a sequence with least about 80% identity, for example at least about 80%, 85%, 86%, 87%, 88%, 89%, 90%, 91%, 92%, 93%, 94%, 95%, 96%, 97%, 98%, or 99% identity to SEQ ID NO: 42.

Some embodiments provided herein include an antigen binding construct that competes for binding to the target molecule with one or more antigen binding constructs provided herein. In some embodiments, the competing antigen binding construct binds to the same epitope on the target molecule as the reference antigen binding construct. In some embodiments, the reference antigen binding construct binds to a first epitope of the target molecule, and the competing antigen binding construct binds to a second epitope of the target molecule, but interferes with binding of the reference antigen binding construct to the target molecule, for example by sterically blocking binding of the reference antigen binding construct, or by inducing a conformational change in the target molecule. In some embodiments, the first epitope overlaps with the second epitope. In some embodiments, columns 3 and 5 of Tables 0.1 and/or 0.2 can be swapped. In some embodiments, any of the heavy chains variable regions provided herein can be combined with any of the light chain variable regions herein for a scFv, minibody, and/or diabody. In some embodiments, any of the heavy and/or light chain variable regions (columns 3 and 5) in tables 0.1, 0.2, and 0.3 can be exchanged with one another or another light or heavy chain variable region, to produce an antigen binding construct (such as a scFv, a cys-diabody, a minibody, or an antibody).

In some embodiments, the minibody and cys-diabody formats have advantageous pharmacokinetic characteristics for diagnostic imaging and certain therapeutic applications while maintaining the high binding affinity and specificity of a parental antibody. Compared to imaging with the full-length parental antibody, the pharmacokinetics are more desirable for these fragments in that they are able to target the antigen and then rapidly clear the system for rapid high-contrast imaging. In some embodiments, the shorter serum half lives for the minibody and the cys-diabody allow for imaging to occur over a range of times, approximately 8-48 hours post injection for the minibody and 2-24 hours post-injection for the cys-diabody. The rapid serum clearance together with better tissue penetration can allow for same day imaging, providing a significant advantage in the clinic with respect to patient care management.

In addition, the cys-diabody antibody format features the C-terminus cysteine tail. These two sulfhydryl groups (following mild reduction) provide a strategy for site-specific conjugation of functional moieties such as radiolabels that need not interfere with the cys-diabody's binding activity.

Diabodies that Bind to the Target Molecule

In some embodiments, the antigen binding construct can be a diabody. The diabody can include a first polypeptide chain which includes a heavy ($V_H$) chain variable domain connected to a light chain variable domain ($V_L$) on the first polypeptide chain. In some embodiments, the light and heavy variable chain domains can be connected by a linker. The linker can be of the appropriate length to reduce the likelihood of pairing between the two domains on the first polypeptide chain and a second polypeptide chain comprising a light chain variable domain ($V_L$) linked to a heavy chain variable domain $V_H$ on the second polypeptide chain connected by a linker that is too short to allow significant pairing between the two domains on the second polypeptide chain.

Figures 3A, 3B:
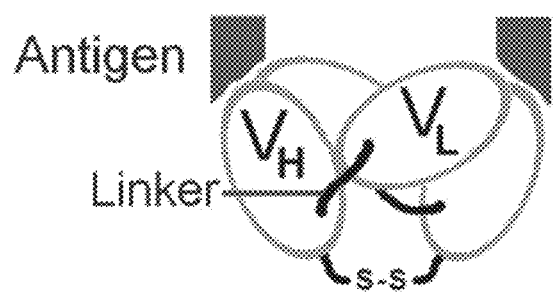
FIG. 3A illustrates some embodiments of a schematic of a cys-diabody showing bivalent binding to an antigen.
FIG. 3B illustrates a schematic of a cys-diabody showing bivalent binding to an antigen.

In some embodiments, the appropriate length of the linker encourages chain pairing between the complementary domains of the first and the second polypeptide chains and can promote the assembly of a dimeric molecule with two functional antigen binding sites. Thus, in some embodiments, the diabody is bivalent. In some embodiments, the diabody can be a cysteine linked diabody (a Cys-Db). A schematic of a Cys-Db binding to two antigen sites is illustrated in FIGS. 3A and 3B.

In some embodiments, the linker can be a peptide. In some embodiments, the linker can be any suitable length that promotes such assembly, for example, between 1 and 20 amino acids, such as 5 and 10 amino acids in length. As described further herein, some cys-diabodies can include a peptide linker that is 5 to 8 amino acids in length. In some embodiments, the linker need not be made from, or exclusively from amino acids, and can include, for example, modified amino acids (see, for example, Increased Resistance of Peptides to Serum Proteases by Modification of their Amino Groups, Rossella Galati, Alessandra Verdina, Giuliana Falasca, and Alberto Chersi, (2003) Z. Naturforsch, 58c, 558-561). In some embodiments, the linker can be 1, 2, 3, 4, 5, 6, 7, 8, 9, 10, 11, 12, 13, 14, 15, 16, 17, 18, 19, or 20 amino acids in length. In some embodiments, the linker can be from 2 to 30 angstroms in length, for example 2.5 to 27 angstroms.

In some embodiments, the antigen binding construct includes a humanized cys-diabody. The humanized cys-diabody can include a single-chain variable fragment (scFv) that includes a variable heavy ($V_H$) domain linked to a variable light ($V_L$) domain, and a C-terminal cysteine. In some embodiments, the humanized cys-diabody is a homodimer. In some embodiments, the humanized diabody is a heterodimer. In some embodiments, individual monomers are provided that each have a cysteine terminal residue.

In some embodiments, the scFv of the humanized cys-diabody has a $V_H$-$V_L$ orientation or a $V_L$-$V_H$ orientation. As used herein, a $V_H$-$V_L$ (which may also be referred to herein as "$V_H V_L$") orientation means that the variable heavy domain ($V_H$) of the scFv is upstream from the variable light domain ($V_L$) and a $V_LV_H$ orientation means that the $V_L$ domain of the scFv is upstream from the $V_H$ domain. As used herein, "upstream" means toward the N-terminus of an amino acid or toward the 5' end of a nucleotide sequence.

The antibody variable regions can be linked together by a linker as described herein. In some embodiments, the linker is a GlySer linker as described herein.

In some embodiments, the cys-diabody includes a detectable marker.

In some embodiments, the cys-diabody includes a pair of monomers. Each monomer can include a polypeptide. In some embodiments, the polypeptides of the monomers are identical (for example, cys-diabody can be a homodimer). In some embodiments, the polypeptides of the monomers are different (for example, the cys-diabody can be a heterodimer).

In some embodiments, the polypeptide of the monomer includes SEQ ID NO: 12 (See FIG. 8). In some embodiments, the polypeptide of the monomer includes a sequence with least about 80% identity, for example at least about 80%, 85%, 86%, 87%, 88%, 89%, 90%, 91%, 92%, 93%, 94%, 95%, 96%, 97%, 98%, or 99% identity to SEQ ID NO: 12 (cys-diabody ($V_L$-5-$V_H$)).

In some embodiments, the polypeptide of the monomer includes SEQ ID NO: 13 (See FIG. 9). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, or 99% identity to SEQ ID NO: 13 (cys-diabody ($V_H$-5-$V_L$)).

In some embodiments, the polypeptide of the monomer includes SEQ ID NO: 14 ($V_L$-8-$V_H$)] (See FIG. 10). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 14.

In some embodiments, the polypeptide of the monomer includes SEQ ID NO: 15 (humanized OKT8 cys-diabody ($V_H$-8-$V_L$)) (See FIG. 11). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 15.

In some embodiments, the polypeptide of the monomer includes any of the combined sections as indicated in Table 0.3, including polypeptides of the monomer with a sequences of at least about 80% identity, for example at least about 80%, 85%, 86%, 87%, 88%, 89%, 90%, 91%, 92%, 93, 94, 95%, 96%, 97%, 98%, 99%, or 100% identity to the monomers as set forth in Table 0.3.

In some embodiments, the cysteines are cross-linked with one another. In some embodiments, the cysteines are reduced, and thus, these tail forming cysteines do not form a disulfide bond with one another. In some embodiments, one or more of the "tail forming" cysteines form a covalent bond with one or more detectable marker, such as a fluorescent probe.

As will be appreciated by those of skill in the art, while the present disclosure generally references "cys-diabodies" alternative arrangements can be employed to achieve the same or similar ends. In some embodiments, any covalently modifiable moiety can be employed in place of one or more of the cysteines. For example, this can include a GlySer linker, a GlyLeu linker, and/or an insert cysteine after a short tag. In some embodiments, the connection can be established via a coiled coil or a leucine zipper. In some embodiments, the "tail" itself can include functional groups on its end so that it can selectively bind to a desired residue and/or location at the ends of each of the polypetides, in place of the disulfide bond itself. In some embodiments, rather than the tail providing space between the two polypeptide chains, the covalently modifiable moieties can be attached directly to the end of the heavy or light chain polypeptide, but the two covalently modifiable moieties can be connected by a linker.

In some embodiments, a chimeric cys-diabody that binds to the target molecule is provided. In some embodiments, the chimeric cys-diabody includes a monomer in the $V_L$-$V_H$ format, and includes the sequence of SEQ ID NO: 12 or 14, or a sequence having at least about 80% identity thereto, for example at least about 80%, 85%, 90%, 95%, 96%, 97%, 98%, or 99%% identity thereto. In some embodiments, the chimeric cys-diabody includes a monomer in the $V_H$-$V_L$ format, and includes the sequence of SEQ ID NO: 13 or 15, or a sequence having at least about 80% identity thereto, for example at least about 80%, 85%, 90%, 95%, 96%, 97%, 98%, or 99%% identity thereto.

In some embodiments, any of the constructs provided herein (including those arrangements noted as cys-diabody embodiments, can be provided as a scFv embodiment. In such embodiments, the construct can still include the cysteine on the tail, but simply not be cross-linked. In other embodiments, the construct need not have the cysteine in a tail or the tail at all.

Linker and/or Tail Options

In some embodiments, for individual antibodies, the heavy and light chain variable domains can associate in different ways. For this reason, the use of different linker lengths allows for conformational flexibility and range-of-motion to ensure formation of the disulfide bonds.

In some embodiments, the two linker lengths can be somewhere between (and including) about 1 to 50 amino acids, for example, 2 to 15, 2 to 14, 3 to 13, 4 to 10, or 5 amino acids to 8 amino acids. In some embodiments, each linker within a pair for a diabody can be the same length. In some embodiments, each linker within the pair can be a different length. In some embodiments, any combination of linker length pairs can be used, as long as they allow and/or promote the desired combinations. In some embodiments, a modified amino acid can be used.

FIGS. 8-11 provide four Cys-Db variants, $V_H$-5-$V_L$, $V_H$-8-$V_L$, $V_L$-5-$V_H$, and VL8VH (see FIGS. 8-11, and Table 0.3). Producing and testing the expression and binding of all four variants allows for identification of a desired format for protein production for each new Cys-Db. Evaluating the set of variants can help to make certain that a high-quality, stable protein is produced where the disulfide bridge is available. Therefore, engineering a Cys-Db can involve using two distinct linker lengths, not one—as in the minibody, as well as both orientations of the variable regions, $V_H$-$V_L$ and $V_L$-$V_H$.

In some embodiments, the linker is a GlySer linker. The GlySer linker can be a polypeptide that is rich in Gly and/or Ser residues. In some embodiments, at least about 40% of the amino acid residues of the GlySer linker are Gly, Ser, or a combination of Gly and Ser, for example at least about 40%, 50%, 60%, 70%, 80%, or 90%. In some embodiments, the GlySer linker is at least about 2 amino acids long, for example at least about 3, 4, 5, 6, 7, 8, 9, 10, 11, 12, 13, 14, 15, 16, 17, 18, 19, 20, 25, 30, 35, or 40 amino acids long. In some embodiments, the linker includes at least one of SEQ ID NO: 28, 30, and/or 36.

In some embodiments, a cysteine is added at the C-terminus of the diabody. This cysteine can allow the diabody complex to form covalent cysteine bonds and provides the option for available sulfur residues for site-specific conjugation of functional moieties such as radiolabels. In some embodiments, a terminal end of the antibody itself is altered so as to contain a cysteine. In some embodiments, a tail sequence, for example (Gly-Gly-Cys) is added at the C-terminus. In some embodiments, the cysteine tail sequence allows two monomers of a cys-diabody to form disulfide bonds with each other. In some embodiments, the cysteine tail sequence allows a cys-diabody to form disulfide linkages with a detectable moiety such as a detectable marker and/or therapeutic agent. The sulfhydryl groups of the cysteine tail can undergo mild reduction prior to site-specific conjugation of a desired functional moiety, for example a detectable marker and/or therapeutic agent. In some embodiments, the tail is at least about 1 amino acid long, for example at least about 1, 2, 3, 4, 5, 6, 7, 8, 9, 10, 11, 12, 13, 14, 15, 16, 17, 18, 19, 20, 25, 30, 35, or 40 amino acids long. In some embodiments, the tail includes at least one of SEQ ID NO: 32. In some embodiments, the tail is 3 to 8 amino acids in length. In some embodiments, the tail can and/or include a coiled coil and/or a leucine zipper. As noted above, in some embodiments, the cysteine is located at the c-terminus; however, this does not require that the cysteine be located as the last c-terminal amino acid. Instead, this denotes that the cysteine can be part of any of the residues that are located in the C-terminus of the protein.

In some embodiments, the linking option between the two C-terminuses can be achieved by a cysteine, for direct and/or indirect, cross-linking.

Minibodies that Bind to the Target Molecule

A "minibody" as described herein includes a homodimer, wherein each monomer is a single-chain variable fragment (scFv) linked to a human IgG1 $C_H3$ domain by a linker, such as a hinge sequence. In some embodiments, the hinge sequence is a human IgG1 or IgG2 hinge sequence as shown in FIG. 12B, SEQ ID NOs: 53-60. In some embodiments, the CH3 sequence comprises an IgG1 $C_H3$, or IgG2 $C_H3$ sequence as shown in FIG. 12B, SEQ ID NOs: 37-38 and 80-81.

In some embodiments, the hinge sequence is an artificial hinge sequence. In some embodiments, the hinge sequence can be an IgG hinge from any one or more of the four classes. The artificial hinge sequence may include a portion of a human IgG1 or IgG2 hinge and a GlySer linker (also known as an "extension" when distinguishing this section from the generic linker sequence that links the Vh and Vl regions) sequence.

In some embodiments, the artificial hinge sequence includes approximately the first 14 or 15 residues of the human IgG1 hinge followed by an extension sequence. In some embodiments, the extension can be any of those provided herein. In some embodiments, the extension can be a GlySer extension sequence that is 6, 7, 8, 9 or 10 amino acids in length. In some embodiments, the artificial hinge sequence includes approximately the first 15 residues of the IgG1 hinge followed by a GlySer extension sequence that is about 10 amino acids in length. In some embodiments, association between the $C_H3$ domains causes the minibody to exist as a stable dimer.

In some embodiments, the hinge sequence comprises a human IgG2 hinge sequence. In some embodiments, the hinge sequence comprises an IgG2 hinge sequence. In some embodiments, the hinge sequence comprises a native hIgG2IgG2 sequence ("NH"). An exemplary native hinge sequence that can be used in conjunction with embodiments herein is shown in FIG. 12B, SEQ ID NO: 55. In some embodiments, any and all of the constructs provided herein can be used with an hIgG2 hinge region.

In some embodiments, the hinge sequence comprises a native human IgG2 sequence of SEQ ID NO: 55. In some embodiments, the hinge sequence comprises an artificial IgG2 hinge sequence. In some embodiments the native IgG2 sequence comprises an artificial hinge-extension (EH) sequence. In some embodiments, the artificial hinge-extensions sequence comprises SEQ ID NO: 79. In some embodiments, the artificial hinge sequence includes approximately the first 12 to 15 residues, for example 12 residues of the human IgG2 hinge sequence followed by a GlySer extension sequence that is 6, 7, 8, 9, 10, 11, or 12 amino acids in length. An exemplary artificial hinge sequences that can be used in conjunction with embodiments herein is shown in FIG. 12B, SEQ ID NO: 79. In some embodiments, any of the above noted hinge region options (e.g., Tables 0.1 or 0.2) can be employed in a minibody. In some embodiments, any of the hinge regions noted in Tables 0.1 or 0.2 can be replaced with an IgG2 hinge region. In some embodiments, any of the constructs in tables 0.1 or 0.2, and/or any of the constructs depicted in the figures can have the depicted hinge region replaced with part or all of a hinge region from hIgG2 or IgG2.

In some embodiments, the minibody scFv sequence can include CDR and/or FR, and or variable region sequences that are similar and/or the same to a diabody sequence described herein (for Example, as found in FIGS. 2A, 2B, 4, 5, 6, 7, 8, 9, 10, 11, and 12C-12I and tables 0.1 and 0.2). In some embodiments, the minibody scFv has a sequence (CDR, CDRs, full set of 6 CDRS, heavy chain variable region, light chain variable region, heavy and light chain variable regions, etc.) that is at identical to a scFv of a cys-diabody described herein.

In some embodiments, the minibody has a sequence that is at least about 80% identical to a sequence in SEQ ID NO: 3, 6, 9, 16, 18, 20, 22, 34, 36, 38, 53-60, 40, 42, 44, 46, 48, 50, and 52, and/or the sequence for the arrangements in Tables 0.1 and/or 0.2, for example at least about 80%, 85%, 86%, 87%, 88%, 89%, 90%, 91%, 92%, 93, 94, 95%, 96%, 97%, 98%, or 99% identity.

In some embodiments, the minibody has a variable chain region that is at least about 80% identical to a sequence in SEQ ID NO: 3, 6, 9, 16, 18, 20, 22, 40, 42, 44, 46, 48, 50, and 52, for example at least about 80%, 85%, 86%, 87%, 88%, 89%, 90%, 91%, 92%, 93, 94, 95%, 96%, 97%, 98%, or 99% identity.

The scFv can have a $V_H$-$V_L$ or a $V_L$-$V_H$ orientation. In some embodiments, the $V_H$ and $V_L$ are linked to each other by an amino acid linker sequence. The amino acid linker can be a linker as described herein. In some embodiments, the linker is GlySer-rich and approximately 15-20 amino acids in length. In another embodiment, the linker is GlySer rich and is 18 amino acids in length. In some embodiments, the linker length varies between (and including) about 1 to 50 amino acids, for example, 2 to 30, 3 to 20, 4 to 15, or 5 amino acids to 8 amino acids. In some embodiments, the minibody scFv has a sequence that is at least about 80% identical to a scFv of a cys-diabody described herein, for example at least about 80%, 85%, 86%, 87%, 88%, 89%, 90%, 91%, 92%, 93, 94, 95%, 96%, 97%, 98%, or 99% identity. The scFv can have a $V_H$V$_L$ or a $V_L$V$_H$ orientation.

In some embodiments, each monomer of the minibody includes the following elements, from N-terminus to C-terminus: (a) an scFv sequence that includes a $V_H$ domain linked to a $V_L$ domain and that binds to the target molecule, (b) a hinge-extension domain comprising a human IgG1 hinge region, and (c) a human IgG $C_H3$ sequence. In some embodiments, each monomer of the minibody includes the following elements, from N-terminus to C-terminus: (a) an scFv sequence that includes a $V_H$ domain linked to a $V_L$ domain and that binds to the target molecule, (b) a hinge-extension domain comprising an IgG2 hinge region as described herein, and (c) a human IgG $C_H3$ sequence. In some embodiments, each monomer of the minibody includes an IgG2, an IgG3, or an IgG4 $C_H3$. In some embodiments, each monomer of the minibody can include a CH3 domain of an IgA or IgD and/or a CH4 domain of a IgM and/or an IgE. In some embodiments, the minibody is encoded by a nucleic acid can be expressed by a cell, a cell line or other suitable expression system as described herein. Thus, a signal sequence can be fused to the N-terminus of the scFv to enable secretion of the minibody when expressed in the cell or cell line.

Figure 2A:
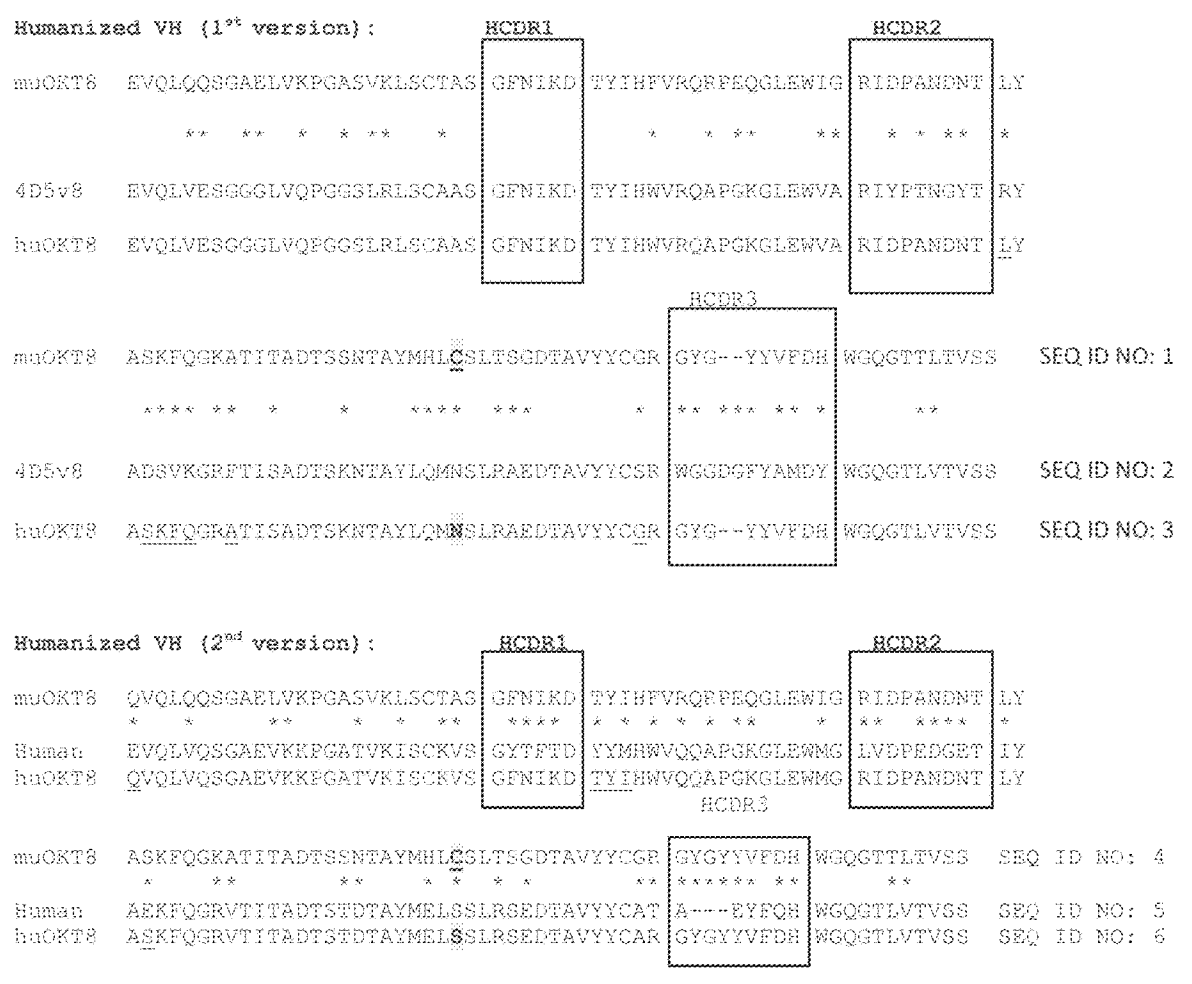

In some embodiments, the scFv, minibody, cys-diabody and/or antibody includes one or more of the residues in the humanized sequence shown in FIGS. 2A and/or 2B and denoted with an asterisk. In some embodiments, while one or more of the residues marked with an asterisk in FIG. 2A or 2B is present; the remaining sequence can be varied. For example, the sequence can be 80, 81, 82, 83, 84, 85, 86, 87, 88, 89, 90, 91, 92, 93, 94, 95, 96, 97, 98, 99 percent or greater identity to the remaining sections of the sequence. In some embodiments, the human and/or humanized antigen binding construct will include one or more of the asterisked residues in FIG. 2A, for example 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, or 47. In some embodiments, the antigen binding construct includes one or more of the underlined residues in FIG. 2A. In some embodiments, the antigen binding construct includes one or more of the non-underlined residues in FIG. 2A. In some embodiments, the antigen binding construct includes one or more of the non-underlined residues in FIG. 2A as well as the boxed CDR sections, whereas other residues are allowed to vary. In some embodiments, the antigen binding construct Alternatively, and/or in addition to, the antigen binding construct can include one or more of the asterisked residues in FIG. 2A or 2B, for example 1, 2, 3, 4, 5, 6, 7, 8, 9, 10, 11, 12, 13, 14, 15, 16, 17, 18, 19, or 20. In some embodiments, the antigen binding construct includes one or more of the non-underlined residues in FIG. 2A or 2B. In some embodiments, the antigen binding construct includes one or more of the non-underlined residues in FIG. 2A or 2B as well as the boxed CDR sections, whereas other residues are allowed to vary. In some embodiments, the CDR residues are maintained and the residues with the asterisk are maintained, but one or more of the other residues are allowed to vary.

In some embodiments, a chimeric minibody that binds to the target molecule is provided. In some embodiments, the chimeric minibody includes a monomer in the $V_L$-$V_H$ format, and includes the sequence of SEQ ID NO: 16 or 20, or a sequence having at least about 80% identity thereto, for example at least about 80%, 85%, 90%, 95%, 96%, 97%, 98%, or 99%% identity thereto. In some embodiments, the chimeric minibody includes a monomer in the $V_H$-$V_L$ format, and includes the sequence of SEQ ID NO: 18 or 22, or a sequence having at least about 80% identity thereto, for example at least about 80%, 85%, 90%, 95%, 96%, 97%, 98%, or 99%% identity thereto.

In some embodiments, the polypeptide of the monomer includes any of the combined sections as indicated in Tables 0.1 and 0.2, including polypeptides of the monomer with a sequences of at least about 80% identity, for example at least about 80%, 85%, 86%, 87%, 88%, 89%, 90%, 91%, 92%, 93, 94, 95%, 96%, 97%, 98%, 99%, or 100% identity to the monomers as set forth in Tables 0.1 and 0.2.

Nucleic Acids

In some embodiments, the polypeptides of the antigen binding constructs can be encoded by nucleic acids and expressed in vivo or in vitro, or these peptide can be synthesized chemically. Thus, in some embodiments, a nucleic acid encoding an antigen binding construct is provided. In some embodiments, the nucleic acid encodes one part or monomer of a cys-diabody or minibody. In some embodiments, the nucleic acid encodes two or more monomers, for example, at least 2 monomers. Nucleic acids encoding multiple monomers can include nucleic acid cleavage sites between at least two monomers, can encode transcription or translation start site between two or more monomers, and/or can encode proteolytic target sites between two or more monomers.

Figure 13:
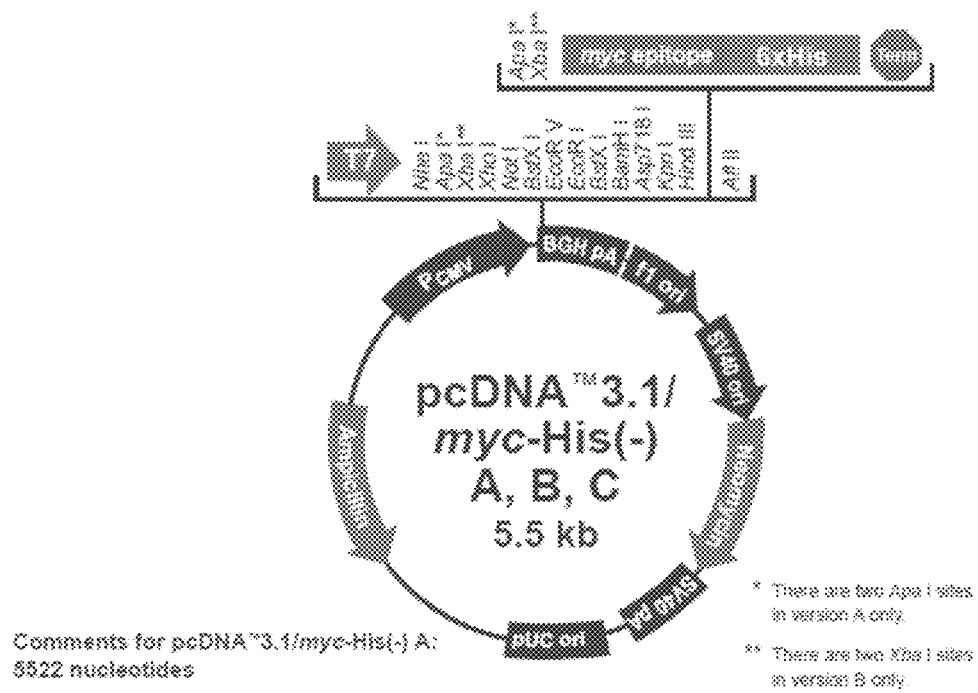
FIG. 13 illustrates some embodiments of a vector map for pcDNA™ 3.1/myc-His(−) Versions A, B, C.

In some embodiments, an expression vector contains a nucleic acid encoding an antigen binding construct as disclosed herein. In some embodiments, the expression vector includes pcDNA3.1™/myc-His (−) Version A vector for mammalian expression (Invitrogen, Inc.), or a variant thereof (see FIG. 13). The pcDNA3.1 expression vector features a CMV promoter for mammalian expression and both mammalian (Neomycin) and bacterial (Ampicillin) selection markers (see FIG. 10). In some embodiments, the expression vector includes a plasmid. In some embodiments, the vector includes a viral vector, for example a retroviral or adenoviral vector. In embodiments, the vector includes a cosmid, YAC, or BAC.

In some embodiments, the nucleotide sequence encoding at least one of the minibody monomers comprises at least one of SEQ ID NOs: 17, 19, 21, 23, 39, 41, 43, 45, 47, 49, 51, or a sequence having at least about 80% identity, for example about 80%, 85%, 86%, 87%, 88%, 89%, 90%, 91%, 92%, 93, 94, 95%, 96%, 97%, 98%, 99%, or greater identity thereto.

In some embodiments, the nucleotide sequence encoding at least one of the cys-diabody monomers includes SEQ ID NOs: 77, 78, 10, 11, 39, 41, 43, 45, 47, 49, 51, or a sequence having at least about 80% identity, for example about 80%, 85%, 86%, 87%, 88%, 89%, 90%, 91%, 92%, 93, 94, 95%, 96%, 97%, 98%, 99% or greater identity thereto.

Cell Lines

In some embodiments, a cell line is provided that expresses at least one of the antigen binding constructs described herein. In some embodiments, a mammalian cell line (e.g., CHO-K1 cell line) is an expression system to produce the minibodies, cys-diabodies or other antibodies as described herein. In some embodiments, the minibodies, cys-diabodies and other antibodies or antibody fragments described herein are non-glycosylated, and a mammalian expression system is not required, as such post-translational modifications are not needed. Thus, in some embodiments, one or more of a wide variety of mammalian or non-mammalian expression systems are used to produce the antigen binding constructs disclosed herein (for example, anti-CD8 minibodies and cys-diabodies) including, but not limited to mammalian expression systems (e.g., CHO-K1 cells), bacterial expression systems (e.g., E. *Coli*, *B. subtilis*) yeast expression systems (e.g., *Pichia*, *S. cerevisiae*) or any other known expression system. Other systems can include insect cells and/or plant cells.

Antigen Binding Construct Modifications

In some embodiments, the antigen binding construct includes at least one modification. Exemplary modifications include, but are not limited to, antigen binding constructs that have been modified by glycosylation, acetylation, pegylation, phosphorylation, amidation, derivatization by known protecting/blocking groups, proteolytic cleavage, and linkage to a cellular ligand or other protein. Any of numerous chemical modifications may be carried out by known techniques, including, but not limited to, specific chemical cleavage, acetylation, formylation and metabolic synthesis of tunicamycin. In some embodiments, the derivative can contain one or more non-natural amino acids.

In some embodiments, the antigen binding construct is conjugated to another substance to form an anti-target conjugate. The conjugates described herein can be prepared by known methods of linking antigen binding constructs with lipids, carbohydrates, protein or other atoms and molecules. In some embodiments, the conjugate is formed by site-specific conjugation using a suitable linkage or bond. Site-specific conjugation is more likely to preserve the binding activity of an antigen binding construct. The substance may be conjugated or attached at the hinge region of a reduced antigen binding construct via disulfide bond formation. For example, introduction of cysteine residues at the C-terminus of a scFv fragment, such as those that can be introduced in the cys-diabodies described herein, allows site-specific thiol-reactive coupling at a site away from the antigen binding site to a wide variety of agents. Other linkages or bonds used to form the conjugate can include, but are not limited to, a covalent bond, a non-covalent bond, a sulfide linkage, a hydrazone linkage, a hydrazine linkage, an ester linkage, an amido linkage, and amino linkage, an imino linkage, a thiosemicabazone linkage, a emicarbazone linkage, an oxime linkage and a carbon-carbon linkage.

Detectable Markers

In some embodiments, a modified antigen binding construct is conjugated to a detectable marker. As used herein, a "detectable marker" includes an atom, molecule, or compound that is useful in diagnosing, detecting or visualizing a location and/or quantity of a target molecule, cell, tissue, organ and the like. Detectable markers that can be used in accordance with the embodiments herein include, but are not limited to, radioactive substances (e.g., radioisotopes, radionuclides, radiolabels or radiotracers), dyes, contrast agents, fluorescent compounds or molecules, bioluminescent compounds or molecules, enzymes and enhancing agents (e.g., paramagnetic ions). In addition, some nanoparticles, for example quantum dots and metal nanoparticles (described below) can be suitable for use as a detection agent. In some embodiments, the detectable marker is IndoCyanine Green (ICG).

Exemplary radioactive substances that can be used as detectable markers in accordance with the embodiments herein include, but are not limited to, $^{18}$F, $^{18}$F-FAC, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{75}$Se, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac. Exemplary Paramagnetic ions substances that can be used as detectable markers include, but are not limited to ions of transition and lanthanide metals (e.g. metals having atomic numbers of 6 to 9, 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

When the detectable marker is a radioactive metal or paramagnetic ion, in some embodiments, the marker can be reacted with a reagent having a long tail with one or more chelating groups attached to the long tail for binding these ions. The long tail can be a polymer such as a polylysine, polysaccharide, or other derivatized or derivatizable chain having pendant groups to which may be bound to a chelating group for binding the ions. Examples of chelating groups that may be used according to the embodiments herein include, but are not limited to, ethylenediaminetetraacetic acid (EDTA), diethylenetriaminepentaacetic acid (DTPA), DOTA, NOTA, NOGADA, NETA, deferoxamine (DfO), porphyrins, polyamines, crown ethers, bis-thiosemicarbazones, polyoximes, and like groups. The chelate can be linked to the antigen binding construct by a group which allows formation of a bond to the molecule with minimal loss of immunoreactivity and minimal aggregation and/or internal cross-linking. The same chelates, when complexed with non-radioactive metals, such as manganese, iron and gadolinium are useful for MRI, when used along with the antigen binding constructs and carriers described herein. Macrocyclic chelates such as NOTA, NOGADA, DOTA, and TETA are of use with a variety of metals and radiometals including, but not limited to, radionuclides of gallium, yttrium and copper, respectively. Other ring-type chelates such as macrocyclic polyethers, which are of interest for stably binding radionuclides, such as Radium-223 for RAIT may be used. In certain embodiments, chelating moieties may be used to attach a PET imaging agent, such as an Aluminum-$^{18}$F complex, to a targeting molecule for use in PET analysis.

Exemplary contrast agents that can be used as detectable markers in accordance with the embodiments of the disclosure include, but are not limited to, barium, diatrizoate, ethiodized oil, gallium citrate, iocarmic acid, iocetamic acid, iodamide, iodipamide, iodoxamic acid, iogulamide, iohexyl, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, thallous chloride, or combinations thereof.

Bioluminescent and fluorescent compounds or molecules and dyes that can be used as detectable markers in accordance with the embodiments of the disclosure include, but are not limited to, fluorescein, fluorescein isothiocyanate (FITC), OREGON GREEN™, rhodamine, Texas red, tetrarhodimine isothiocynate (TRITC), Cy3, Cy5, and the like), fluorescent markers (e.g., green fluorescent protein (GFP), phycoerythrin, and the like), autoquenched fluorescent compounds that are activated by tumor-associated proteases, enzymes (e.g., luciferase, horseradish peroxidase, alkaline phosphatase, and the like), nanoparticles, biotin, digoxigenin or combination thereof.

Enzymes that can be used as detectable markers in accordance with the embodiments of the disclosure include, but are not limited to, horseradish peroxidase, alkaline phosphatase, acid phosphatase, glucose oxidase, β-galactosidase, β-glucoronidase or β-lactamase. Such enzymes may be used in combination with a chromogen, a fluorogenic compound or a luminogenic compound to generate a detectable signal.

In some embodiments, the antigen binding construct is conjugated to a nanoparticle. The term "nanoparticle" refers to a microscopic particle whose size is measured in nanometers, e.g., a particle with at least one dimension less than about 100 nm. Nanoparticles can be used as detectable substances because they are small enough to scatter visible light rather than absorb it. For example, gold nanoparticles possess significant visible light extinction properties and appear deep red to black in solution. As a result, compositions comprising antigen binding constructs conjugated to nanoparticles can be used for the in vivo imaging of T-cells in a subject. At the small end of the size range, nanoparticles are often referred to as clusters. Metal, dielectric, and semiconductor nanoparticles have been formed, as well as hybrid structures (e.g. core-shell nanoparticles). Nanospheres, nanorods, and nanocups are just a few of the shapes that have been grown. Semiconductor quantum dots and nanocrystals are examples of additional types of nanoparticles. Such nanoscale particles, when conjugated to an antigen binding construct, can be used as imaging agents for the in vivo detection of T-cells as described herein.

Therapeutic Agents

In some embodiments, an antigen binding construct is conjugated to a therapeutic agent. A "therapeutic agent" as used herein is an atom, molecule, or compound that is useful in the treatment of cancer, inflammation, other disease conditions, or to otherwise suppress an immune response, for example immunosuppression in organ transplants. Examples of therapeutic agents include, but are not limited to, drugs, chemotherapeutic agents, therapeutic antibodies and antibody fragments, toxins, radioisotopes, enzymes (e.g., enzymes to cleave prodrugs to a cytotoxic agent at the site of the antigen binding construct binding), nucleases, hormones, immunomodulators, antisense oligonucleotides, chelators, boron compounds, photoactive agents and dyes, and nanoparticles.

Chemotherapeutic agents are often cytotoxic or cytostatic in nature and may include alkylating agents, antimetabolites, anti-tumor antibiotics, topoisomerase inhibitors, mitotic inhibitors hormone therapy, targeted therapeutics and immunotherapeutics. In some embodiments the chemotherapeutic agents that may be used as detectable markers in accordance with the embodiments of the disclosure include, but are not limited to, 13-cis-Retinoic Acid, 2-Chlorodeoxyadenosine, 5-Azacitidine, 5-Fluorouracil, 6-Mercaptopurine, 6-Thioguanine, actinomycin-D, adriamycin, aldesleukin, alemtuzumab, alitretinoin, all-transretinoic acid, alpha interferon, altretamine, amethopterin, amifostine, anagrelide, anastrozole, arabinosylcytosine, arsenic trioxide, amsacrine, aminocamptothecin, aminoglutethimide, asparaginase, azacytidine, bacillus calmette-guerin (BCG), bendamustine, bevacizumab, bexarotene, bicalutamide, bortezomib, bleomycin, busulfan, calcium leucovorin, citrovorum factor, capecitabine, canertinib, carboplatin, carmustine, cetuximab, chlorambucil, cisplatin, cladribine, cortisone, cyclophosphamide, cytarabine, darbepoetin alfa, dasatinib, daunomycin, decitabine, denileukin diftitox, dexamethasone, dexasone, dexrazoxane, dactinomycin, daunorubicin, decarbazine, docetaxel, doxorubicin, doxifluridine, enuluracil, epirubicin, epoetin alfa, erlotinib, everolimus, exemestane, estramustine, etoposide, filgrastim, fluoxymesterone, fulvestrant, flavopiridol, floxuridine, fludarabine, fluorouracil, flutamide, gefitinib, gemcitabine, gemtuzumab ozogamicin, goserelin, granulocyte-colony stimulating factor, granulocyte macrophage-colony stimulating factor, hexamethylmelamine, hydrocortisone hydroxyurea, ibritumomab, interferon alpha, interleukin-2, interleukin-11, isotretinoin, ixabepilone, idarubicin, imatinib mesylate, ifosfamide, irinotecan, lapatinib, lenalidomide, letrozole, leucovorin, leuprolide, liposomal Ara-C, lomustine, mechlorethamine, megestrol, melphalan, mercaptopurine, mesna, methotrexate, methylprednisolone, mitomycin C, mitotane, mitoxantrone, nelarabine, nilutamide, octreotide, oprelvekin, oxaliplatin, paclitaxel, pamidronate, pemetrexed, panitumumab, PEG Interferon, pegaspargase, pegfilgrastim, PEG-L-asparaginase, pentostatin, plicamycin, prednisolone, prednisone, procarbazine, raloxifene, rituximab, romiplostim, ralitrexed, sapacitabine, sargramostim, satraplatin, sorafenib, sunitinib, semustine, streptozocin, tamoxifen, tegafur, tegafur-uracil, temsirolimus, temozolamide, teniposide, thalidomide, thioguanine, thiotepa, topotecan, toremifene, tositumomab, trastuzumab, tretinoin, trimitrexate, alrubicin, vincristine, vinblastine, vindestine, vinorelbine, vorinostat, or zoledronic acid.

Toxins that may be used as detectable markers in accordance with the embodiments of the disclosure include, but are not limited to, ricin, abrin, ribonuclease (RNase), DNase I, Staphylococcal enterotoxin-A, pokeweed antiviral protein, gelonin, diphtheria toxin, *Pseudomonas* exotoxin, and *Pseudomonas* endotoxin.

In some embodiments nanoparticles are used in therapeutic applications as drug carriers that, when conjugated to an antigen binding construct, deliver chemotherapeutic agents, hormonal therapeutic agents, radiotherapeutic agents, toxins, or any other cytotoxic or anti-cancer agent known in the art to cancerous cells that overexpress the target on the cell surface.

Any of the antigen binding constructs described herein may be further conjugated with one or more additional therapeutic agents, detectable markers, nanoparticles, carriers or a combination thereof. For example, an antigen binding construct may be radiolabeled with Iodine 131 and conjugated to a lipid carrier, such that the anti-CD8-lipid conjugate forms a micelle. The micelle can incorporate one or more therapeutic or detectable markers. Alternatively, in addition, the antigen binding construct may be radiolabeled with Iodine 131 (for example, at a tyrosine residue) and conjugated to a drug (for example, at the epsilon amino group of a lysine residue), and the carrier may incorporate an additional therapeutic or detectable marker.

Kits

In some embodiments, kits are provided. In some embodiments, the kit includes an antigen binding construct as described herein. In some embodiments, the kit includes a nucleic acid that encodes an antigen binding construct as described herein. In some embodiments, the kit includes a cell line that produces an antigen binding construct as described herein. In some embodiments, the kit includes a detectable marker as described herein. In some embodiments, the kit includes a therapeutic agent as described herein. In some embodiments, the kit includes buffers. In some embodiments, the kit includes positive controls, for example CD8, CD8+ cells, or fragments thereof. In some embodiments, the kit includes negative controls, for example a surface or solution that is substantially free of CD8. In some embodiments, the kit includes packaging. In some embodiments, the kit includes instructions.

Methods of Detecting the Presence or Absence of the Target Molecule

Antigen binding constructs can be used to detect the presence or absence of the target molecule in vivo and/or in vitro. Accordingly, some embodiments include methods of detecting the presence or absence of the target. The method can include applying an antigen binding construct to a sample. The method can include detecting a binding or an absence of binding of the antigen binding construct to the target molecule, CD8.

Figure 14:
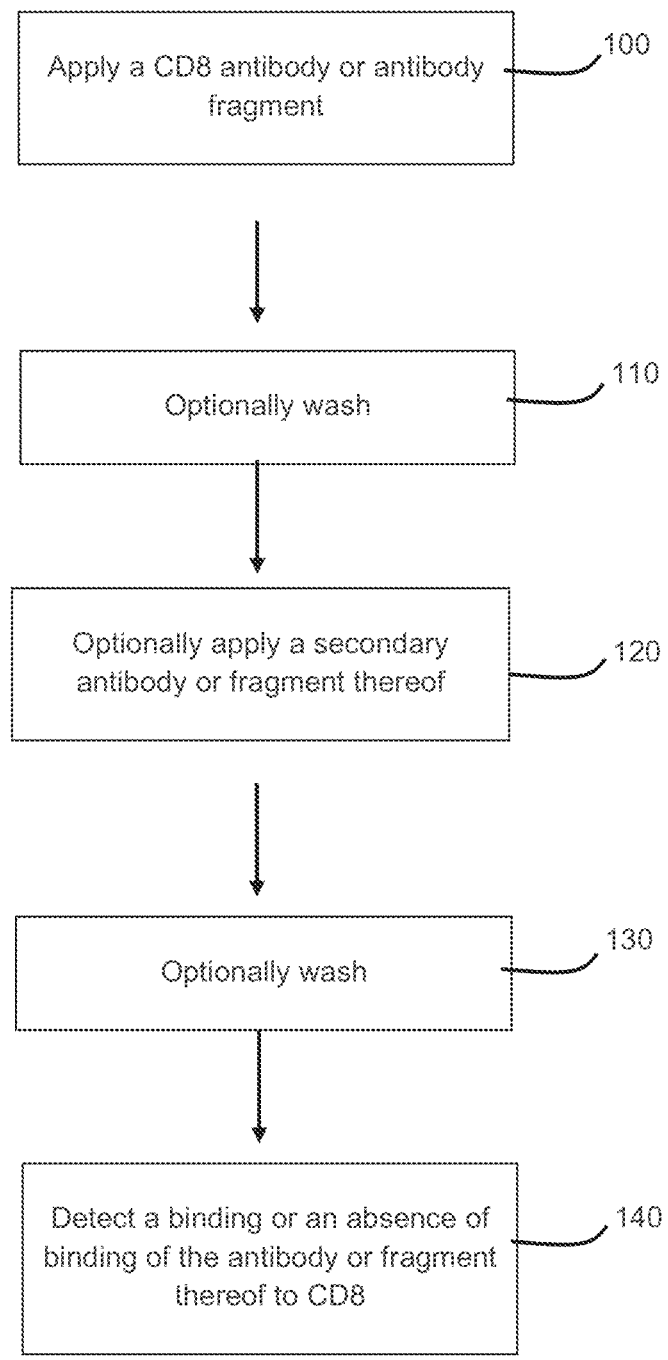
FIG. 14 illustrates some embodiments of a method of detecting a presence or absence of a target.

FIG. 14 illustrates some embodiments of methods of detecting the presence or absence of CD8. It will be appreciated that the steps shown in FIG. 14 can be performed in any sequence, and/or can be optionally repeated and/or eliminated, and that additional steps can optionally be added to the method. An antigen binding construct as described herein can be applied to a sample 100. An optional wash 110 can be performed. Optionally, a secondary antigen binding construct can be applied to the sample 120. An optional wash can be performed 130. A binding or absence of binding of the antigen binding construct to the target molecule can be detected 140.

In some embodiments, an antigen binding construct as described herein is applied to a sample in vivo. The antigen binding construct can be administered to a subject. In some embodiments, the subject is a human. In some embodiments, the subject is a non-human mammal, for example a rat, mouse, guinea pig, hamster, rabbit, dog, cat, cow, horse, goat, sheep, donkey, pig, monkey, or ape. In some embodiments, the antigen binding construct is infused into the subject. In some embodiments, the infusion is intravenous. In some embodiments, the infusion is intraperitoneal. In some embodiments, the antigen binding construct is applied topically or locally (as in the case of an interventional or intraoperative application) to the subject. In some embodiments, a capsule containing the antigen binding construct is applied to the subject, for example orally or intraperitoneally. In some embodiments, the antigen binding construct is selected to reduce the risk of an immunogenic response by subject. For example, for a human subject, the antigen binding construct can be humanized as described herein. In some embodiments, following in vivo application of the antigen binding construct, the sample, or a portion of the sample is removed from the host. In some embodiments, the antigen binding construct is applied in vivo, is incubated in vivo for a period of time as described herein, and a sample is removed for analysis in vitro, for example in vitro detection of antigen binding construct bound to the target molecule or the absence thereof as described herein.

In some embodiments, the antigen binding construct is applied to a sample in vitro. In some embodiments, the sample is freshly harvested from a subject, for example a biopsy. In some embodiments, the sample is incubated following harvesting from a subject. In some embodiments, the sample is fixed. In some embodiments the sample includes a whole organ and/or tissue. In some embodiments, the sample includes one or more whole cells. In some embodiments the sample is from cell extracts, for example lysates. In some embodiments, antigen binding construct in solution is added to a solution in the sample. In some embodiments, antigen binding construct in solution is added to a sample that does not contain a solution, for example a lyophilized sample, thus reconstituting the sample. In some embodiments, lyophilized antigen binding construct is added to a sample that contains solution, thus reconstituting the antigen binding construct.

In some embodiments, the antigen binding construct is optionally incubated with the sample. The antigen binding construct can be incubated for a period of no more than about 10 days, for example no more than about 10 days, 9, 8, 7, 6, 5, 4, 3, 2, or 1 day, or no more than about 23 hours, for example no more than about 23 hours, 22, 21, 20, 19, 18, 17, 16, 15, 14, 13, 12, 11, 10, 9, 8, 7, 6, 5, 4, 3, 2, 1, 0.75, 0.5, 0.25, or 0.1 hour, including ranges between any two of the listed values. In some embodiments, the incubation is within a subject to which the antigen binding construct was administered. In some embodiments, the incubation is within an incubator. In some embodiments, the incubator is maintained at a fixed temperature, for example about 21° C., room temperature, 25° C., 29° C., 34° C., 37° C., or 40° C.

In some embodiments, the antigen binding construct that is not bound to the target is optionally removed from the sample. In some embodiments, the sample is washed. Washing a sample can include removing solution that contains unbound antigen binding construct, and adding solution that does not contain antigen binding construct, for example buffer solution. In some embodiments, an in vitro sample is washed, for example by aspirating, pipetting, pumping, or draining solution that contains unbound antigen binding construct, and adding solution that does not contain antigen binding construct. In some embodiments, an in vivo sample is washed, for example by administering to the subject solution that does not contain antigen binding construct, or by washing a site of topical antigen binding construct administration. In some embodiments, the wash is performed at least two times, for example at least 2, 3, 4, 5, 6, 7, 8, 9, 10, 15, or 20 times. In some embodiments, following the wash or washes, at least about 50% of unbound antibody is removed from the sample, for example at least about 50%, 60%, 70%, 75%, 80%, 85%, 90%, 95%, 97%, 98%, 99% or greater.

In some embodiments, unbound antigen binding construct is eliminated from the sample. Following application of the antigen binding construct to the sample, antigen binding construct bound to the target reaches an equilibrium with antigen binding construct unbound to the target, so that at some time after application of the antigen binding construct, the amount of antigen binding construct bound to the target does not substantially increase. After this time, at least part of the quantity of the antigen binding construct that is unbound to the target can be eliminated. In some embodiments, unbound antigen binding construct is eliminated by metabolic or other bodily processes of the subject to whom the antibody or fragment was delivered. In some embodiments, unbound antigen binding construct is eliminated by the addition of an agent that destroys or destabilized the unbound antigen binding construct, for example a protease or a neutralizing antibody. In some embodiments, 1 day after application of the antigen binding construct, at least about 30% of the antigen binding construct that was applied has been eliminated, for example at least about 30%, 40%, 60%, 70%, 75%, 80%, 85%, 90%, 95%, 97%, 98%, 99%, or 99.9%. In some embodiments, 2 days after application of the antigen binding construct, at least about 40% of the antigen binding construct that was applied has been eliminated, for example at least about 40%, 50%, 60%, 70%, 75%, 80%, 85%, 90%, 95%, 97%, 98%, 99%, or 99.9%.

In some embodiments, the presence or absence of the target, CD8, is detected. The presence or absence of the target can be detected based on the presence or absence of the antigen binding construct in the sample. After removal and/or elimination of the antigen binding construct from the sample, for example by washing and/or metabolic elimination, remaining antigen binding construct in the sample can indicate the presence of the target, while an absence of the antigen binding construct in the sample can indicate the absence of the target. In some embodiments, the antigen binding construct is configured such that it is biased for elimination via the kidneys. In some embodiments, the antigen binding construct is configured such that it is biased for elimination via the liver. In some embodiments, an antigen binding construct comprising at least a portion of a hIgG2 or IgG2 hinge and/or $C_H3$ region as described herein can be configured such that it is cleared substantially via the liver. In some embodiments, an antigen binding construct comprising at least a portion of an IgG2 hinge and/or $C_H3$ region as described herein can be configured such that it is cleared substantially via the liver, but not substantially cleared via the kidney. In some embodiments, the ratio of antigen binding construct eliminated in the liver to antigen binding construct eliminated in the kidney is at least about 2:1, for example about 2:1, 3:1, 3.5:1, 4:1, 5:1, 6:1, 7:1, 8:1, 9:1, 10:1, 20:1, 30:1, 40:1, 50:1, 100:1, or 200:1, including ranges between any of the listed values. In some embodiments, the antigen binding construct remains as a dimer during elimination so as to have a molecular weight that increases the likelihood of elimination via the liver rather than the kidney. In some embodiments, the antigen binding construct maintains an atomic mass greater than the renal threshold of about 60 kDa, for example about 65 kDa, 70 kDa, 80 kDa, 90 kDa, 100 kDa, 120 kDa, 150 kDa, or 200 kDa, including ranges between any two of the listed values.

In some embodiments, the antigen binding construct includes a detectable marker as described herein. Thus, the presence of the antigen binding construct can be inferred by detecting the detectable marker.

In some embodiments, a secondary antigen binding construct is used to detect the antigen binding construct. The secondary antigen binding construct can bind specifically to the antigen binding construct. For example, the secondary antigen binding construct can include a polyclonal or monoclonal antibody, diabody, minibody, etc. against the host type of the antibody, or against the antigen binding construct itself. The secondary antigen binding construct can be conjugated to a detectable marker as described herein. The secondary antigen binding construct can be applied to the sample. In some embodiments, the secondary antigen binding construct is applied to the sample in substantially the same manner as the antigen binding construct. For example, if the antigen binding construct was infused into a subject, the secondary antigen binding construct can also be infused into the subject.

In some embodiments, binding or the absence of binding of the antigen binding construct is detected via at least one of: positron emission tomography (PET), single-photon emission computed tomography (SPECT), magnetic resonance imaging (NMR), or detection of fluorescence emissions. PET can include, but is not limited to microPET imaging. In some embodiments, binding of the absence of binding of the antigen binding construct is detected via two or more forms of imaging. In some embodiments, detection can be via near-infrared (NIR) and/or Cerenkov.

Methods of Targeting a Therapeutic Agent to a Cell

Antigen binding constructs can be used to target a therapeutic molecule, for example a cytotoxin to a target positive cell, such as a cell expressing CD8. Thus, some embodiments include methods of targeting a therapeutic agent to a target positive cell. The method can include administering an antigen binding construct as described herein to a subject. The subject can be a subject in need, for example a subject in need of elimination or neutralization of at least some target positive cells. In some embodiments, the antigen binding construct includes at least on therapeutic agent as described herein. In some embodiments, the therapeutic can be directly conjugated to the antigen binding construct via a covalent bond, such as a disulfide bond. In some embodiments, the subject can benefit from the localization of a CD8 positive cell to another cell or agent.

Optionally, before and/or after administration of the antigen binding construct that includes at least one therapeutic agent, the number and/or localization of the target positive cells of the patient is determined. For example, determining the number and/or localization of target positive cells prior to administration can indicate whether the patient is likely to benefit from neutralization and/or elimination of the target positive cells. Determining the number and/or localization of the target positive cells after administration can indicate whether the target positive cells were eliminated in the patient.

Additional Embodiments

Some embodiments include detection of human CD8 which is a specific biomarker found on the surface of a subset of T-cells for diagnostic imaging of the immune system. Imaging of the target molecule can allow for the in vivo detection of T-cell localization. Changes in T-cell localization can reflect the progression of an immune response and can occur over time as a result various therapeutic treatments or even disease states. For example, imaging T-cell localization can be useful in immunotherapy. Adoptive immunotherapy is a form of therapy where a patient's own T-cells are manipulated in vitro and re-introduced into the patient. For this form of treatment, imaging of T-cells can be useful for monitoring and/or determining the status of the treatment. Thus, in some embodiments, monitoring the localization of the target molecule can be a useful for analyzing a mechanism of action, efficacy, and/or safety in the development of drugs and/or can aid in the clinical management of disease.

In some embodiments, the CDRs of an antigen binding construct that binds specifically to a target, for example for the antibody OKT8, have been adjusted to minibody and cys-diabody arrangements. The CDRs of a murine antibody have been grafted onto a human minibody and cys-diabody framework, thus producing a chimeric minibody. Antibody V domains typically contain two cysteines that form intra-disulfide bonds. The OKT8 $V_H$ has an extra cysteine in framework 3 (FR3) which could interfere with the expression of the protein as it may lead to aggregation and consequently retention in the endoplasmic reticulum. Thus, some embodiments include minibodies made with a serine replacing the extra cysteine in the framework (see, for example, SEQ ID: 16, 18, 20, and 22).

In some embodiments, a method of targeting a CD8+ cell to a first antigen is provided. The method can include applying a bispecific antigen binding construct to a sample. The bispecific antigen binding construct can include a CD8 antigen binding construct as described herein. The bispecific antibody can include an antigen binding construct that binds to the first antigen, for example 1, 2, 3, 4, 5, or 6 CDR's, an scFv, or a monomer of a minibody or cys-diabody. In some embodiments, the bispecific antibody includes 1, 2, or 3 HCDR's of an antigen binding construct as described herein, and/or 1, 2, or 3 LCDR's of an antigen binding construct as described herein. In some embodiments, the bispecific antigen binding construct includes an scFv of an antigen binding construct as described herein. In some embodiment, the bispecific antigen binding construct includes a $V_H$ or $V_L$ sequence as described herein. In some embodiments, the bispecific an antigen binding construct includes a minibody or cys-diabody monomer as described herein. In some embodiments, the bispecific an antigen binding construct is applied to a sample in vivo, for example an organ or tissue of a subject. In some embodiments, the bispecific an antigen binding construct is applied to an in vitro sample. Without being limited to any one theory, in some embodiments, the bispecific an antigen binding construct binds to the target on the target positive cell, and binds to the first antigen (which can be different from CD8) on the first cell, and thus brings the target positive cell in proximity to the first cell. For example, a CD8+ T cell can be brought into proximity of a cancer cell, and can facilitate an immune response against that cancer cell.

In some embodiments, the anti-CD8 antigen binding constructs can be imaging agents that specifically target human CD8+ T-cells. In some embodiments, the anti-CD8 fragments can directly bind and detect the localization of the specific subclass of T-cells that express CD8. In some embodiments, engineered fragments able to cross link CD8 can potentiate signaling through the T cell receptor and enhance the ability of a subject to clear viral pathogens and respond to tumor antigens and vaccines.

In some embodiments, the minibody and cys-diabody antibody formats have desired pharmacokinetic characteristics for diagnostic imaging while maintaining the high binding affinity and specificity of the parental antibody. Compared to imaging with the full-length parental antibody, these fragments clear much faster; yet they are able to target the antigen for rapid high-contrast imaging. The same favorable pharmacokinetic properties are advantageous for targeting immune responses allowing for more controlled T cell stimulation and preventing undesirable effects of over-stimulation (for example, cytokine storms). In preclinical models, the shorter serum half lives for the minibody and the cys-diabody allow for optimal imaging at approximately 16-20 hours post injection for the minibody and 2-6 hours post-injection for the cys-diabody. Same day imaging can provide a significant advantage in the clinic with respect to patient care management.

In addition, the cys-diabody antibody format features the C-terminus cysteine tail. These two sulfhydryl groups (following mild reduction) provide a strategy for site-specific conjugation of functional moieties such as radiolabels that will not interfere with the cys-diabody's binding activity.

In some embodiments, these antigen binding constructs can be diagnostic imaging agents (following labeling with an appropriate radioisotope such as Iodine-124, Cu-64 or Zr-89 (for PET imaging) or fluorophore (for fluorescent imaging)). As clinical imaging agents, these CD8 antigen binding constructs can help to monitor treatment and be used as a patient selection tool.

In some embodiments, the antigen binding constructs can be used for applications where highly specific and high-affinity binding to CD8 is required. Outside of diagnostic imaging, these fragments could serve different purposes depending on the attachment of different functional groups.

With the attachment of the appropriate infrared or fluorescent dye, these constructs can be used as the targeting agent for image-guided intraoperative surgery.

In some embodiments, in addition to the modifications to the functional groups attached to the fragments, through the use of bispecific fragments (where the fragment is able to bind 2 different antigens) it is possible to bring together CD8+ cells to a second antigen. Bispecific full-length antibodies have been used in cancer immunotherapy to bring cytotoxic cells of the immune system to tumor cells. Thus, such embodiments are also contemplated for the appropriate antigen binding constructs.

In some embodiments, provided herein are engineered scFv, minibody, and cys-diabody antibody fragments that are able to bind and specifically target human CD8 alpha both in vitro and in vivo.

Example 1: Humanization of CD8 Antibodies and Antibody Fragments

The murine variable regions of the OKT8 antibody were humanized by grafting the murine Complimentary Determining Region (CDR) onto a human framework. The murine V genes were run against the human V germ-line database. The human V gene with highest sequence homology was examined for functional residues and similarity to antigen binding loop (CDRs) structures. The $V_L$ and $V_H$ CDRs of the murine OKT8 were then incorporated into the human acceptor variable region framework, replacing the human CDRs. An alignment of the corresponding murine, human germline, and humanized sequences is shown for the heavy chain variable regions (FIG. 2A) and light chain variable regions (FIG. 2B). In these figures, the CDRs are boxed and the asterisks indicate residues that differ from each other. Selected mouse residues, known to function in the loop structure, were kept in the human framework.

Example 2: Expression of CD8 Minibodies

The OKT8 minibody constructs (sequence combinations as outlined in Table 0.1) were transiently transfected into CHO-K1 cells to validate expression. The transfections were performed in a 6-well plate using the Lipofectamine reagent (Invitrogen). Following a 72-hour incubation at 37° C. in a $CO_2$ incubator, the supernatants were harvested and filtered to remove any cells.

Figure 15:
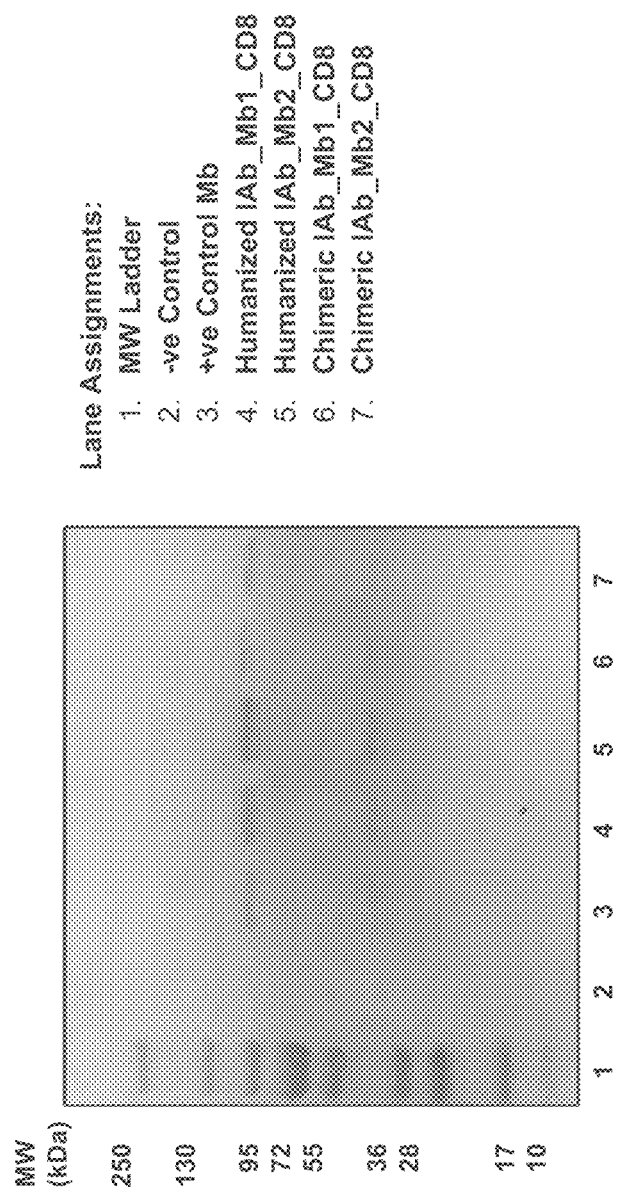
FIG. 15 illustrates a western blot analysis of chimeric and humanized OKT8 minibodies.

Western blot analysis was performed on supernatant from the transient transfections to confirm the expression of the antibody fragments. Supernatant from an empty vector transfection was included as a negative control, and supernatant from the transfection of an irrelevant minibody was used as a positive control. Under non-reducing conditions, the minibodies run at the expected molecular weight of 80-90 kDa (FIG. 15). A minor band representing the monomeric form is also detected at approximately 40 kDa. These results confirm the proper expression of the chimeric and humanized minibodies.

Example 3 Binding

Figure 16:
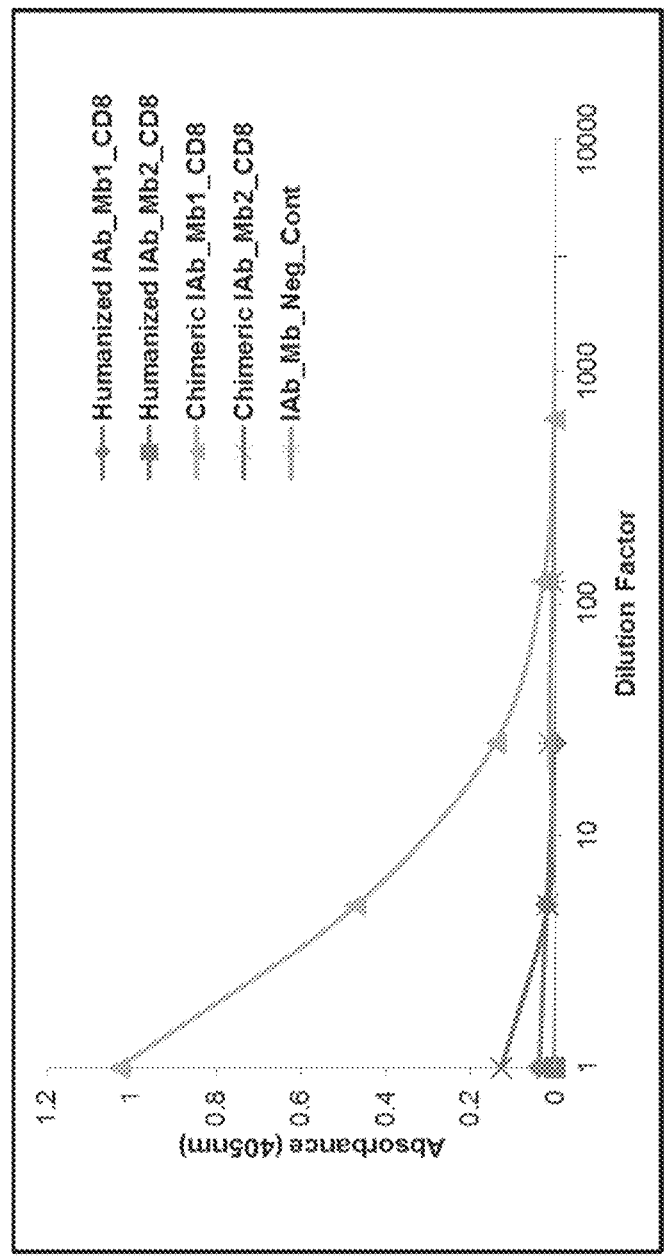
FIG. 16 is a graph displaying binding of the IAb_Mb_CD8 variants to purified rhCD8 by ELISA.
Figure 17A:
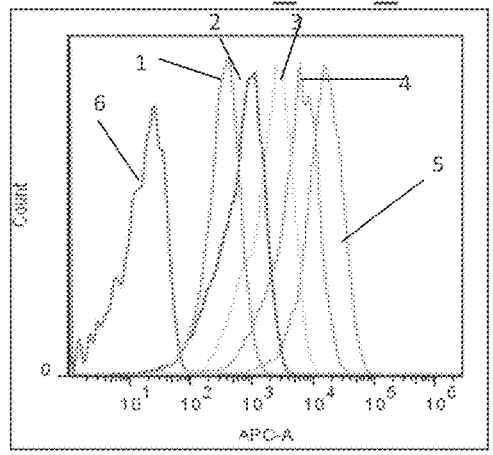
FIGS. 17A-17D depict the results from the flow cytometry analysis of the IAb_Mb_CD8 variants.
Figure 17B:
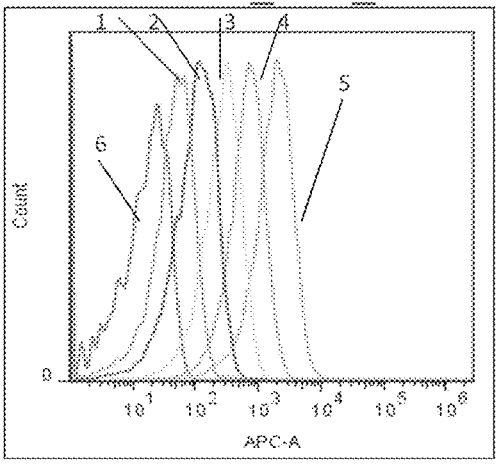
Figure 17C:
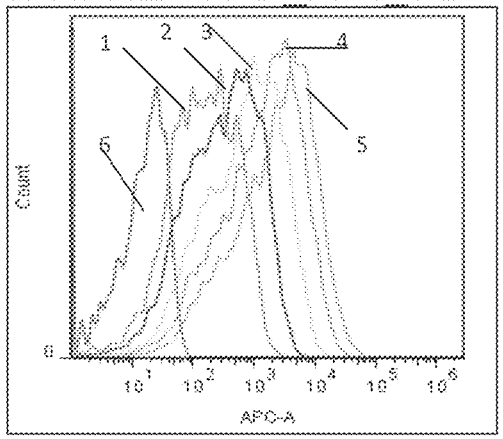
Figure 17D:
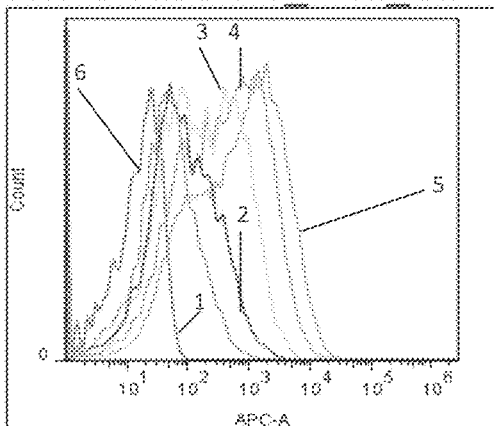

The chimeric minibody variant 1 demonstrated highest binding to CD8 by ELISA whereas the humanized variants did not show any significant binding to CD8 (FIG. 16). Although SPR analysis of the humanized variants showed binding to soluble CD8, several-fold loss in affinity was observed compared to chimeric minibody and parental OKT8 antibody. 96 well plates were coated with the recombinant human CD8 antigen and incubated with supernatants obtained from the transient transfection. Binding was detected with horseradish peroxidase (HRP) conjugated goat anti-human IgG (Fc-specific) and the chromogenic substrate 3,3',5,5'-Tetramethylbenzidine (TMB) measuring the absorbance at 405 nm. Dilutions were done in triplicate. Data is shown as mean of relative absorbance.

FIGS. 17A-17D display the results of the flow cytometry analysis of the IAb_Mb_CD8 variants. All histograms show allophycocyanin (APC) signal vs. counts. Supernatants from transfection of the variants at different dilutions were incubated with CD8+ cells. Cells were washed and subsequently stained with a secondary anti-human IgG (Fc-specific) APC conjugated antibody. 1×10⁵ cells were stained per point and analysis was performed with 10,000 events/point.

The chimeric and humanized minibodies showed concentration-dependent binding to the CD8+ cells (FIGS. 17A-17D). Although the humanized minibodies expressed better than the chimeric, the chimeric minibodies showed a stronger signal by the flow cytometry suggesting the chimeric minibodies possessed stronger binding affinity.

Example 4—Maturation of Antigen Binding Constructs

To improve binding affinity of the humanized antibody fragments, the two humanized $V_H$ regions were further affinity matured. For the version $V_H$, the affinity maturation resulted in sub-versions a and b. For the $2^{nd}$ version $V_H$, the affinity maturation resulted in sub-versions c and d. FIGS. 12F-12I display the resulting antibody variable light ($V_L$) and variable heavy ($V_H$) genes. The DNA with the amino acid sequences are shown. CDRs are boxed using Chothia definition.

The affinity matured humanized OKT8 V genes were engineered into two minibody variants that differed in the orientation of the V genes in the scFv; the $V_L$-$V_H$ orientation referred to as number 1) and $V_H$-$V_L$ orientation referred to as number 2. The specific sequence combinations are outlined in Table 0.2.

Example 5: Expression of CD8 Minibodies

Figure 18A:
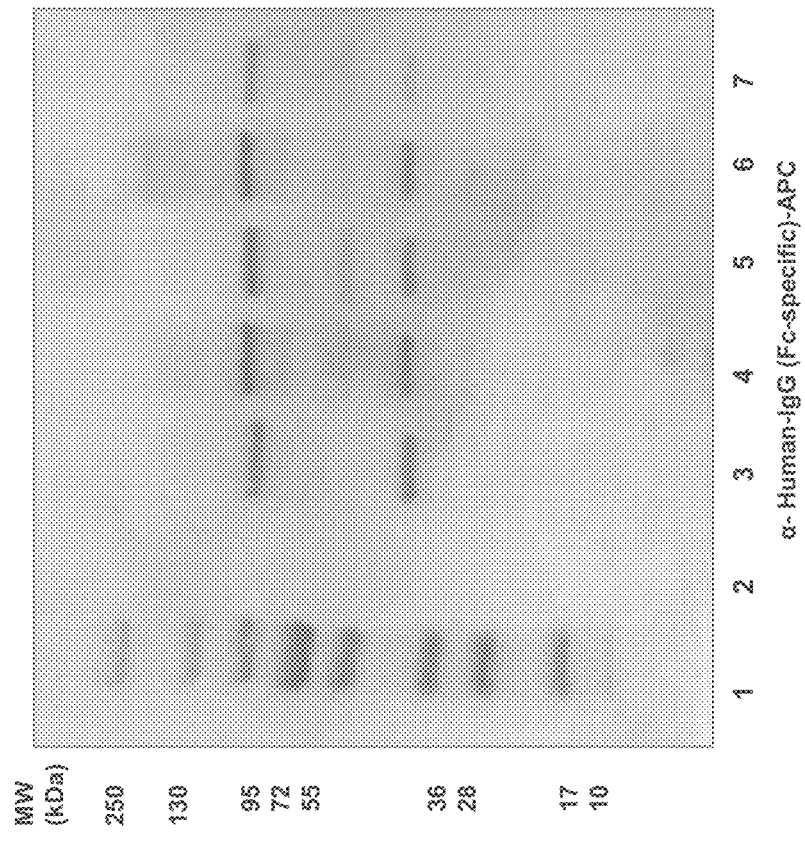

The above IAb_Mb_CD8 expression constructs were transiently transfected into CHO-K1 cells. Supernatant from the transfections was analyzed by Western blot to confirm proper expression of the minibodies. Supernatant from an empty vector transfection was included as a negative control, and purified protein of an irrelevant minibody was used as a positive control. All variants were expressed as evidenced by a band at the expected molecular weight for the assembled minibody complex (~95 kDa) (FIG. 18A and FIG. 18B). The band present at ~45 kDa represents the monomer. Transfection supernatants from transient transfectants were run on SDS-PAGE and transferred to PVDF membrane. The membrane was probed with alkaline phosphatase (AP)-conjugated anti-human IgG (Fc-specific) antibody and developed by incubating with the AP substrate BCIP/NBT. This is a representative blot of multiple experiments.

Figure 19:
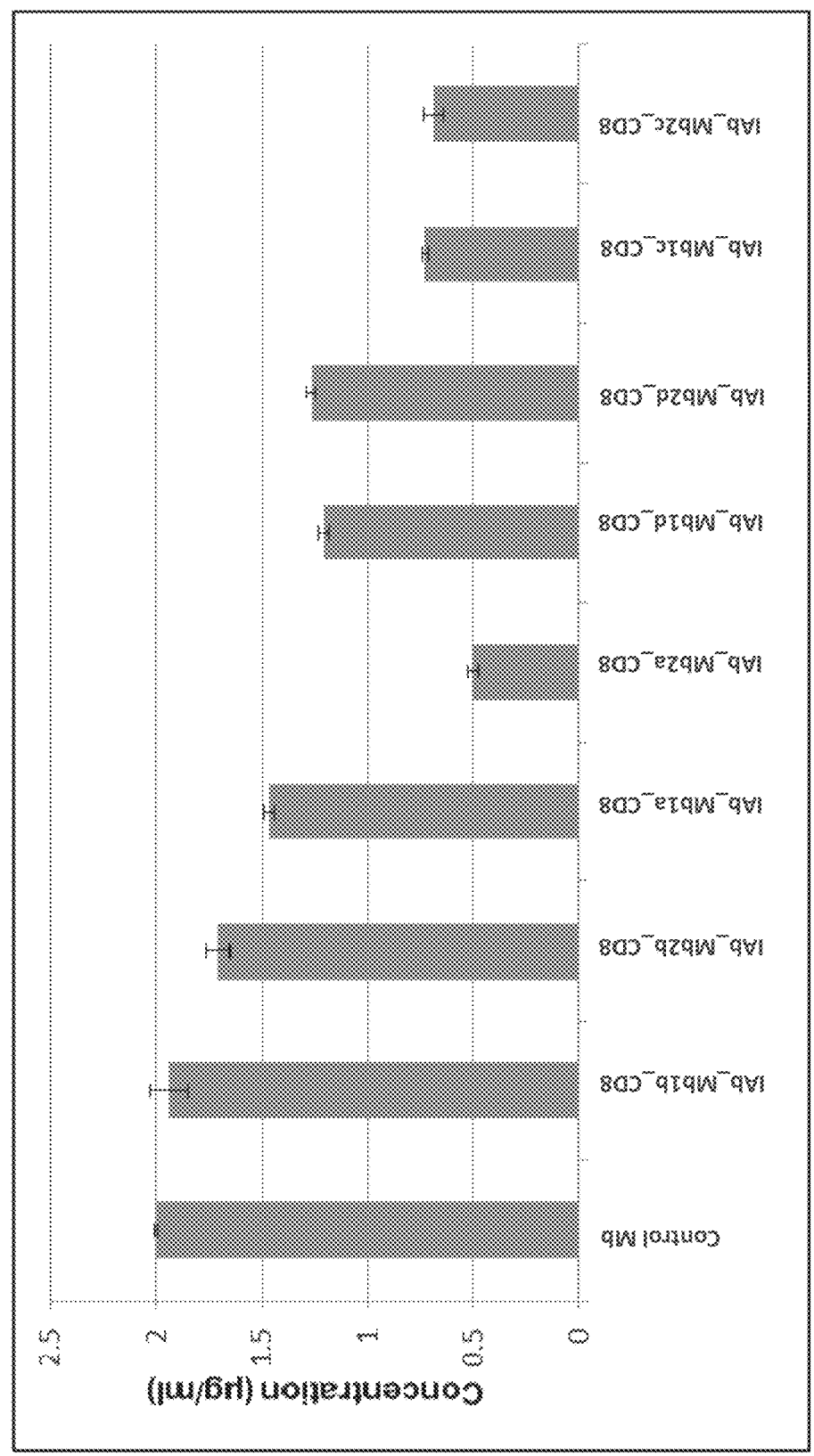
FIG. 19 is a graph displaying IAb_Mb_CD8 expression analysis by ELISA.

Quantitative ELISAs were performed to measure IAb_Mb_CD8 variants expression levels from the transient transfection in CHO-K1 cells. The IAb_Mb_CD8 minibody variants were expressed in a range between ~0.5-1.9 µg/ml, with the higher end of the range being comparable with a previously expressed reference control minibody (FIG. 19). A goat anti-human IgG (Fc specific) was used to capture the minibody and an AP-conjugated goat anti-human IgG (Fc specific) was used for detection. Purified irrelevant isotype control minibody protein was used as a standard. IAb_Mb_CD8 supernatants were serially diluted to find dilution points which fit in the linear range of the standard curve.

Example 6: Functional Activity of Minibodies

To demonstrate the functional activity of the IAb_Mb_CD8 minibody variants, the supernatants from the transient transfection were tested for binding to purified recombinant human CD8 protein by ELISA. The concentration of the variants IAb_Mb1b_CD8, IAb_Mb2b_CD8, and IAb_Mb1a_CD8 were normalized to match the concentration of IAb_MB2a_CD8 (0.5 µg/ml) based on the quantitative ELISA presented in FIG. 19. Samples were then serially diluted to assess binding over a series of concentrations. The parental OKT8 antibody was also included as a positive control for the assay (data not shown). All minibody variants showed concentration dependent binding to soluble recombinant human CD8 (rhCD8).

Figure 20:
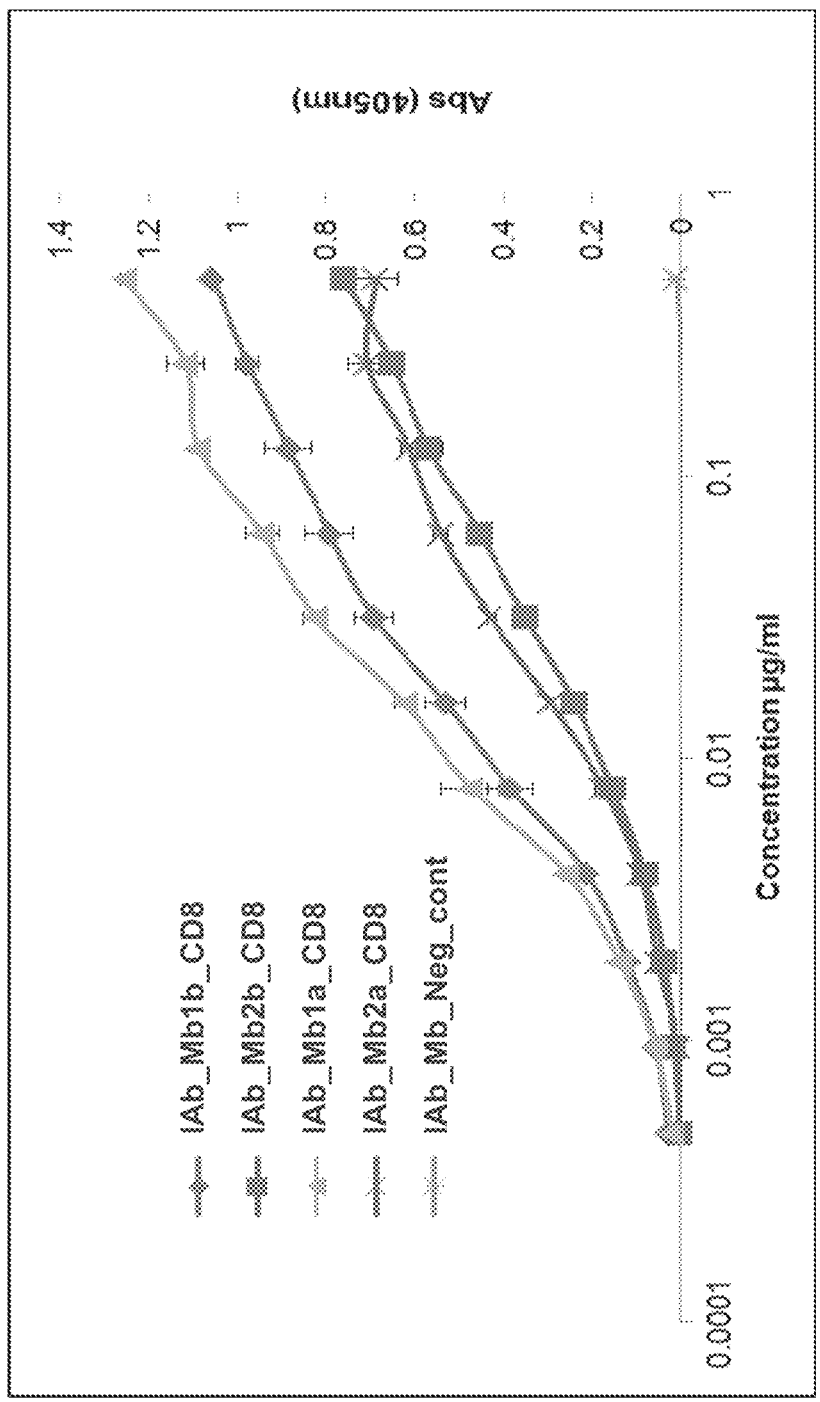
FIG. 20 is a graph depicting the binding of the IAb_Mb_CD8 variants A and B to rhCD8 by ELISA.

FIG. 20 indicates that IAb_Mb1a_CD8 followed by IAb_Mb1b_CD8 has the highest level of binding to the antigen. 96 well plates were coated with rhCD8 antigen and incubated with supernatants obtained from the transient transfection. Binding was detected with HRP-conjugated goat anti-human (Fc-specific) IgG and TMB substrate. The absorbance measured at 405 nm. Dilutions were done in triplicate. Data is shown as mean of relative absorbance.

Figure 21:
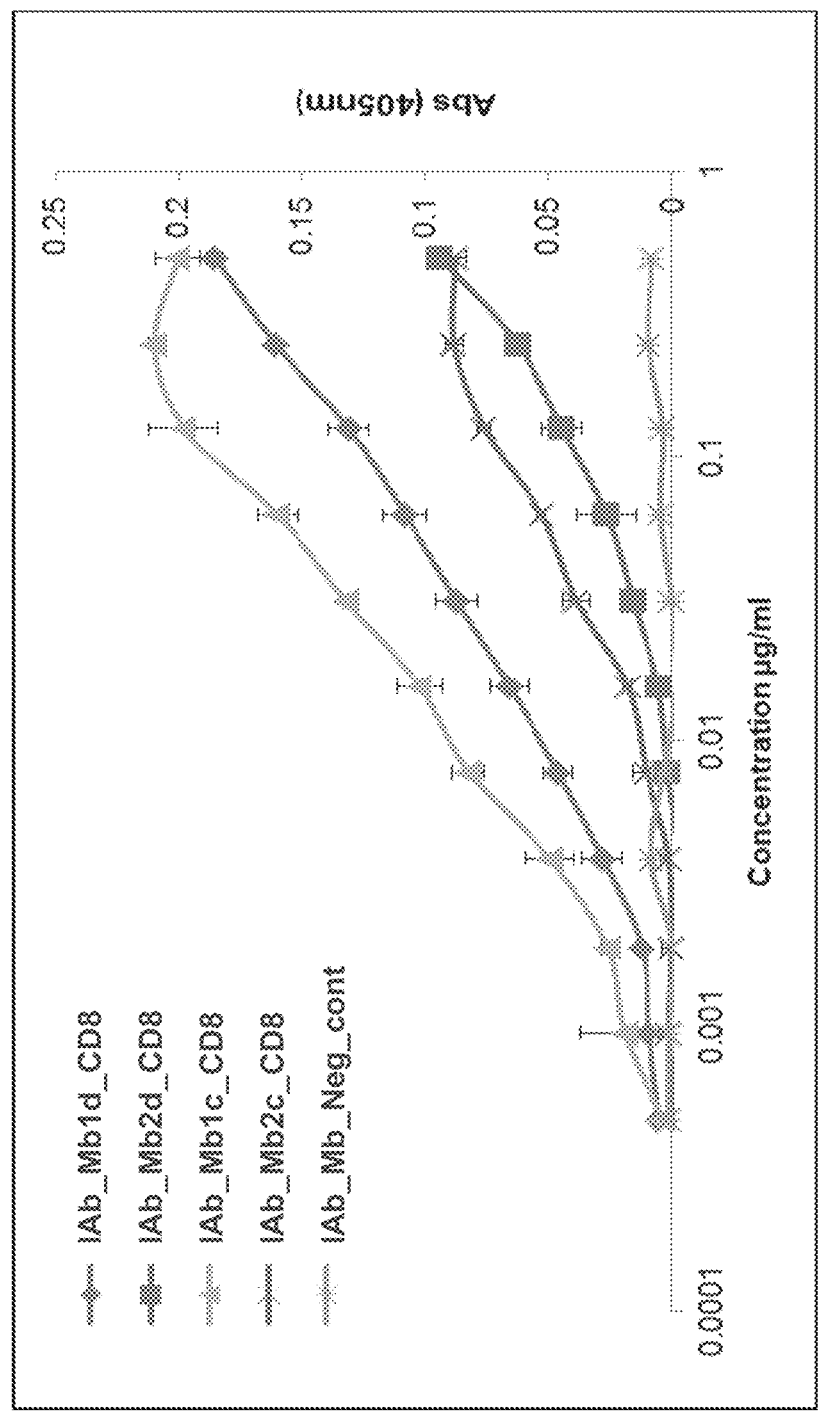
FIG. 21 is a graph depicting the binding of IAb_Mb_CD8 variants C and D to rhCD8 by ELISA.

FIG. 21 indicated that variant 1c has the highest level of binding followed by variant 1c. 96 well plates were coated with rhCD8 antigen and incubated with supernatants obtained from the transient transfection. Binding was detected with HRP-conjugated goat anti-human (Fc-specific) IgG and TMB substrate. The absorbance measured at 405 nm. Dilutions were done in triplicate. Data is shown as mean of relative absorbance.

Example 7: Binding to Cellular Human CD8

IAb_Mb_CD8 variants were evaluated for binding to cellular human CD8 using flow cytometry. Supernatants from the transient transfection were tested for binding to PC3-CD8 cells (PC3 cells stably transfected with human CD8) (FIGS. 22A and 22B and 23A and 23B). The minibody supernatants were normalized for the flow cytometry experiment. The parental OKT8 was included as a positive control for binding (data not shown). PC3 cells was used as negative control and confirmed that the minibody variants did not bind (data not shown). IAb_Mb1b_CD8 demonstrated the highest Mean Fluorescence Intensity (MFI) of the four minibody variants.

In regard to the results presented in FIGS. 22A and 22B, all histograms show APC signal vs. counts. Supernatants from transfection of the variants were incubated with PC3-CD8 cells. Cells were washed and subsequently stained with APC-conjugated anti-human IgG (Fc-specific) antibody. 1×10⁵ cells were stained per point and analysis was performed with 10,000 events/point.

Figure 23B:
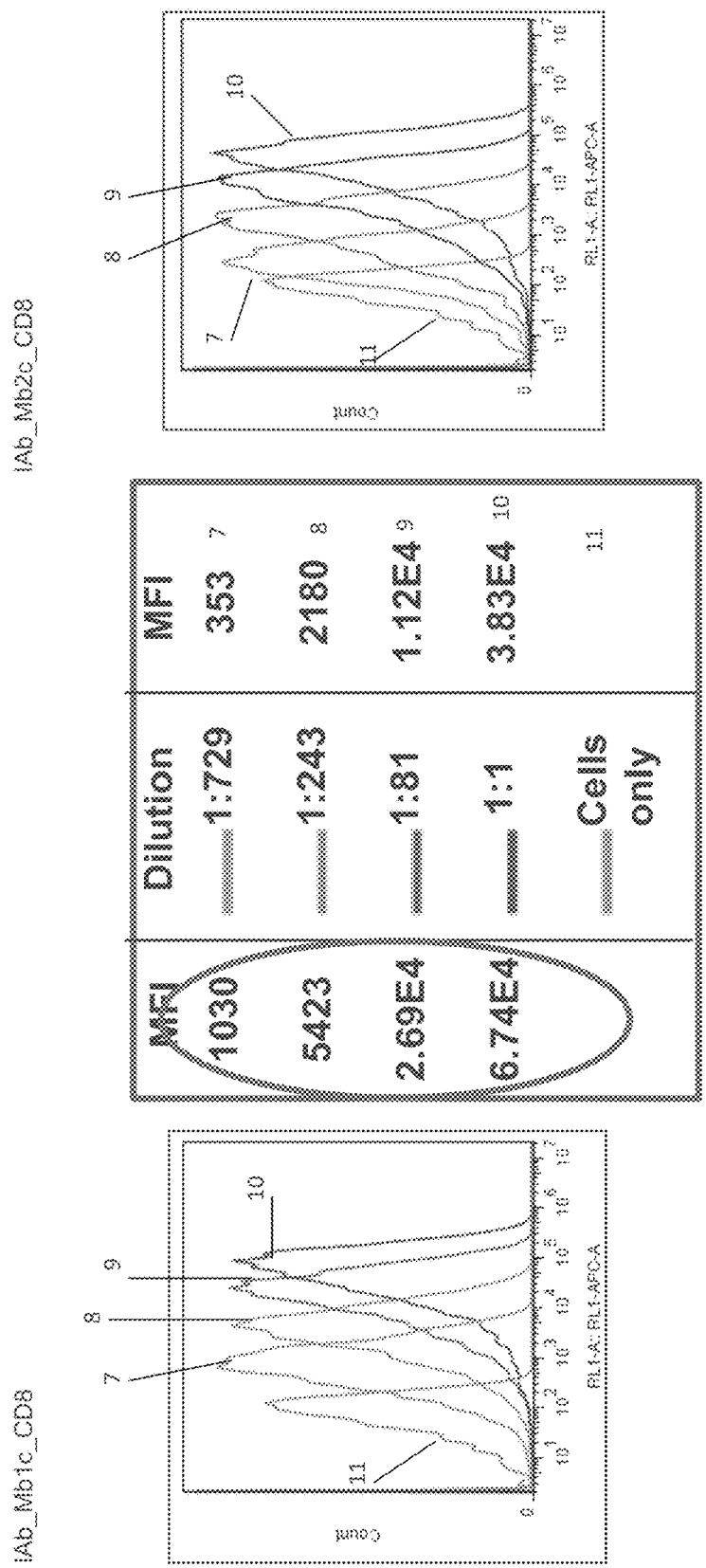

In regard to the results presented in FIGS. 23A and 23B, all histograms show APC signal vs. counts. Supernatants from transfection of the variants were incubated with PC3-CD8 cells. Cells were washed and subsequently stained with APC-conjugated anti-human IgG (Fc-specific) antibody. 1×10⁵ cells were stained per point and analysis was performed with 10,000 events/point.

The results indicated that the constructs still bind to cellular human CD8.

Example 8: SPR Analysis

Surface plasma resonance (SPR) was used to determine the binding affinity for all the IAb_Mb_CD8 variants to recombinant human CD8 (Table 8.0). The minibody protein in the supernatant was captured on to the BIAcore chip using an anti-human IgG (Fc-specific) antibody. The amount of minibody captured on the chip was normalized to enable a direct comparison of binding affinity between the variants as a kinetic "scouting" experiment to rank affinities. The rhCD8 protein was passed over the captured minibody protein to measure binding. All variants showed strong binding to CD8 protein that was similar to the parental OKT8 mAb.

TABLE 8.0

| Ligand | Analyte | ka (1/Ms) | kd (1/s) | Conc of analyte | KA (1/M) | KD (M) |
|---|---|---|---|---|---|---|
| OKT8 mAb | hCD8 | $5.6 \times 10^5$ | $1.0 \times 10^{-3}$ | 50 nM | $5.5 \times 10^8$ | $1.8 \times 10^{-9}$ |
| IAb_Mb1b_CD8 | hCD8 | $6.4 \times 10^5$ | $1.2 \times 10^{-3}$ | 50 nM | $5.4 \times 10^8$ | $1.9 \times 10^{-9}$ |
| IAb_Mb2b_CD8 | hCD8 | $5.4 \times 10^5$ | $2.1 \times 10^{-3}$ | 50 nM | $2.6 \times 10^8$ | $3.9 \times 10^{-9}$ |
| IAb_Mb1a_CD8 | hCD8 | $6.5 \times 10^5$ | $1.2 \times 10^{-3}$ | 50 nM | $5.3 \times 10^8$ | $1.9 \times 10^{-9}$ |
| IAb_Mb2a_CD8 | hCD8 | $4.8 \times 10^5$ | $2.2 \times 10^{-3}$ | 50 nM | $2.2 \times 10^8$ | $4.6 \times 10^{-9}$ |
| IAb_Mb1d_CD8 | hCD8 | $7.0 \times 10^5$ | $2.0 \times 10^{-3}$ | 50 nM | $3.4 \times 10^8$ | $2.9 \times 10^{-9}$ |
| IAb_Mb2d_CD8 | hCD8 | $5.4 \times 10^5$ | $2.9 \times 10^{-3}$ | 50 nM | $1.8 \times 10^8$ | $5.5 \times 10^{-9}$ |
| IAb_Mb1c_CD8 | hCD8 | $7.0 \times 10^5$ | $1.8 \times 10^{-3}$ | 50 nM | $4.0 \times 10^8$ | $2.5 \times 10^{-9}$ |
| IAb_Mb2c_CD8 | hCD8 | $7.2 \times 10^5$ | $3.2 \times 10^{-3}$ | 50 nM | $2.2 \times 10^8$ | $4.5 \times 10^{-9}$ |

Table 8.0 summarizes the measured association (ka), dissociation (kd), and kD constants for the IAb_Mb_CD8 variants binding to recombinant hCD8. The variants were captured on a BIAcore chip using anti-human Fc-specific IgG antibody.

In some embodiments, antigen binding constructs that bind in the nanomolar range (for example 1 to 2, 2 to 10, 10 to 100, or 100 to 1,000 nM) are provided and include minibody, cys-diabody, and scFv arrangements (for example).

Example 9: Expression of CD8 Cys-Diabodies

The cys-diabody constructs as outlined in Table 0.3 (humanized version b) were transiently transfected into CHO-K1 cells to validate expression. The transfections were performed in a 6-well plate using the Lipofectamine reagent. Following a 72-hour incubation at 37° C. in a $CO_2$ incubator, the supernatants were harvested and filtered to remove any cells.

Figure 24:
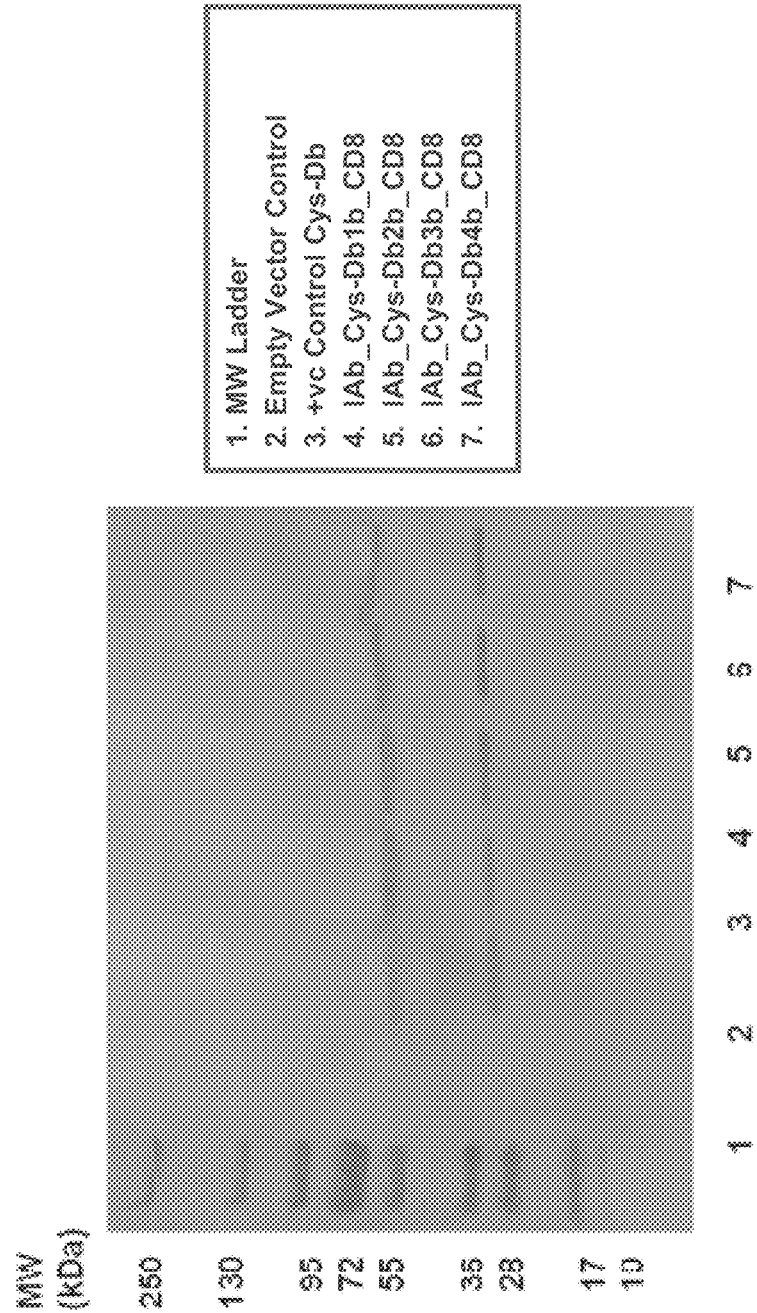
FIG. 24 depicts an image of a western blot analysis of IAb_Cys-Dba_CD8 variants.

A western blot analysis was performed using supernatant from the transient transfections to confirm the expression of the antibody fragments. Supernatant from an empty vector transfection was included as a negative control, and supernatant from the transfection of an irrelevant cys-diabody was used as a positive control. Under non-reducing conditions, all four variants of the humanized OKT8 cys-diabody ran at the appropriate molecular weight of approximately 55 kD (FIG. 24). A minor band representing the monomeric form is also detected at approximately 25 kD. These results confirm the proper expression of the humanized OKT8 cys-diabodies. For the western blot, supernatants were collected following transient transfection into CHO-K1 cells. Transfection supernatants were electrophoresed by SDS-PAGE under non-reducing conditions and transferred to a PVDF membrane. The membrane was probed with an HRP-conjugated anti-His antibody and developed with the HRP substrate TMB.

Example 10: Binding for CD8 Cys-Diabodies

The supernatants from the transient transfection of the IAb_Cys-Dbb_CD8 variants were tested for binding to recombinant human CD8 (rhCD8) protein by ELISA. Samples were serially diluted to assess binding over a range of concentrations prior to incubation with CD8. 96 well plates were coated with rhCD8 antigen. Coated plates were incubated with supernatants following transient transfection of the different cys-diabody variants, and then incubated with HRP-conjugated anti-His antibody. The signal was detected using TMB and absorbance measured at 405 nm.

Figure 25:
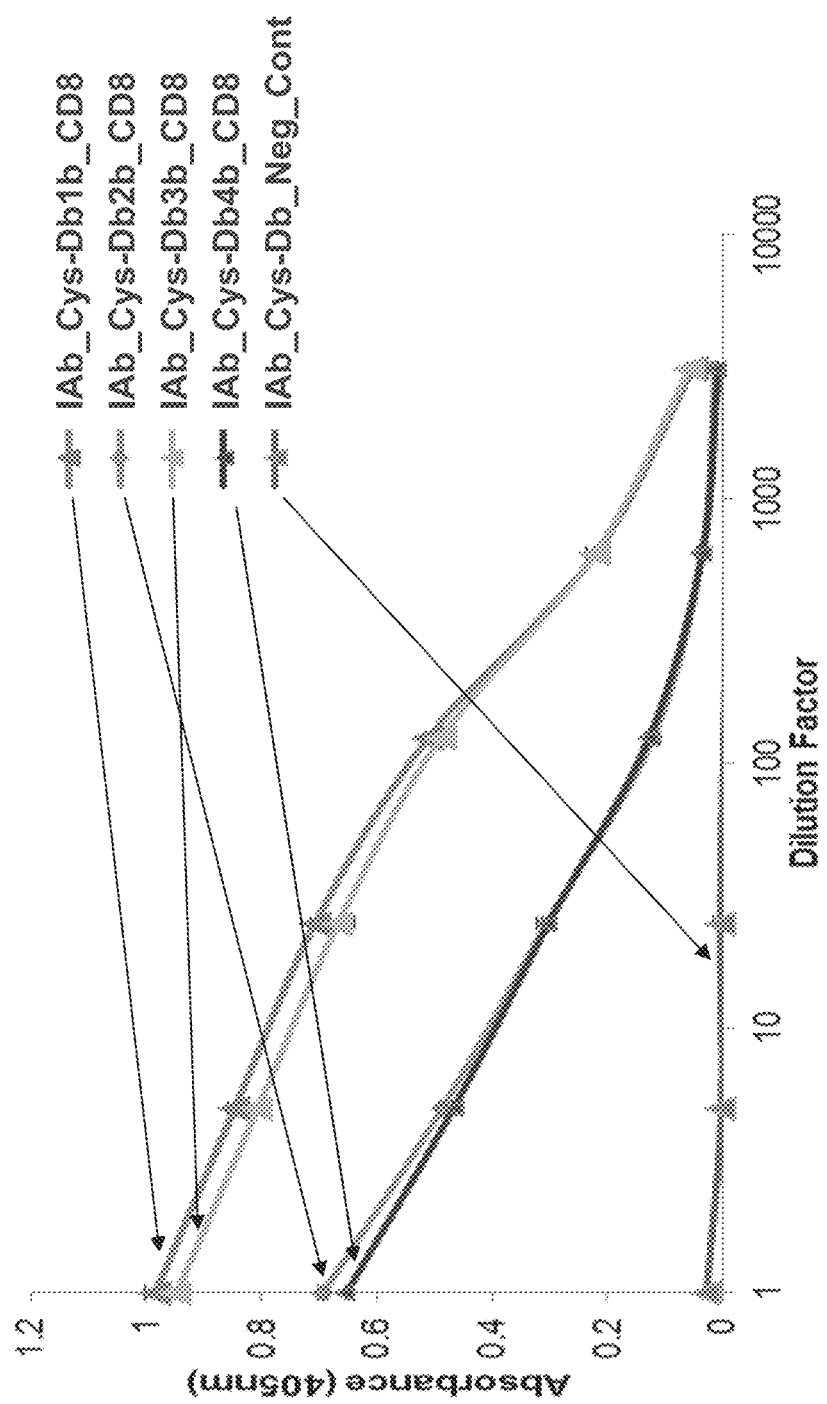
FIG. 25 is a graph depicting the binding of IAb_Cys-Dba_CD8 variants to rhCD8 by ELISA.

All four variants exhibited concentration-dependent binding to the rhCD8 protein (FIG. 25). The transfection supernatant from a negative control cys-diabody that was included in the analysis did not show any binding to CD8 (FIG. 25).

All four IAb_Cys-Dbb_CD8 variants were further tested for binding to cellular human CD8 using flow cytometry. Supernatants from the transient transfection were tested for binding to a PC3-CD8 cells (FIGS. 26A and 26B). The parental OKT8 was included as a positive control for binding (data not shown). The PC3 cells were included as negative control and confirmed that there was no non-specific binding of the cys-diabody variants to this cell (data not shown). IAb_Cys-Db1b_CD8 and IAb_Cys-Db3b_CD8 demonstrated higher Mean Fluorescence Intensity (MFI) compared to the other two variants. All histograms in FIGS. 26A and 26B show APC signal vs. counts. Supernatants from transfection of the variants were evaluated for binding to PC3-CD8 cells. Cells were subsequently stained with APC-conjugated anti-His antibody. $1 \times 10^5$ cells/point and 10,000 events were analyzed for each point.

The IAb_Cys-Dbb_CD8 variants were evaluated for their ability to bind endogenous CD8 expressing HPB-ALL cells. All IAb_Cys-Db1b and 3b variants bound to the HPB-ALL cells (FIG. 27). The parental OKT8 was included as a positive control for binding, and the PC3 cells were included as negative cell line. No binding was seen by the cys-diabody variants on PC3 cells that did not express CD8 (data not shown). Supernatants from transfection of the variants were evaluated for binding to endogenous CD8 expressing HPB-ALL cells. Cells were subsequently stained with APC-conjugated anti-His antibody. All histograms show APC signal vs. counts. $1 \times 10^5$ cells/point and 10,000 events were analyzed for each point.

Example 11: In Vivo Detection of CD8

A humanized CD8 cys-diabody of Table 0.3 is conjugated with a relevant chelator via C-terminal cysteines on the cys-diabody and subsequently radiolabeled with an isotope of In111, (or in the alternative, Zr-89 or Cu-64). Alternatively, the cys-diabody can be radiolabeled after attaching relevant chelators to Lysine residues or directly radiolabeled with Iodine.

The cys-diabody is infused intravenously into a healthy human subject. The cys-diabody is incubated in the human subject for 10 minutes post-infusion. Within the same day as the incubation, the localization of the cys-diabody is detected via a PET scan or external scintillation system.

Localization of cys-diabody is used to determine localization of CD8 in the subject.

Example 12: In Vivo Detection of CD8

A minibody from Table 0.2 is conjugated with a relevant chelator via Lysine residues on the minibody and subsequently radiolabeled with an isotope of In111 (or in the alternative, Zr89 or Cu64). Alternatively, the minibody can be radiolabeled by directly radiolabeling with Iodine via Tyrosine residues.

The minibody is infused intravenously into a healthy human subject. The minibody is incubated in the human subject for 10 minutes post-infusion. On the same day as the incubation, the localization of the minibody is detected via a PET scan or external scintillation system.

Localization of cys-diabody is used to determine localization of CD8 in the subject.

Example 13: In Vivo Detection of CD8

A humanized CD8 minibody that is a homodimer of monomers of SEQ ID NO: 22 is provided. The minibody is infused intravenously into a healthy human subject. The minibody is incubated in the human subject for 1 hour post-infusion. A secondary antibody, a humanized cys-diabody that binds specifically to the CD8 minibody and is conjugated to 33P is provided. Within the same day as the incubation, the secondary antibody is infused into to subject. The secondary antibody is incubated for one hour. The localization of the minibody is detected via PET imaging, via a marker on the secondary antibody.

Localization of minibody is used to determine localization of CD8 in the subject.

Example 14: Therapeutic Treatment Using a Cys-Diabody

A CD8 cys-diabody that is a homodimer of monomers of Table 0.3 is provided. The cys-diabody is infused intravenously into a subject having a CD8 related disorder in an amount adequate to bind to sufficient levels of CD8 in the subject to provide a lessening of the symptoms of the CD8 related disorder. The cys-diabody is conjugated to Yttrium 90.

Example 15: Therapeutic Treatment Using a Minibody

A CD8 minibody of Table 0.2 is provided. The minibody is injected into a patient who has been vaccinated with an antigen to an infectious disease or with a tumor associated antigen. The CD8 directed fragments augment the immune response and enhance the cytolytic activity of CD8 expressing T cells.

Example 16: Therapeutic Treatment Using a Cys-Diabody

A CD8 cys-diabody that is a homodimer of a monomer of Table 0.3 is provided. The cys-diabody is infused intravenously into a subject having a CD8 related disorder in an amount adequate to bind to sufficient levels of CD8 in the subject to provide a lessening of the symptoms of the CD8 related disorder. The cys-diabody is conjugated to Lu177Tx.

The CD8 cys-diabody binds to a cell expressing CD8 and the Lu177Tx results in the killing of the cell.

Example 17: Flow Cytometry Analysis of OKT8 mAb Binding to CD8 on HPB-ALL Cells

Figure 28:
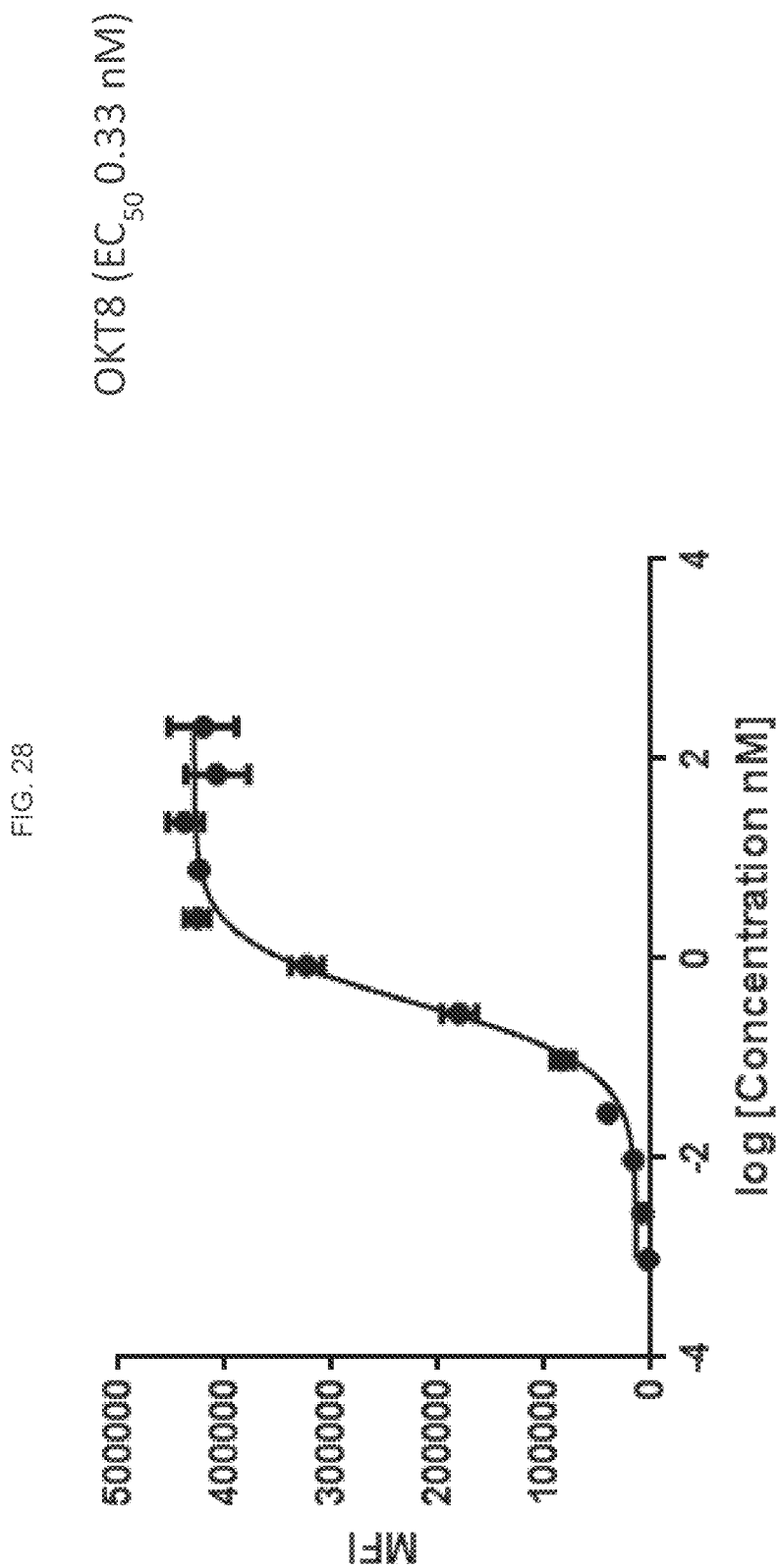
FIG. 28 is a graph depicting flow cytometry analysis of an OKT8 construct according to some embodiments herein.

Flow cytometry analysis of the OKT8 mAbconstruct binding to cell-surface human CD8 on HPB-ALL cells was performed. Cells were stained with respective concentrations of antibody, washed, and then stained with a secondary anti-mouse IgG (Fc-specific) APC-conjugated antibody. Analysis was performed with 10,000 events/point in triplicate for each concentration. The results are shown in graph format in FIG. 28. The graph presents the mean fluorescence intensity (MFI) vs. the log of the concentration (nM). Error bars represent the standard error. The data indicates an $EC_{50}$ of 0.22 nM.

Figure 29A:
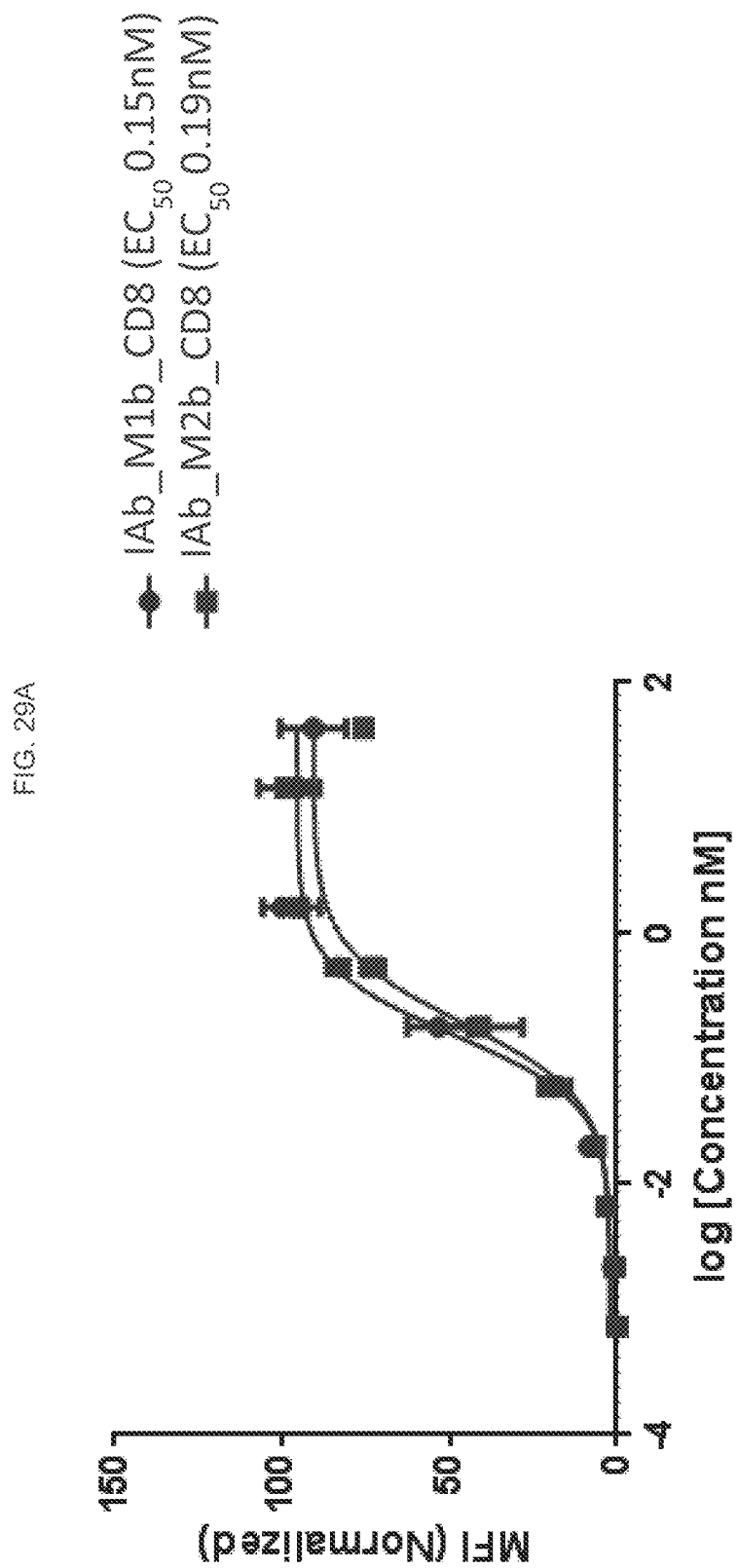
FIG. 29A is a graph depicting flow cytometry analysis of an IAb M1b CD8 and IAb M2b CD8 construct according to some embodiments herein.

Example 18A: Flow Cytometry Analysis of Minibody Binding to CD8 on HPB-ALL Cells Flow cytometry analysis of minibodies binding to cell-surface human CD8 on HPB-ALL cells was performed. Cells were stained with respective concentrations of minibody, washed, and then stained with a secondary anti-human IgG (Fc-specific) APC-conjugated antibody. Analysis was performed with 10,000 events/point in triplicate for each concentration. The results are shown in graph format in FIG. 29A. The graph presents the normalized mean fluorescence intensity (MFI) vs. the log of the concentration (nM). Error bars represent the standard error. The data indicates an $EC_{50}$ of 0.15 nM and 0.19 nM.

Example 18B: Flow Cytometry Analysis of Minibody Binding to CD8 on CD8+ T Cells

Flow cytometry analysis of minibodies binding to cell-surface human CD8 on primary human CD8+ T cells was performed. Cells were stained with respective concentrations of minibody, washed, and then stained with a secondary anti-human IgG (Fc-specific) APC-conjugated antibody. Analysis was performed with 10,000 events/point in triplicate for each concentration. The results are shown in graph format in FIG. 29B. The graph presents the normalized mean fluorescence intensity (MFI) vs. the log of the concentration (nM). Error bars represent the standard error. The data indicates an $EC_{50}$ of 0.1 nM and 0.26 nM.

Figure 29C:
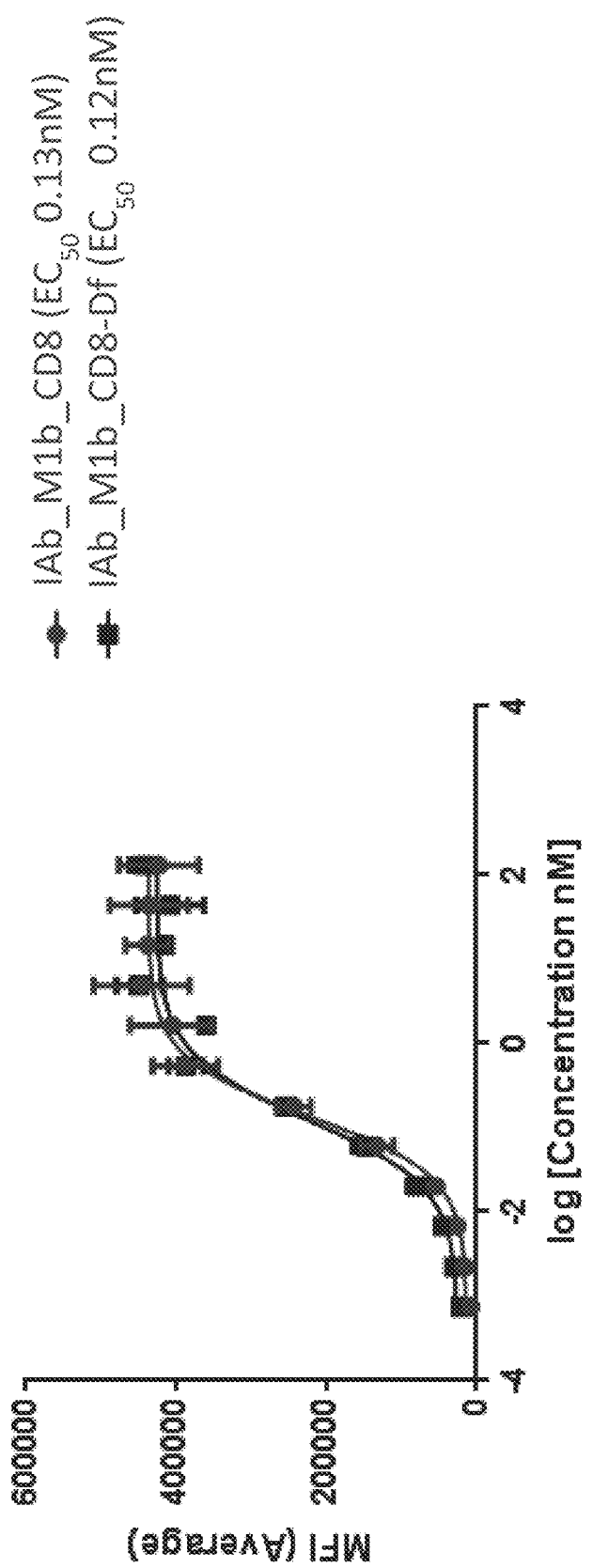
FIG. 29C is a graph depicting flow cytometry analysis of an IAb M1b CD8 and IAb M1b CD8-Df construct according to some embodiments herein.

Example 18C: Flow Cytometry Analysis of Df-Labeled and Unlabeled Minibody Binding to CD8 on HPB-ALL Cells Flow cytometry analysis of minibody (+/− lysine conjugation to Desferoxamine (Df)) binding to cell-surface human CD8 on HPB-ALL cells was performed. Cells were stained with respective concentrations of minibody, washed, and then stained with a secondary anti-human IgG (Fc-specific) APC-conjugated antibody. Analysis was performed with 10,000 events/point in triplicate for each concentration. The results are shown in graph format in FIG. 29C. The graph presents the mean fluorescence intensity (MFI) vs. the log of the concentration (nM). Error bars represent the standard error. The data indicates an $EC_{50}$ of 0.13 nM and 0.12 nM.

Figure 29D:
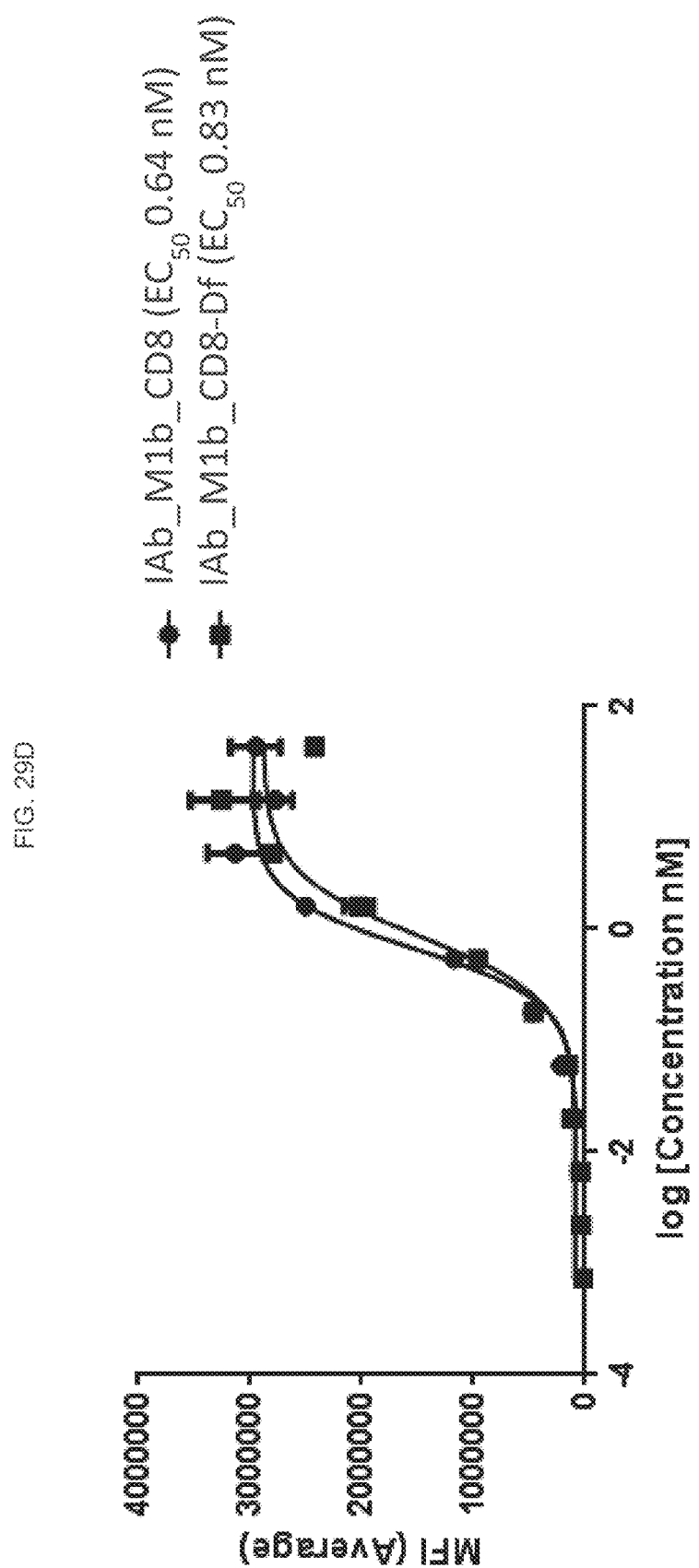
FIG. 29D is a graph depicting flow cytometry analysis of an IAb M1b CD8 and IAb M1b CD8-Df construct according to some embodiments herein.

Example 18D: Flow Cytometry Analysis of Df-Labeled and Unlabeled Minibody Binding to CD8 on PC3 Cells Flow cytometry analysis of minibody (+/− lysine conjugation to Desferoxamine) binding to PC3 cells overexpressing CD8 was performed. Cells were stained with respective concentrations of minibody, washed, and then stained with a secondary anti-human IgG (Fc-specific) APC-conjugated antibody. Analysis was performed with 10,000 events/point in triplicate for each concentration. The results are shown in graph format in FIG. 29D. The graph presents the mean fluorescence intensity (MFI) vs. the log of the concentration (nM). Error bars represent the standard error. The data indicates an $EC_{50}$ of 0.64 nM and 0.83 nM.

Example 18E: Flow Cytometry Analysis of Df-Labeled and Unlabeled Minibody Binding to CD8 on PC3 Cells Flow cytometry analysis of IgG2 minibodies binding to cell-surface human CD8 on HPB-ALL cells was performed. Cells were stained with respective concentrations of minibody, washed, and then stained with a secondary anti-human IgG (Fc-specific) APC-conjugated antibody. Analysis was performed with 10,000 events/point in triplicate for each concentration. The results are shown in graph format in FIG. 29E. The graph presents the normalized mean fluorescence intensity (MFI) vs. the log of the concentration (nM). Error bars represent the standard error. The data indicates an $EC_{50}$ of 0.1 nM, 0.13 nM, and 0.08 nM.

Figure 30A:
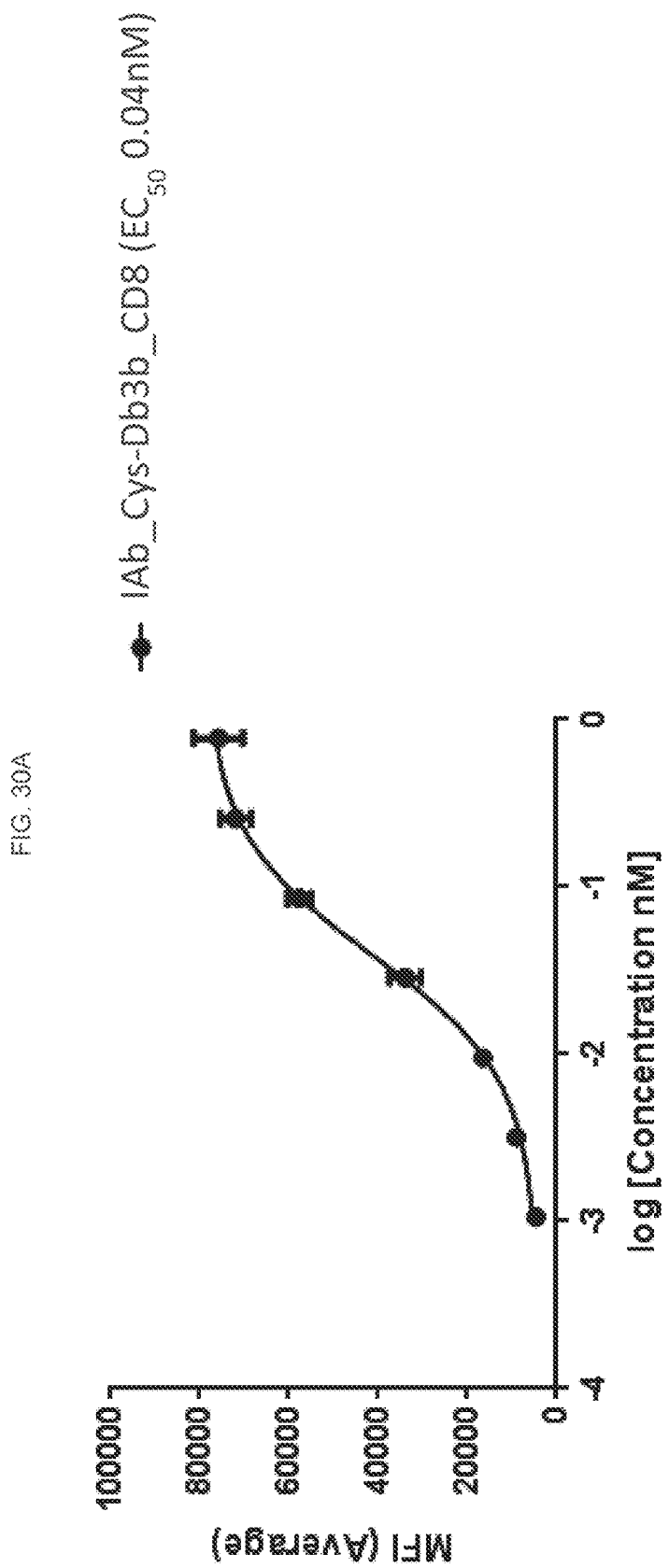
FIG. 30A is a graph depicting flow cytometry analysis of an IAb_CysDb3b_CD8 construct according to some embodiments herein.

Example 19A: Flow Cytometry Analysis of Cys-Diabody Binding to CD8 on HPB-ALL Cells Flow cytometry analysis of cys-diabody binding to cell-surface human CD8 on HPB-ALL cells was performed. Cells were stained with respective concentrations of cys-diabody, washed, stained with a secondary Protein L conjugated to Biotin, washed, then stained with a tertiary streptavidin-APC. Analysis was performed with 10,000 events/point in triplicate for each concentration. The results are shown in graph format in FIG. 30A. The graph presents the mean fluorescence intensity (MFI) vs. the log of the concentration (nM). Error bars represent the standard error. The data indicates an $EC_{50}$ of 0.04 nM.

Figure 30B:
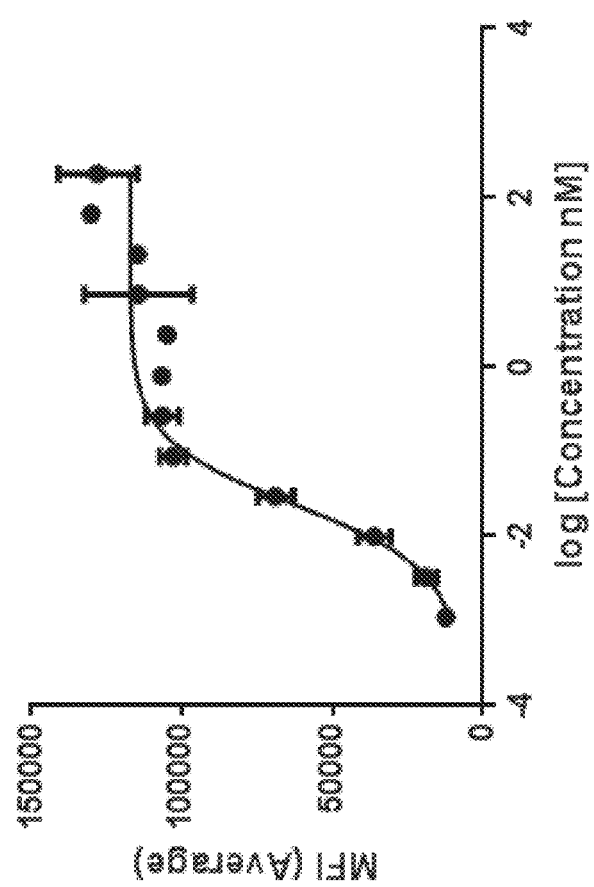
FIG. 30B is a graph depicting flow cytometry analysis of an IAb_CysDb3b_CD8 construct according to some embodiments herein.

Example 19B: Flow Cytometry Analysis of Cys-Diabody Binding to CD8 on CD8+ T Cells Flow cytometry analysis of cys-diabody binding to cell-surface human CD8 on primary human CD8+ T cells was performed. Cells were stained with respective concentrations of cys-diabody, washed, stained with a secondary Protein L conjugated to Biotin, washed, then stained with a tertiary streptavidin-APC. Analysis was performed with 10,000 events/point in triplicate for each concentration. The results are shown in graph format in FIG. 30B. The graph presents the mean fluorescence intensity (MFI) vs. the log of the concentration (nM). Error bars represent the standard error. The data indicates an $EC_{50}$ of 0.02 nM.

Example 19C: Flow Cytometry Analysis of Df-Labeled and Unlabeled Cys-Diabody Binding to CD8 on HPB-ALL Cells Flow cytometry analysis of cys-diabody (+/−C-terminal cysteine conjugation to Desferoxamine) binding to cell-surface human CD8 on HPB-ALL cells was performed. Cells were stained with respective concentrations of cys-diabody, washed, stained with a secondary Protein L conjugated to Biotin, washed, then stained with a tertiary streptavidin-APC. Analysis was performed with 10,000 events/point in triplicate for each concentration. The results are shown in graph format in FIG. 30C. The graph presents the mean fluorescence intensity (MFI) vs. the log of the concentration (nM). Error bars represent the standard error. The data indicates an $EC_{50}$ of 0.04 nM and 0.06 nM.

Example 20: Characterization of Constructs by Flow Cytometry

Table 9, shown below, summarizes the results of characterization of minibody and cys-diabody constructs from Examples 18A-18E and 19A-19C.

TABLE 9

| Construct Name | Cell Binding (EC50) | SPR |
|---|---|---|
| OKT8 | 0.33 nM HPB-ALL | $K_D$ 1.8 nM |
| IAb_M1b_CD8 | 0.1 nM HPB-ALL | $K_D$ 1.9 nM |
|  | 0.1 nM huCD8+ |  |
|  | 0.6 nM CD8-PC3 |  |
| IAb_M2b_CD8 | 0.19 nM HPB-ALL | $K_D$ 3.6 nM |
|  | 0.26 nM huCD8+ |  |
| IAb_M1b_CD8 IgG2 NH | 0.08 nM HPB-ALL | N/A |
| IAb_M1b_CD8 IgG2 EH | 0.13 nM HPB-ALL | N/A |
| IAb_Cys-Db3b_CD8 | 0.04 nM HPB-ALL | N/A |
|  | 0.02 nM huCD8+ |  |

Example 21: Imaging Human CD8-Expressing Tumor Xenografts Human CD8 Tumor Xenografts with $^{89}$Zr-Df-IAb_Cys-Db3b_CD8

Eight (8) female SCID mice were studied. Four (4) mice were implanted with 5×10$^6$ PC3-hCD8 cells and another four (4) were implanted with PC3 (hCD8 negative) cells in the right shoulder region. The mice were i.v. injected with $^{89}$Zr-Df-IAb_Cys-Db3b_CD8 (Df-conjugated to C-terminal cysteine residues). Six (6) mice (4 with positive and 2 with negative tumor) were imaged at 4 h, 6 h and 24 h by PET (10 min static scans). One mouse was also subjected to a 0-2 h dynamic scan. Biodistribution was performed after the last scan at 24 hrs.

The images obtained are depicted in FIG. 31. FIG. 31 depicts coronal and transverse PET images at 4, 6 and 24 hrs of the same SCID mouse carrying PC3-hCD8 xenograft in the right shoulder region (see arrowheads). The mouse was i.v. injected with approximately 120 μCi of $^{89}$Zr-Df-IAb_Cys-Db3b_CD8 (specific activity was 4.96 μCi/μg). Without being limited by theory, the Cys-Db clearly delineates the tumor at 6 h and clears via the kidneys as expected. At 24 hour, the average positive to negative tumor (PC3-hCD8 to PC3) ratio was ~1.6-fold. Average positive tumor to blood ratio was 16.0 (negative to blood 9.5)

Example 22: Imaging Human CD8-Expressing Tumor Xenografts Human CD8 Tumor Xenografts with $^{89}$Zr-Df-IAb_M1b_CD8 A Eight (8) female SCID mice were studied. Four (4) mice were implanted with 5×10$^6$ PC3-hCD8 cells and another four (4) were implanted with PC3 (hCD8 negative) cells in the right shoulder region. The mice were i.v. injected with $^{89}$Zr-Df-IAb_M1b_CD8 (Cys)-minibody with IgG1 hinge-extension and $C_H3$ with Df-conjugated to cysteine residues in the hinge region. Six (6) mice (4 with positive and 2 with negative tumor) were imaged at 4 h, 24 h and 48 h by PET (10 min static scans) followed by 10 min CT scan for anatomical reference. One mouse was also subjected to a 0-2 h dynamic scan. Biodistribution was performed after the last scan at 48 hrs.

Figure 32A:
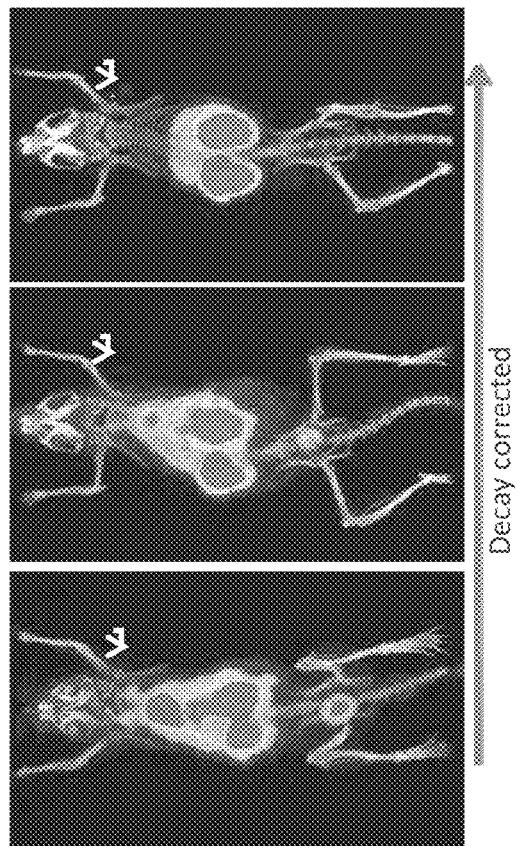
FIG. 32A is a series of coronal MIP PET/CT overlay images of mice labeled with $^{89}$Zr-Df-IAb_M1b_CD8 constructs according to some embodiments herein.

The images obtained are depicted in FIG. 32A. FIG. 32A depicts coronalCoronal MIP PET/CT overlay images at 2, 4 and 24 hrs of the same SCID mouse carrying PC3-hCD8 xenograft in the right shoulder region (see arrowheads). The mouse was i.v. injected with approximately 116 µCi of $^{89}$Zr-Df-IAb_M1b_CD8 (Cys) (specific activity was 5.16 µCi/µg). Some tumor uptake was seen at 4 and 24 hrs. The majority of activity was cleared via the kidneys which had 4-5-fold higher uptake than the liver at 48 hrs. Without being limited by theory, the high kidney uptake indicates that the Mb falls apart after conjugation with Df so as to exist as a monomer (half-molecule) of 40 kDa (a size that is below the renal threshold of 60 kDa) and not a dimer of 80 kDa. At 48 h and tumor and organs harvested and counted for radioactivity. The uptake in the positive tumor was significantly higher than that in the negative tumor (P=0.02933). The positive tumor to blood ratio was 11.0 (negative tumor to blood 5.6)

Figure 32B:
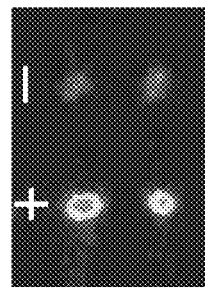
FIG. 32B is a table juxtaposed with an image depicting labeling of excised tumors labeled with $^{89}$Zr-Df-IAb_M1b_CD8 constructs according to some embodiments herein.

Excised tumors were imaged separately at 48 hrs. As shown in FIG. 32B, despite being mainly a monomer, a much higher activity is retained in the positive tumor (+) vs. that in the negative tumor (−) with the Mb. As indicated by the results discussed above, it appears that minibody constructs can have additional advantages when more than three cysteines are present in each half of the hinge region.

Figure 33:
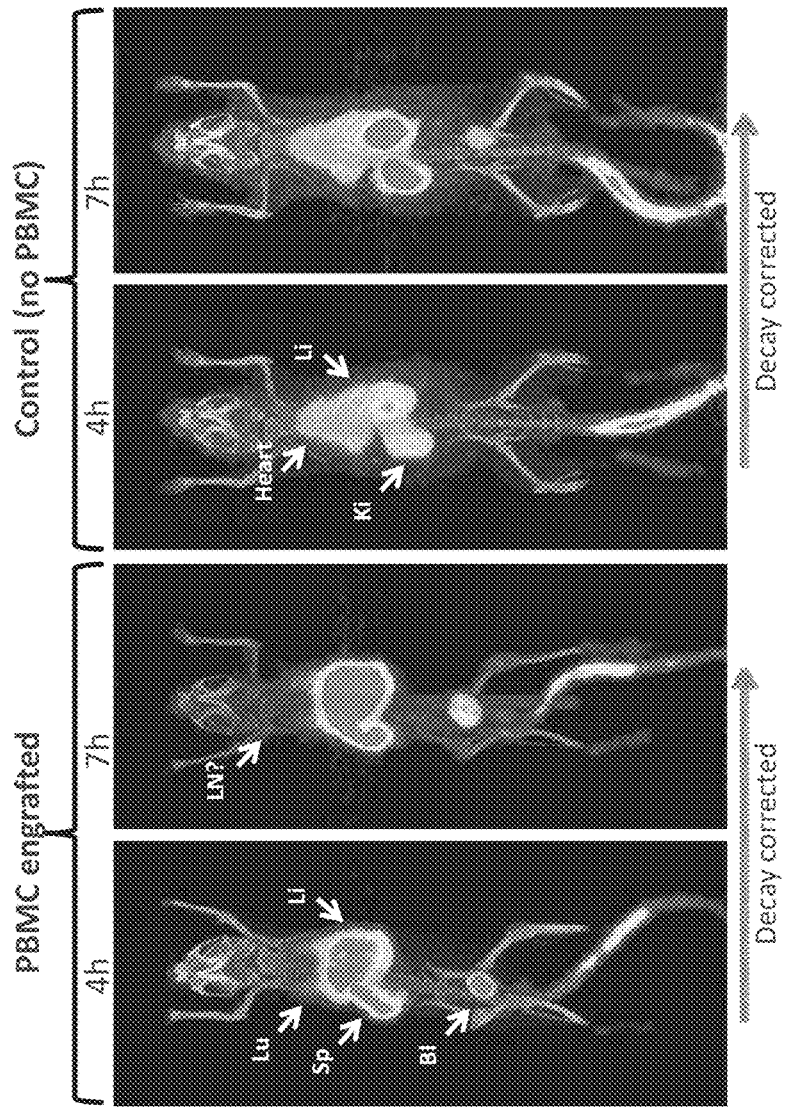
FIG. 33 is a series of MIP images of mice labeled with $^{64}$Cu-NODAGA-IAb_M1B_CD8 IgG2 EH (Cys) constructs according to some embodiments herein.

Example 23: Imaging Human Human CD8 T Cells Cells with $^{64}$Cu-NODAGA-IAb_M1b_CD8 IgG2 EH Six female NOD Scid Gamma (NSG) mice were studied. Three mice were engrafted with 20×10$^6$ fresh human peripheral blood mononuclear cells (PBMC; 98% viability) by injection into the lateral tail vein. This treatment results resulted in uniformly high engraftment in the spleen regardless of the donor used. After 3-4 weeks all mice were i.v. injected with $^{64}$Cu-NODAGA-IAb_M1b_CD8 IgG2 EH (Cys)-Mb with IgG2 hinge-extension and $C_H3$ domain with NODAGA conjugated to cysteine residues in the hinge region. All six mice were imaged at 4 hours. One mouse from each group was imaged at 7 hours. Biodistribution was performed at 7 hours The images obtained are depicted in FIG. 33. FIG. 33 depicts MIP images of the two NSG mice (one PBMC engrafted and on not) that were scanned at 4 and 7 hrs. Approximately 84 µCi of $^{64}$Cu-NODAGA-IAb_M1b_CD8 IgG2 EH (Cys) (specific activity of 7.41 µCi/µg) was administered into each mouse. High uptake in the spleen (Sp) and possibly in axillary lymph nodes (LN) is seen in the PBMC engrafted mouse. In the NSG mouse, the Mb is mainly cleared via the liver (Li). Without being limited by theory, liver clearance was expected for an 80 kDa fragment. In the negative control mouse the blood activity remained high and activity was distributed to both liver and kidneys (Ki). At 7 h, biodistribution in PBMC engrafted NSG mice showed: 2.1-fold higher uptake in spleen, 4.0-fold lower activity in kidneys, 1.7-fold higher activity in the liver and 3.1-fold lower activity in the blood relatively to that of the control.

In this application, the use of the singular can include the plural unless specifically stated otherwise or unless, as will be understood by one of skill in the art in light of the present disclosure, the singular is the only functional embodiment. Thus, for example, "a" can mean more than one, and "one embodiment" can mean that the description applies to multiple embodiments.

INCORPORATION BY REFERENCE

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application; including but not limited to defined terms, term usage, described techniques, or the like, this application controls.

EQUIVALENTS

The foregoing description and Examples detail certain embodiments. It will be appreciated, however, that no matter how detailed the foregoing may appear in text, the invention may be practiced in many ways and the invention should be construed in accordance with the appended claims and any equivalents thereof.

We claim:

1. A cys-diabody or minibody that comprises:
   a variable heavy (V$_H$) domain comprising:
      a HCDR1 of a HCDR1 of SEQ ID NO: 3 or 6;
      a HCDR2 of a HCDR2 of SEQ ID NO: 3 or 6;
      a HCDR3 of a HCDR3 of SEQ ID NO: 3 or 6; and
      a HFR3 of a HFR3 of SEQ ID NO: 48; and
   a variable light (V$_L$) domain comprising:
      a LCDR1 of LCDR1 of SEQ ID NO: 9;
      a LCDR2 of a LCDR2 of SEQ ID NO: 9; and
      a LCDR3 of a LCDR3 of SEQ ID NO: 9.

2. The cys-diabody or minibody of claim 1, wherein the cys-diabody or minibody binds specifically to CD8.

3. The cys-diabody or minibody of claim 1, further comprising a detectable marker.

4. The cys-diabody or minibody of claim 1, further comprising a therapeutic agent.

5. The cys-diabody or minibody of claim 1, wherein the cys-diabody or minibody is bispecific.

6. The cys-diabody or minibody of claim 1, wherein the cys-diabody or minibody is monospecific.

7. A cys-diabody that binds to CD8, the cys-diabody comprising a polypeptide that comprises:
   a single-chain variable fragment (scFv) comprising a variable heavy (V$_H$) domain linked to a variable light (V$_L$) domain; and
   a C-terminal cysteine,
   the V$_H$ domain comprising:
   a HCDR1 of a HCDR1 of SEQ ID NO: 3 or 6;
   a HCDR2 of a HCDR2 of SEQ ID NO: 3 or 6;
   a HCDR3 of a HCDR3 of SEQ ID NO: 3 or 6; and
   a HFR3 of a HFR3 of SEQ ID NO: 48; and
   the V$_L$ domain comprising:
   a LCDR1 of LCDR1 of SEQ ID NO: 9;
   a LCDR2 of a LCDR2 of SEQ ID NO: 9; and
   a LCDR3 of a LCDR3 of SEQ ID NO: 9.

8. The cys-diabody of claim 7, wherein the order of the variable domains, from N terminus to C terminus of the polypeptide is V$_L$, V$_H$.

9. The cys-diabody of claim 7, wherein the order of the variable domains, from N terminus to C terminus of the polypeptide is V$_H$, V$_L$.

10. The cys-diabody of claim 7, further comprising a detectable molecule.

11. A minibody that binds to CD8, the minibody comprising a polypeptide that comprises from N-terminus to C-terminus:
    a single-chain variable fragment (scFv) that binds to CD8, the scFv comprising a variable heavy (V$_H$) domain linked to a variable light (V$_L$) domain, wherein the minibody comprises:
       a HCDR1 of a HCDR1 of SEQ ID NO: 3 or 6;
       a HCDR2 of a HCDR2 of SEQ ID NO: 3 or 6;
       a HFR3 of a HFR3 of SEQ ID NO: 48;
       a HCDR3 of a HCDR3 of SEQ ID NO: 3 or 6;
       a LCDR1 of LCDR1 of SEQ ID NO: 9;
       a LCDR2 of a LCDR2 of SEQ ID NO: 9; and
       a LCDR3 of a LCDR3 of SEQ ID NO: 9;
    a hinge-extension domain comprising a human IgG1 hinge region; and
    a human IgG C$_H$3 sequence.

12. The minibody of claim 11, further comprising a detectable marker.

13. The minibody of claim 3, wherein the detectable marker comprises $^{89}$Zr.

14. The minibody of claim 12, wherein the detectable marker comprises $^{89}$Zr.

15. The cys-diabody or minibody of claim 1, wherein:
    the V$_H$ domain comprises the amino acid sequence in SEQ ID NO: 48, and
    the V$_L$ domain comprises the amino acid sequence in SEQ ID NO: 42.

16. The minibody of claim 11,
    wherein the V$_H$ domain is of SEQ ID NO: 48, and
    wherein the V$_L$ domain is of SEQ ID NO: 42.

17. The minibody of claim 1, the V$_L$ domain further comprising a LFR1 of a LFR1 in SEQ ID NO: 42.

18. The minibody of claim 11, the V$_L$ domain further comprising a LFR1 of a LFR1 in SEQ ID NO: 42.

19. A minibody that comprises:
    a variable heavy (V$_H$) domain comprising:
       the amino acid sequence of positions 26-31 of SEQ ID NO: 48;

the amino acid sequence of positions 50-58 of SEQ ID NO: 48;

the amino acid sequence of positions 99-107 of SEQ ID NO: 48; and the amino acid sequence of positions 59-98 of SEQ ID NO: 48; and a variable light ($V_L$) domain comprising:

the amino acid sequence of positions 24-34 of SEQ ID NO: 42;

the amino acid sequence of positions 50-56 of SEQ ID NO: 42; and the amino acid sequence of positions 89-97 of SEQ ID NO: 42.

20. The minibody of claim 19, wherein the $V_H$ domain is of SEQ ID NO: 48, and wherein the $V_L$ domain is of SEQ ID NO: 42.

21. The minibody of claim 20, further comprising a detectable maker.

\* \* \* \* \*